United States Patent [19]

Rowan et al.

[11] Patent Number: 5,084,377

[45] Date of Patent: Jan. 28, 1992

[54] CRYOGENIC SUSPENSION METHOD

[76] Inventors: Larry Rowan, 3440½ Caroline Ave.; Larry Rosenberg, 3440 Caroline Ave., both of Culver City, Calif. 90230

[21] Appl. No.: 260,389

[22] Filed: Oct. 20, 1988

Related U.S. Application Data

[63] Continuation-in-part of Ser. No. 651,999, Sep. 19, 1984, abandoned.

[51] Int. Cl.$^5$ ................................................ A01N 1/02
[52] U.S. Cl. ............................................ 435/1; 435/2
[58] Field of Search ........................................ 435/1, 2

[56] References Cited

U.S. PATENT DOCUMENTS 4,462,215  7/1984  Kuraoka et al. .......................... 435/1

Primary Examiner—Sam Rosen
Attorney, Agent, or Firm—Malke Leah Bas Meyer; Itzhak Ben Shlomo

[57] ABSTRACT

A unique and novel operative means and method has been designed to successfully procure and sustain biological systems placed in a state of cryogenic suspension. Entire biological systems or their constituent parts are placed in a non-frozen vitrifiable state for a time interval of determinant length in the presence of a non-toxic, protective profusiate, under sustained pressure and temperature approaching or less than the glass transition temperature. The implementation of a substantial regimen of cryoprotectants and baroprotectives within the contexts of a protective profusion solution favorably alters the colligative properties of the said biological systems significantly impeding the process of nucleation. The deleterious process of nucleation, the subsequent formation of crystals and or the critical alignment of said crystals is prevented by the exactation of specific resonate energy fields. The viability of said biological systems are further maintained upon their recovery from cryogenic suspension by a series of unique and novel base profusiates, metabolic stablants and the subsequent application of thermal kinetic parameters to the aforementioned biologicals by thermal induction, microwave lasers and radiofrequency generators.

11 Claims, 25 Drawing Sheets

- Na⁺ SODIUM CATIONS
- Cl⁻ CHLORIDE ANIONS
- • DISSOLVED GASES
- DEFORMATION OF WATER MOLECULES
- DISTORTION OF WATER MOLECULES
- ENLARGEMENT

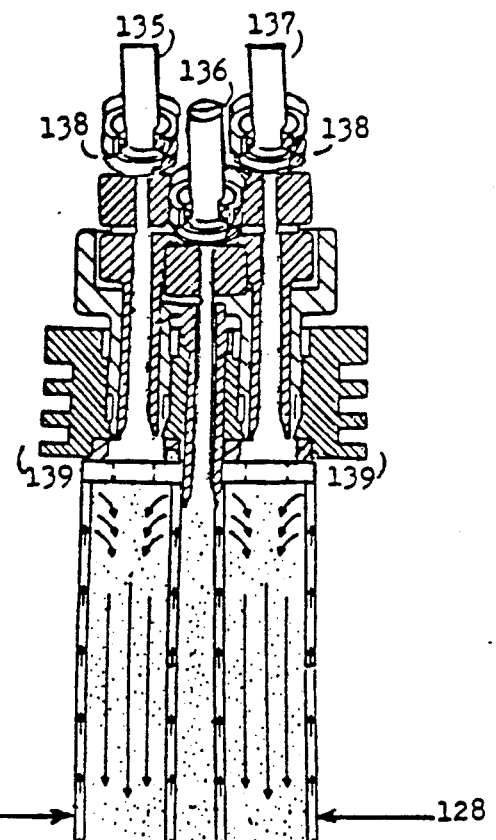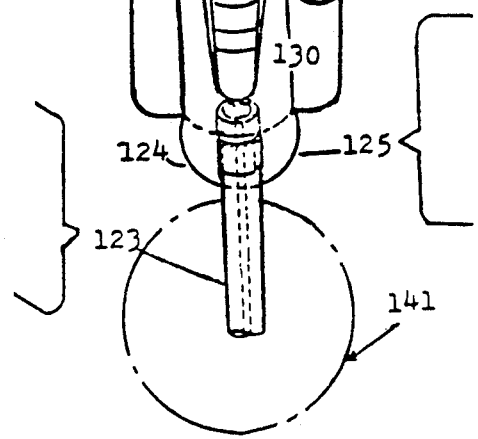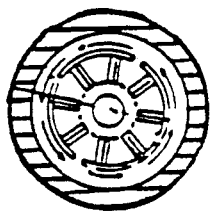

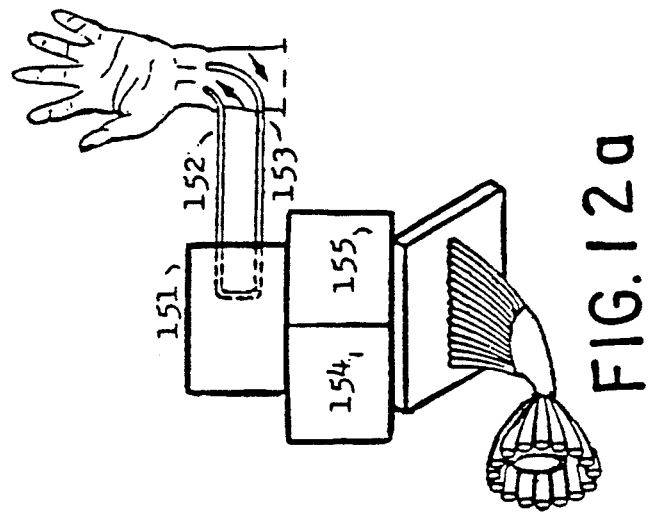

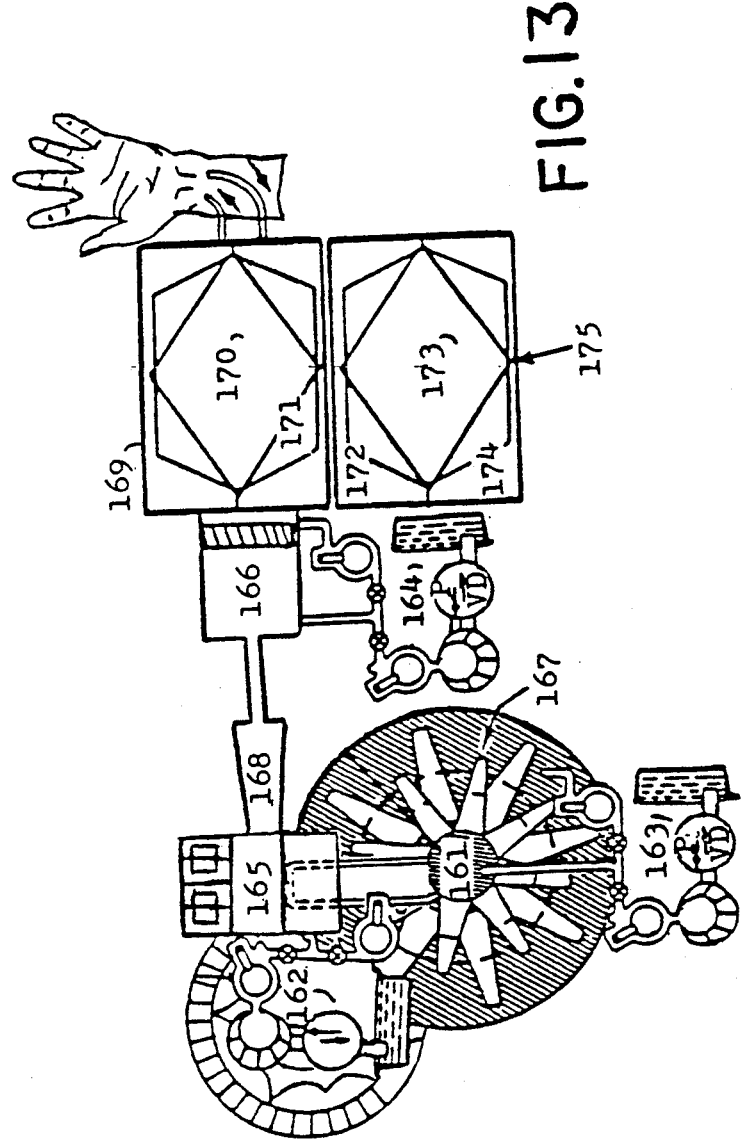

CRYOGENIC SUSPENSION METHOD

This application is a continuation-in-part of Ser. No. 651,999, filed Sept. 19, 1984, now abandoned.

BACKGROUND OF THE INVENTION

1. Field of the Invention

The invention pertains to the utilization of systems and methods deploying the cyclic processes of vitrification for the expressed purposes of placing viable biological systems into a state of cryogenic suspension, the subsequent retrieval of the same said viable biological systems from the state of cryogenic suspension and their reintroduction to ambient conditions of temperature and pressure.

2. Description of the Prior Art

Conventional means of cryogenic preservation have exhibited great promise in sustaining unicellular organisms such as sperm, erythrocytes, various protozoa and multicellular embryonic or fetal systems, detached organs and the like. Significant drawbacks have occurred in attempts to place entire organ systems in a protracted state of cryogenic suspension due to a series of complications arising from intracellular and extracellular damage to chemical and structural biological systems attributed to the formations of crystals at the nucleation temperature ($T_n$) and devitrification. The inadvertant extremes in baropressure and thermal parameters produced by cryogenic suspension often initiates the deactivation of labile enzymes and metabolites, a direct consequence of denaturization. Another potentially lethal consequence of cryogenics are the induced losses in ionic transport mechanism, imbalances in osmotic concentrations and high levels of toxicity due to the accumulation of cryoprotectants and the like compounds.

The aforementioned deficiencies in conventional cryogenic techniques are made evident in the precedings of Farrant (Nature, 205, 1284-87 1965), Fahy and Mac Farlane (20th annular Meeting of the Society of Cryobiology U.K. August 1983 supported by grants GM17959 and BSRG 2 507 RPOS737 NIH American Red Cross), Pierre Boutron (Cryobiology 21, 183, 191 (1984)). The utilization of cryoprotectants with inherent toxicological effects such as dimethyl sulfoxide, devitrification, extremes in temperature, pressure and the complications associated with incurred losses of viable chemicals, ionic transport and or the deactivation of essential enzymes or labile cofactors, which are evident in present techniques of cryogenic preservation. Thus, in recent years there has been a substantial interest in, and the development of effective viable alternatives to the foregoing conventional cryogenic techniques.

Accordingly, it is desirable to provide a method for the successful preservation of organs, tissues and other biological materials at very low temperatures which avoids the formation of ice crystals, minimizes the effective concentration of potentially harmful chemicals; and permits the rapid introduction and removal of cryoprotectants at feasible temperatures, without the necessity of elaborate equipment to monitor precise conditions of concentration and temperature. These advantages are obtained by the vitrification process of the present invention.

The principles of vitrification are well-known. Very generally, the lowest temperature a solution can be supercooled without freezing is the homogeneous nucleation temperature $T_n$, at which temperature ice crystals nucleate and grow, and a crystalline solid is formed from the solution. Vitrifiable solutions have a glass transition temperature $T_g$, higher than $T_n$, at which temperature the solution vitrifies, or becomes non-crystalline solid. Owing to the kinetics of nucleation and crystal growth, it is effectively impossible for water molecules to align for crystal formation at temperatures much below $T_g$.

On cooling most dilute aqueous solutions to the vitrification temperature (about $-135°$ C.), $T_n$ is encountered before $T_g$, and ice nucleation occurs, which makes it impossible to vitrify the solution. In order to make such solutions useful in the preservation of biological materials by vitrification it is therefore necessary to change the properties of the solution so that vitrification occurs instead of ice crystal nucleation and growth. While it is known that many solutes, such as commonly employed cryoprotectants like dimethyl sulfoxide (DMSO) raise $T_g$ and lower $T_n$, solution concentrations of DMSO or similar solutes high enough to permit vitrification typically approach the eutectic concentration and are generally toxic to biological material; further, careful development of such concentrations is necessary to avoid ice crystal formation. While it is also generally known that high hydrostatic pressures similarly raise $T_g$ and lower $T_n$, vitrification of most dilute solutions by the application of pressure is either impossible or impractical. Further, for many solutions vitrifiable by the application of pressure, the required pressures cause unacceptably severe injury to unprotected biomaterials during vitrification thereof; for example, a pressure of only 1000 atm. is lethal to unprotected kidney slices. These and other barriers to cryopreservation of biological materials have not been surmounted in the prior art.

SUMMARY OF THE INVENTION

The scope of the invention resides in the application of cryogenic suspensions with the distinct confines of recursive resonating electromagnetic fields. A regimen of intracellular and extracellular concentrations of cryoprotectants, baroprotectants, antitoxicenogens* and metabolic stablants are administered to specifically after the colligative properties of biologicals that are modified in an exact manner which is conductive to the preservation of cellular integrity and metabolic activity. Wide variances in thermal kinetic parameters are initiated in order to exact the glass transition temperature ($T_g$) wherein a non-crystalline solid state exists in which vitrification occurs while simultaneously avoiding the attainment of the nucleation temperature ($T_n$) and/or devitrification wherein crystallization causing potential biochemical, cellular and subcellular organel structural damage occurs.

*antitoxins which prevent or reverse the mutagenic effects or toxins deleterious to genetic material.

Cryoprotectant are administered in the form of penetrating glass forming solutes which are introduced for the explicit purpose of altering the colligative properties of a specified biological system and in so doing to facilitate the vitrification of the same said system a necessary consequence of the invention. The PGF concentrates consists of but is not limited to dimethyl sulfoxide (DMSO), glycerol, ethylene glycol, propylene glycol 1,2-propanediol and other equivalent substances. As the said PGF substances began to concentrate in given biological systems the elevated concentrations of said cryoprotectants have an innate toxicity which tends to manifest itself by inhibiting and/or otherwise damaging cellular metabolism, chemical structures and the like processes. The inherent, toxicity of PGF infusiates are effectively ameliorated or otherwise obviated with the simultaneous introduction of either high or low level molecular weight non penetrating glass formers (NPGF) consisting of but not limited to compounds of polyvinylpyrrolidone(PVP), hydroxyethyl starch (HES), HAMACCEL, sucrose, proteinoids and/or other colloids. Additionally, antitoxicenogens are provided in the form of other solutes which have the capacity to counter the effects of DMSO which includes the entire spectrum of amides such as acetamide (AA), formamide, glycineamide, sulfamide and urea. A secondary consequence of PGF systems are their innate capacity to act as an enhanced baroprotectant presented in elevated concentrations. In order to exact vitrification and maintains ($T_g$) to the exclusion of the nucleation temperature ($T_n$) the biologicals must be subjected to extremes in pressures ranging from in excess of 100 to 2000 atmospheres; however under sustained pressure there is a tendency for heavier gaseous components to diffuse from the compressed atmosphere interface across the cell membrane proper into the said cellular component media. The cellular component form tissue aggregate which tends to form organs and the heavier atmospheric gases such as nitrogen under extremes in pressure saturated cell bodies form in a precipitous manner large population of miscible gases or bubbles. The formation of nitrogen bubbles in biological systems are especially injurious to the living tissue. The deleterious effects of nitrogen bubbling is effectively eliminated by process of diffusive leaching of the said lethal gases and its immediate subsequent replacement by a non-reactive inert gas such as helium presented in sufficient quantities as to form a displacement medium. ,6 penetrating glass forming(PGF).

Additionally, the aqueous cellular volume is reduced by a factor of between ⅓ and ⅔ of its norm, while simultaneously regulating the isotonicity and osmality of all cellular constituents in accordances with the vitrification/devitrification cycle. The PGF/NPGF regimen is further supplemented with a series of osmotic antagonists such as mannitol to control transitory periods of cellular swelling until the cellular constituents are equilibrated. The devitrification temperature ($T_c$) is elevated with increases in pressure; whereas the liquidus temperature ($T_m$) is simultaneously depressed and the forces governing the motility of exogenous substances into the cellular constituents are greatly enhanced. Since devitrification occurs open rewarming initiating crystallization, the process of devitrification is to be avoided and this is done by rapid increases in the concentration of penetrating solutes/NPGF profusiates, temperatures and pressure. The energetic or kinetic parameters are uniformly altered through a series of heterogeneous cellular constituents by a series oscillatory resonating electromagnetic fields which are propagated on the basis of establishing uniformed and equivalent concentration, kinetic, thermal and pressure gradients throughout the living cellular matrix. Applied sonic temporal field resonance waves or sympathetic vibrations are utilized in a specific manner to prevent the formation of crystals during the nucleation temperature by impeding the intrinsic vibrational or resonant frequency at which crystal formation occurs. The non-crystalline solid vitrification phase is uneffected by the implementation of the sonic resonant field, which disrupts the critical alignment of crystals during the nucleation phase due to the fact that the intrinsic atomic and molecular resonant frequencies for the glassification process is substantially different than the intrinsic resonant frequency encountered by the nucleation temperature. A secondary consequence of the sonic resonance process is the initiation of uniformed agitation on a molecular level, which uniformly distributes the entire regimen of profusiates evenly throughout a given cellular matrix under conditions of dynamic flux.

The excitation of the cellular matrix by magnetic induction, microwave laser resonance and radiofrequency oscillation provides for the rapid uniformed thermal kinetic equilibration necessary so the biologicals can pass from one phase state to another without incurring organic or physical damage. Another direct consequence of the above mentioned excitation process is to actively enhance the motility of exogenous chemicals or profusiates across the cell membrane providing rapid uniformed dispersal of said profusiate through the cellular matrix. Metabolic stablants consisting of but not limited to electrolytes precursors of gluconeogenesis, glycogenesis, phospholipid metabolism and other processes which are continuously replenished from reserves as a necessary consequence of vitrification, devitrification and annealing. The vitrification, devitrification and annealing process inevitably produces incurred losses in electrolytes due to ionic leaching osmotic imbalances due to differentials in concentration gradients and deactivation of various enzymes and metabolic precursors due to dehydration and denaturing.

Subsystems embodied within said cryogenic suspension device unless otherwise indicated are coupled to the CPU, a controller means an array of sensors and a power source.

BRIEF DESCRIPTION OF THE DRAWINGS

FIG. 7 is a detailed sectioned perspective describing one of six equivalent solid state sonic resonators utilized to prevent nucleation and promote the active dispersal of profusiates and the like;

FIGS. 8, 8a and 8b represent a concise pictorial view of one of six equivalent radiofrequency devices which are utilized in the rewarming phase of the recovery period;

FIGS. 11 through 11b are detailed sectioned views of the hypodermic means which is utilized to inject profusiates, metabolic stablants and the like.

FIGS. 12, 12a entail a detailed perspective view and schematic view of a single dialyzer means;

FIG. 13 is a simplified schematic view of the dialyzer complement;

FIG. 14 illustrates in part a simplified version of an electrophoretic laser sensor means utilized to monitor the intrinsic levels of ions, solutes and the like;

DETAILED DESCRIPTION OF THE INVENTION

Figure 1:
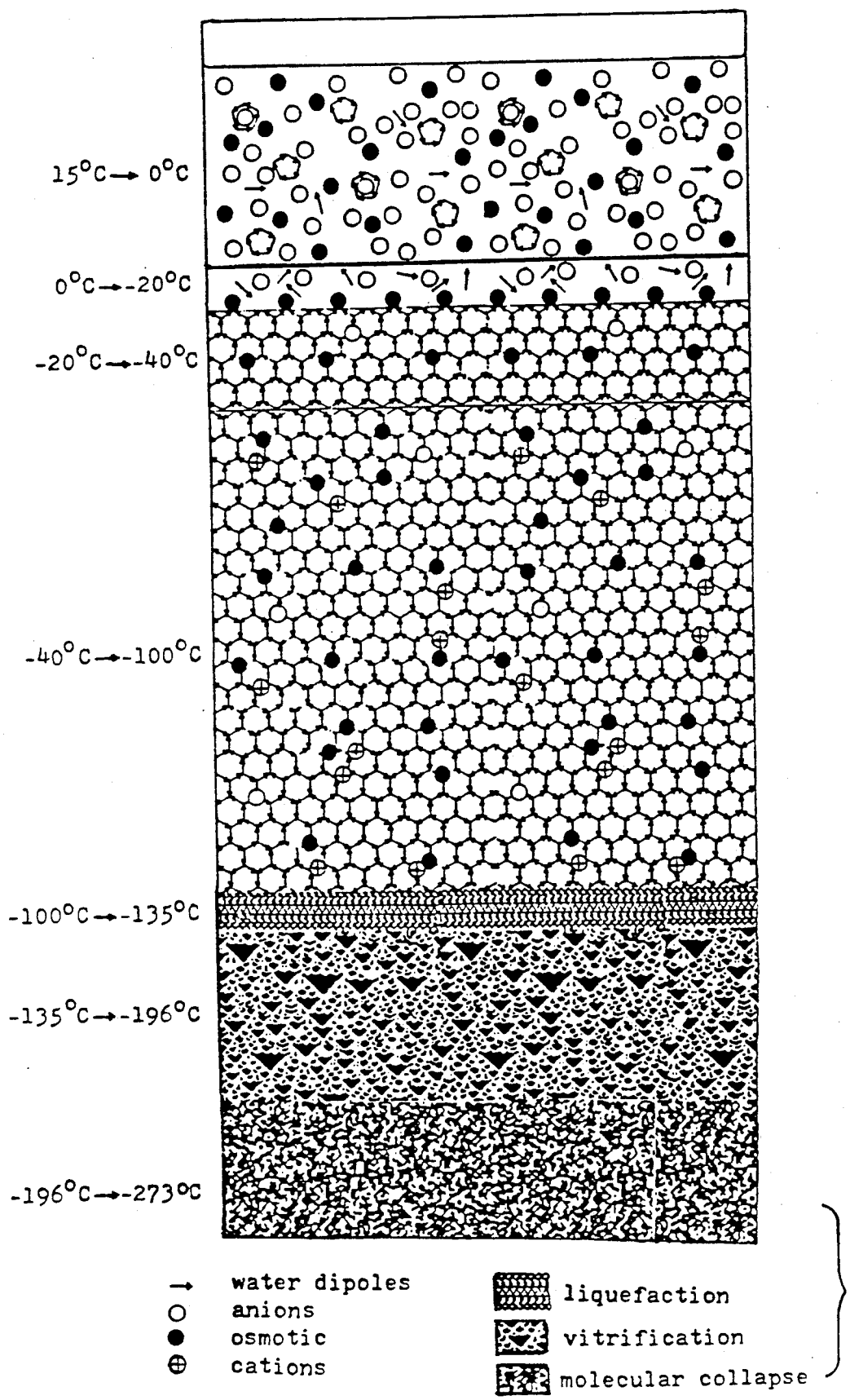
FIG. 1 is a schematic representation illustrating the critical phase transition occurring in a dilute saline profusiate ranging in temperature from 15° C. to well under −200° C.

The vitrification procedure contained within the scope of the invention consists primarily of placing the vitrifiable biological media into a closed system pressurized chamber or solid state capsule. The biological is then suspended and totally immersed in a non-toxic, non- adhering profusion medium, wherein the ambient temperature falls within 0° C. to 10° C. Suitable cryoprotectants penetrating glass forming solutes (PGF) are introduced and consist of but is not limited to dimethyl sulfoxide (DMSO), glycerol, ethylene glycol, propylene glycol, 1,2, 1,3-propanediol which are introduced in gradual increments as the pressure is gradually increased and the temperature is simultaneously decreased. The penetrating glass forming solutes (PGF) when administered or otherwise introduced by profusion* of organs and/or carrier mediated substances are intrinsicly toxic in higher concentrations and in order to compensate or ameliorate the toxicity of PGF systems a full regimen of non-penetrating glass formed (NPGF) are simultaneously introduced to the biological system. NPGF antitoxicenogens consist of but is not limited to polyvinylpyrrolidone, hydroxylthyl starch (HES) HA-EACCEL (obtained from Hoechst Pharmaceuticals) various proteinoids, sucrose or other colloids. Additionally, the intrinsic or innate toxicity of DMSO can be effectively countered in a compensatory manner by amides such as acetamide (AA), formamide, glycineamide, sulfamide, urea and numerous commerically available membrane and protein stablizers. Actually the perfusion of organ systems, the equilibration of tissues is accomplished prior to subjecting the biologicals to extremes in pressure within a closed system.
*the term perfusion is equivalent to the term profusion The cellular volume of the constituent cells are similarly uniformly reduced from ⅓ to ⅔ of the normal volume, with the intracellular solute concentration effectively maintained at not less than 30 (thirty) percent and the cells are brought below their ambient isotonic volume prior to vitrification. The reduction of cellular volume invariably increases the intracellular protein concentration by a significant degree in order to effectively reduce the amount of penetrating glass-form needed for intracellular vitrification. All substances unless specified otherwise are available commerically and well known to those skilled in the art. Protocols governing the implementation of concentrational increments over durational perfusion intervals are applicable to said procedure as the criteria defined by Lerein, Pegg, Segal and/or similar such techniques described by others in the field.

Additionally, the pressure to which the biological systems are subjected to increases by rapid increments taken in succession to the optimum vitrification pressure, the temperature is simultaneously lowered to approximately 5° C. below the glass transition temperature ($T_g$) and the subsequent displacement of baroreactive ambient gases deleterious to biological systems. The glass transition temperature, $T_g$, is the temperature at which a solution attains a non-frozen vitrified state. The glass transition temperature, $T_g$, is a non-crystalline solid state wherein an extreme elevation in intrinsic viscosity is produced by the cessation of translational molecular motions. The nucleation temperature, $T_n$, is the temperature at which crystals nucleate and form aggregates, precipitating crystalline solidification of usually an aqueous solution. Typically, the nucleation temperature is avoided at all costs because of the elicit chemical and structural damage incurred by cell membranes and intracellular organels as a direct consequence of physical or spatial distortion initiated by the crystallization process. The rate at which the pressure is raised and the extent to which the pressure is elevated is of prime importance in order to either prevent or minimize the potentially toxic effects of the glass-forming solutes and any induced baroinjury.*[1] The rates of pressurization range from 500 to just under 2000 atmosphere per square cm per minute and upon reaching the final temperature the pressure is subsequently released. Protracted storage may have a ambient vitrification temperature of $T_g$ minus 15° C. or approximately −196° C. depending on the difficulty of evading crystallization and vitrification.*[2] Complications arise in the rapid pressurization and cooling of both homogeneous and non-homogeneous biological in regards to chemical equilibria and uniformed temperature and pressure gradients. Certain ambient atmospheric gases such as nitrogen must be leached out of the biological sample media and are replaced by some non-reactive inert gaseous substitute such as, helium prior to vitrification. It has long been known that improper decompression can cause the formation of nitrogen bubbling in the circulatory system of divers and that the same said organic life forms can sustain greater pressure for protracted periods of time, breathing a mixture of heliumnated gases rather than a combination of ambient gases found at the planetary surface. Experimental evidence indicates that under great extremes in pressure the gaseous atmospheric component of nitrogen begins to concentrate to the point of supersaturation in the intracellular compartments of the cellular matrix forming a given tissue or organ system. The accumulated nitrogen gases become effectively trapped under the cryogenic condition and eventually manifests itself in the form of a precipitous deleterious bubbling phenomenon when the pressure is released. The functional displacement of atmospheric nitrogen by helium or its equivalent while simultaneously leaching the nitrogen component out of the atmosphere prior to pressurization and the vitrification process effectively obviates the potentially lethal effects of nitrogen gas bubbling in the intracellular medium when the biological system is taken out of cryogenic storage or suspension and or rapidly depressurized.

*1 to either prevent or minimize baroinjury and avoid the potentially toxic effects of the higher concentration of glass-forming solutes required for vitrification at one atmosphere.
*2 Tg depends on what the concentration of cryoprotective agents are. Tg should be about $-135°$ to $-150°$ C. with current cryoprotective protocols. Storing material just below Tg (below $-196°$ C.) may help avoid vitrificative. The danger of crystallization is in using too slow a cooling rate or too slow on the warming rate, which would allow nucleation.

Further complications are elicited by the effects of cryogenics and are extreme in baropressor, temperature, imbalance in electrolytes, osmotic and ionic concentration on the viability of of biological systems. As previously established, the reduction of isotonic cellular volume and the introduction of cryoprotectants ultimately alters the colligative properties of the intracellular solution. Antitoxicinogens administered in the form of high and low molecular weight NPGF counter the toxic effects of the cryoprotectants presented in substantially high concentrations. Similarly the deleterious effects of temperature and pressure on enzymes, their precursors and key metabolites involved in gluconeogenesis, glycolysis, phospholipid metabolism and the like process must be alternately compensated for in order to maintain biological viability. Extremes in pressure and temperature often denatures complexed proteins responsible for catalyzing enzymatic reactions deactivating the said enzymes or other labile, important biological substances such as co-enzymes (vitimains, especially ascorbic acid and the B complexes) and metabolites. The introduction of metabolic stablants either prior to or after vitrification such as during the annealing process or during the biological systems reintroduction to standard conditions of temperature and pressure S.T.P. which is approximately 300° K. to 325° K. 760 mm, or some equivalent conducive to biological activity. Metabolic stablants are defined as those ions or organic complexes conducive to the maintenance and propagation of necessary metabolic processes needed to sustain and perpetuate biologically active systems.

The metabolic stablants are critical additives which must be immediately administered to a biological system upon its reintroduction to ambient conditions of temperature and pressure, which usually corresponds from between $-5°$ C. to 37° C. and from 740 to 760 mm of pressure. The metabolic stablants are introduced by either profusion of organ systems, mediated carrier transport, or other techniques well known by those skilled in the art. Thermal and barosensitive enzymes such as, expended ATPase Mg $Cl_2$, ATPase.$Ca_2$. ATPase-$Ca_2$, phospholipase, transaminase and the like must be immediately replenished once the biological systems are reintroduced to ambient conditions in order to evade wide spread starvation on a cellular level. Additionally, labile coenzymes and cofactors must be replaced such as vitamins and minerals introducted to the biological system at its maximum tolerance levels as per USRDA unless specified otherwise. Complexes of sodium citrate, potassium citrate at 27.5 mM Equivalents and ionic equivalents of sodium, potassium, magnisium, calcium and a host of other electrolytes. Additionally cellular structures are stabilized by the introduction of minute quantities of anti-inflammatory such as, dezamethasone ($100+\mu M$) hydrocortisone (3–10 mM), or an equivalent. Further metabolic supplements such as, dextrose, dextran, sulfate, sodium and a series of antioxidants; which provide cellular structures with additional stablization attribution to chlorpramazine 0.5 mM, chloroquine 5 mM and indoleacetic acid 0.5 mM.

The subsequent supplementation or replacement of heat or pressure labile vitamines, enzymes and cofactors is of primary importance in order to maintain and propagate biological activity of a given system recovering from cryogenic suspension. Vitamin A (provitamin A carotenoid exerts an influence on glycogen neogenesis and cellular division. Choline a member of the B Complex enhances the mobilization of fatty acids, stimulates phospholipids and facilitate the production of acetylcholine. Biotin apparently acts as a coenzyme in the carboxylation of pyruvate to oxalacetate. Folic acid apparently operates metabolically with ascorbic acid and is involved in amino acid metabolism and is essential to the formation of labile methyl groups acting with $B_{12}$ to stabilize the metabolism of reactions involving labile methyl groups. Inosital appears to act in the formation of cephalens, para-aminobenzoic acid apparently acts as a mediator or carrier means and nicotinic acid plus other coenzymes which effects the local retention of water. The addition of Thiamine ($B_1$) prevents fluid retention in cardiac tissues and in the phosphorlated form such as, co-carboxylase, which is enzymatically active in the oxidation of glucose involved in oxidation decarboxylation of pyruvic acids. Vitamin C ascorbic acid (50 mg) is specific detoxification process, metabolizing phenylalanine and tyrosine and cellular metabolism acting as an oxidation reduction catalyst and providing for the regeneration of collagen. Vitamin D in the presence of calcium ions appears to be responsible for the necessary absorption of fatty acids. Vitamin E $\alpha,\beta,\gamma$-tocopherol is an extremely important anti-oxidant nullifying the formation of free radicals which occur due to alterations in pH, extremes in pressure and temperature, and also appears to be important in muscle metabolism, countering the effects of accumulated lactic and pyruvic acid retention on subcellular compartments during the vitrification and rewarming cycle. Vitamin K, a naphthoquinone is introduced by a fat soluble carrier and initially acts as a respiratory enzyme facilating electron transport and phosphorylation. Minerals are co-factors present in trace elements which are responsible for the maintenance of pH at biological limits, maintaining cellular functions when coupled enzymes or their precursors and the maintenance of osmotic pressure. Zinc enters into the structure of the carbonic anhydrase enzyme, lactic dehydrogenase and peptidase. The applicability of calcium and magnesium as critical cofactors, or catalysts activating enzymatic reactions (i.e. ATPase $MgCl_2$ in intracellular metabolic processes. Cobalt appears to be an enzymatic activator and is a critical part of vitamin $B_{12}$. Iodine is a key element in the manufacture of thyroxine which is a necessary precursor involved in the metabolism. Iron functions as an intermediate transport carrier of oxygen in the heme complex and is a buffering agent.

Additional anti-oxidants, buffers, detoxifiers and the like are profused, transported by a molecular carrier means and/or otherwise infused into biological systems upon their recovery from cryogenic storage and subsequent re-entry into an ambient environment. Anti-oxidants such as butyl hydroxy toluene (100-200 ug/V) in alcohol and or glycerol, Coenzyme Q10/ in 80 ug/V, Glutathione 5 grs. per litter, 2 methyl butane milimolar volume and a promising new synthetic, Selenium Methionine $10^{-12}$ molar; which appears to reverse potentially deleterious effects of free radical formation. Monosodium Aspartate and monosodium glutamate stimulates mitrochondrial activity. Selenium Methionine has a secondary function, acting as a detoxifier for DMSO and is commerically available. Further, carrier solutions composed of dextrose and/or extracellular solutions high in $K^+$ and $Mg^{+2}$ are a direct factor in reducing the toxicity of cryoprotectants. Ionic concentrations of sodium, potassium, chloride and the like are re-added to biological systems, which are rehydrated upon their emergence into an ambient environment from cryogenic storage.

The ultimate goal of cryogenic suspension is to preserve the viability of one or several intact biological systems for an indefinate period of time so that the aforementioned organic systems can re-enter or re-emerge into a comparable, or equivalent environment, from where the same said biological had originated. Experimental evidence indicates that the cooling rate is inversely proportional to the amount of absolute pressure required to vitrify a given solution such that, increasing the cooling rate from approximately 10° K. per minute (10° K. minute$^{-1}$) to about 100° K. per minute decreases the vitrification pressure (VP) by a mean value equivalent to 100 atmospheres per the average or mean solution. Further experimental evidence indicates that vitrification pressure (VP) is directly proportionate to the vitrification concentration (VC) and the manipulation of the cooling rate will permit the said vitrification concentration (VC) and/or vitrification pressure (VP) to vary accordingly. Increments in (VC) while favorably altering the colligative properties of biologicals proportionately increase the toxicity of the organic system. The (VC) can be reduced by a significant degree by increasing the rate of cooling and stabilizing or holding (VP) in a steady state. If baroprotection is decompensated or the (VP) is incomplete the cooling rate can be increased and the (VP) lowered maintaining viability of the biological system. Devitrification ($T_c$) the reformation of crystals incurred by a biological system emerging from cryogenic suspension can be effectively eliminated by increasing the rate of warming, increments in pressure and increases in the concentration of the vitrifiying solutions. An exemplary experimental varification of parameters elluded to in the aforementioned statement is as follows. The application of pressure equivalent to 1900 atmospheres elevates the devitrification temperature, $T_c$, by 30° C. and warming rate of between 200° C. to 300° C. per minute which effectively impedes or entirely eliminates the probability of incurring devitrification by a factor of 100. Further, the administration of appropriately high concentrations of PGF associated with the simultaneous presentation of NPGF significantly reduces the warming to approximately 100° C. per minute rather than necessitating the need to implement a procedure which elicits increases in the warming rates of 200° C. to 300° C. per minute in order to avoid encountering the devitrification process (ordinarily tissue cooled below −20° C. can sustain 1.9K bars for a period of 10 to 15 seconds without appreciable damage) in treated tissue, tissues devoid of PGF failed to tolerate 685 atmospheres (10,000 psi); whereas tissue treated with 30% W/V DMSO or 30% W/V DMSO+PG were undamaged at 1030 atmospheres, but failed to tolerate 23,000 psi without alterations in temperature.

Further, the electrolytic balance, isotonicity, osmotic levels and the like are reinstated upon re-establishing the aforementioned condition of ambient condition of standard temperature and pressure (300° K. and approximately one atmosphere 760 mm). Ideally, a base profusiate is infused along with an appropriate concentration of electrolytes, as the concentrated regimen PGF/NPGF and the like are removed and the biologicals are restored to their said ambient norms. Electrolytic balances of catons ($Na^+$, $K^+$, $Ca^+$, $Mg^{+2}$) and anions ($Cl^-$, $H PO_4^{-2}$, $HCO_3^{-2}$) are returned to their initial norms and equilibrated in accordance to normal cellular functions, concentrations, chemical composition and the like of the base profusiate are briefly described in part in the tabulated form presented herein below:

| component | BASE PROFISIATE | | |
|---|---|---|---|
| | grams/liter | Moles | M. Mt. |
| KCl | 2.10 | 0.28 | 74.6 |
| $K_2HPO_4$ | 1.26 | 0.0054 | 212.3 |
| $NaHCO_3$ | 0.84 | 0.010 | 84.0 |
| Sodium Glycerolphosphate | 6.36 | 0.027 | 236.0 |
| $MgCl_2$ | 0.406 | 0.0043 | 95.2 |
| $CaCl_2$ | 0.111 | 0.001 | 111 |
| Dextran 40 | 50.00 | 0.001 | 40K polymers |
| Dextrose | 2.00 | 0.011 | 180 |
| Mannitol | 21.42 | 0.118 | 182 |
| Glucose | 1.80 | 0.0103 | 174.1 |
| L-Glutathione | 1.54 | 0.0050 | 307.3 |
| HEPES | 1.72 | 0.0302 | 238.3 |
| Adenine HCL | 0.17 | 0.001258 | 135.1 |
| HES | 60.00 | 0.006 | 10-100K polymer |

The optimum techniques or best mode procedure consists of immersing the biological systems in an aqueous ice solution or its equivalent in order to drop the said biologicals to within 10° C. The ambient temperature is maintained at 10° C. as the aqueous solution is gradually withdrawn to be immediately replaced by a dilute vitrification solution (10% to 25% per W/V); wherein equilibration occurs and the temperature is lowered to 0° C.±2° C. Additionally, the ambient atmosphere is purged or carbon monoxide, oxides or nitrogen and sulfide, molecular nitrogen and the like gaseous atmospheric component which would otherwise be lethal to organic systems, due to irreversible binding or the formation of deleterious bubbles. Gases such as molecular nitrogen are replaced with inert gases such as helium which does not combine with biologicals or form deleterious bubbles upon either rapid atmospheric compression or decompression. In any event any and all potentially lethal gases are removed prior to vitrification. The concentration of the vitrification solution is immediately increased in a single step from approximately 35% to 50%, until the cellular matrix becomes vitrifiable. The isotonic volumes of the same said cells forming the cellular matrix of the biological system is reduced by $\frac{1}{3}$ to $\frac{2}{3}$ their original ambient levels. If entire organ systems are intact they must be not only suspended in a non-adhering neutral solution, but have undergone profusion prior to being subjected to extreme pressure as soon as the said biologicals are sufficiently equilibrated to attain vitrification. All biologicals are placed in a pressurization chamber, wherein the pressure is immediately raised from between 500 to 2000 atmospheres and the temperature is simultaneously lowered as fast as possible to below $-130°$ C. to $-145°$ C. (Excessive cooling must be prevented in order to avoid fracturing of the glass). The pressure is slowly released and the system is cooled at a rate of less than but no higher than 0.5° C. per minute incorporating in some instances a period of annealing at $-140°$ C. which is required in order to permit the fictive temperature to reach the holding temperature and consequentially relieve cellular stresses providing structural deformation. Cooling is preferably conducted in a elastic container lined with a cryogenic resistant teflonated or without a container other than a coat of glass (CP) enveloping the biological system. A series of sonic field generators provide resonant frequencies which impede the nucleation formation and alignment of crystals at the nucleation temperature; which would otherwise disrupt the intracellular network of cytoplasmic tendrils, intracellular organels, membranes, chemical structures and the like. The application of sonics at given characteristics resonant frequencies also effectively facilitate the transport and equilibration of glass forming penetrators, non-glass forming penetrators, metabolic stablants and other factors with cellular matrix. Storage of the biologicals should be conducted and maintained at temperatures between $-150°$ C. and $-200°$ C. The retrieval process wherein a biological system from storage is warmed very slowly to near the transition glassification temperature ($T_g$) and to repressurized if necessary, than warming as rapidly as possible to temperatures approaching the ($T_m$) via microwave, thermal induction and radio-frequency means when necessary. (It is imparative to note that rapid increments in uneven or insufficient thermal conductance will eventually result in the fracturing of the said glass). The system upon reaching 0° C.$\pm$10° C. is immediately profused with or diffused with a 15% to 30% W/V solution of PGF plus increments of metabolic stablants and osmotic antagonists such as, mannitol utilized to control osmotic swelling as the pressure is released and ambient conditions are nearly re-established.

The vitrification solutions which have so far through experimentation been found to operate in an exemplary fashion are consistant with multiple proportions of PGF and NPGF. Mixtures of 17.5% W/V DMSO, 17.5% W/V propylene glycol and 6% W/V PVP ($\epsilon$=41% W/V) have a tendency to form doubly unstable glasses in which the nucleation temperature $T_n$ is higher than the glass transition temperature $T_g$ at one atmosphere. Mixtures containing multiple proportions of approximately 12.8% W/V DMSO, 12.8% W/V propylene glycol, 19.4% W/V acetamide (AA) and 6% W/V PVP total concentration ($\epsilon$=51% W/V) are exceptionally stable such that no devitrification is observable during conditions of one atmosphere, warming increments of 5° C./minute and in the absence of pressure extremes in most instances, since no pressurization is required for vitrification. Concentration of between 46% and 49% of DMSO, PG, AA and PVP are usually more than adequate for most organ systems. Solute systems comprising approximately 18.22% W/V DMSO, 13.78% W/V acetamide, 10.00% W/V propylene glycol and 6.02% W/V PVP-K 30 dissolved in an appropriate base solution. The concentration of DMSO and acetamide may vary proportionately from 25% W/V to 35% W/V depending on the pressure and the concentration of PG and PVP.

Prior to attaining vitrification the biological systems must be purged of any atmosphere components which are or otherwise would be rendered noxious or fatal to the said systems due to extremes in pressure or temperature. Each said biological system should be construed as being essentially a biological solution. Favorable diffusion gradients and strong molecular binding properties of such molecular gases as carbon monoxide, cyanogens, oxides of nitrogen and the like are essentially purged from the cellular matrix of the system and the atmosphere surrounding the said matrix. Other gaseous mediums such as, nitrogen which tend to concentrate as extreme pressures are applied (500 to 2000 atm.) and then to bubble in a deleterious manner upon rapid decompression are also purged or otherwise eliminated from the atmosphere surrounding the biological systems. The kinetics involved in the liquefaction of gases and or induced bubbling of said gases are specific property of the aforementioned gases under specific conditions. The kinetic parameter for molecular nitrogen are very different than those of helium, for example the critical temperature and critical pressure for molecular nitrogen is $-147°$ C. and 34 atmospheres, whereas the liquefaction of helium occurs at $-268°$ C. and 2.3 atmospheres. The diffusion rate for the aforementioned gases is essentially contingent on the square root of their respective masses which is essentially proportional to ratio of the said gases. Unlike other methods or cryogenic preservation potentially deleterious gases are eliminated from both the system and the atmosphere surrounding the said system. As previously mentioned in the foregoing disclosure deleterious gaseous atmospheric components comprising a high percentage of the ambient atmosphere such as molecular nitrogen is replaced by an inert gaseous substitute like helium prior to vitrification in order to maintain an acceptable partial pressure. The transfer of gases across a liquid gas interface separated by a cellular membrane is clearly illustrated by the concise equation contained herein below, wherein chemical reactions involved are at least an order of magnitude faster than diffusion. The diffusion of gases as far as mass transfer is concerned is considered to be homogeneous through the system and the total area for transfer, S, is known.

$$\int_{\text{o-lim.}} \Sigma \dot{V}_g = \Sigma_g \left( \frac{1}{\frac{P\Delta z_g}{D_{Ag}S} + \frac{\phi z_m}{D_{AM}S} + \frac{CH^*\Delta z_l}{D_{AL}S}} \right) \Delta p_g$$

where
P = total pressure
$\Delta z_g$ = gas film thickness
$D_{Ag}$ = diffusivity of oxygen in the gas phase
S = total area for mass transfer $\phi$ = membrane distribution coefficient
$Z_m$ = total membrane thickness
$D_{AM}$ = diffusivity of oxygen in the membrane
C = total molar concentration of blood substitute
H* is the local prevailing equivalent of Henry's law H

| mass transfer coefficients | |
|---|---|
| $k_g = D_{Ag}/\Delta z_g$ | $k_g a = D_{AG} S/\Delta z_g V$ |
| $k_m = D_{Am}/z_m$ | $k_m a = D_{Am} S/z_m V$ |
| $k_l = D_{Al}/\Delta z_l$ | $k_l a = D_{Al} S/\Delta z_l V$ |
| $\dot{V}_g = kaV\Delta p_g$ | $\psi_i = P, \phi, \text{ or } CH^*$ |
| $ka = 1/\Sigma \psi_i/ka_i$ | $ka_i = k_g a, k_m a, k_l a$ |

The diffusion rates of all gases, their molecular binding capacities, and other properties are well known by those skilled in the art.

The vitrification of the cryoprotective solutions in accordance with the invention occurs at a critical point of concentration of the vitrification medium (VC) which varies inversely with the pressure applied to the protective solution, that is to say the vitrification concentration of a protective solution that is applied is necessarily reduced significantly upon the application of increased hydrostatic pressure. The aforementioned inverse relationship between the vitrification medium and the application of pressure can best be described in an exemplary manner By the following equation contained herein below the said equation yielding a reasonably accurate first approximation.

$$\int_{o \to \lim}^{init. \to 1} (VC)(dc_i/dx) \propto \left[ \left( \frac{(VP)nRT}{(VC) - (x)} \right) \left( \frac{P_2 V_2}{P_1 - vpi} \right) \right]$$

where
(VC) = the vitrification concentration
(VP) = the vitrification pressure
$(dc_i/dx)$ = reaction rate
n = a molar fraction of gaseous medium
n = PV/RT = the contribution of ideal gases at ideal condition
V = nRT/P atmospheric volumetric contribution
R = a constant 0.082 liters atmosphere/°mole
T = °K. at point of vitrification $$\left( \frac{P_2 V_2}{P_1 - vpi} \right)$$

is the contribution of pressure increments $P_2$ over the initial pressure $P_1$ vpi is the contribution otherwise due to incomplete gaseous vapor and the like prior to liquefaction of gases.

The effect of a decline in temperature upon the vitrification pressure VP of a given biological solution is inversely related as exemplified by the concise simplified equation contained herein below which yields a reasonably accurate first order approximation of the said process, $$\int_{o \to \lim}^{init. \to 1} VP(dx/dt) \propto \left[ \left( \frac{T_2 VP}{T_i} \right) \left( \frac{nRP_2}{P_1 - vpi} \right) \right]$$

where
(dx/dt) is the rate of consolidation of the vitrification solution per an interval of time
$T_2$ = decline in temperature
$T_i$ = initial temperature
VP = vitrification pressure
$nRP_2/P_1$ is the contribution of the liquideous gases.

The inclusion of some very concise preliminary experimental evidence of the inverse relationship between vitrification concentration of penetrating glass formers (PGF) mixtures of PGF and combinations of PGF and NPGF are summarily included in part in a tabular form contained herein below;

| PREVENTION OF CRYSTALLIZATION AT ONE AND 1000 ATM[1] | | | | |
|---|---|---|---|---|
| | CRITICAL CONCENTRATION TO VITRIFY AT | | | |
| PENETRATING | ONE ATM | | 1000 ATM | |
| GLASS FORMERS (PGF) | moles 10 moles | % w/v | moles 10 moles | % w/v |
| Ethylene glycol | 3.2 | 55 | 2.6 | 49 |
| 1,3-Propanediol | 2.9–3.1 | 56–58 | — | — |
| Glycerol | 2.7 | 65 | 2.3 | 60 |
| DMSO | 2.1 | 49 | 1.8 | 45 |
| 1,2-Propanediol (PG)[2] | 1.8 | 43.5 | 1.4 | 38.5 |
| 2,3-Dihydroxy-butane | 1.7 | 46 | — | — |
| Trimethylamine-acetate (TMAA) | 1.1 | 41 | ~0.86 | ~36 |
| Dimethylamino-ethylacetate | 1.0 | 45 | ~0.88 | ~42 |
| PGF MIXTURES | | | | |
| DMSO + urea (3 g:1 g) | 3.0 | 59 | ~3.6 | ~55 |
| DMSO + acetamide (DA) (1 mole:1 mole) | 2.8 | 53 | 2.3 | 48.5 |
| DA + PG (1 g:1 g)(DAP) | ~2.3 | ~50 | ~1.9 | ~45 |
| DMSO + PG (DP) (1 g:1 g) | 1.9 | 46 | 1.6 | 42 |
| MIXTURES OF PGF AND NON-PENETRATING GLASS-FORMERS (NPGF) % (w/v) | CRITICAL CONCENTRATION TO VITRIFY AT | | | |
| | ONE ATM | | 1000 ATM | |
| | moles 10 moles | % w/v[3] | moles 10 moles | % w/v[3] |
| DA + 6 PVP | 2.2 | 45.5 | 2.0 | 42.5 |
| DMSO + 6 PVP | 2.0 | 46 | 1.5 | 41 |
| DAP$_{10}$[4] + 6 PVP | 2.2 | 46 | 1.8 | 40 |
| DAP$_{10}$ + 8 PVP | — | — | 1.7 | 39 |
| DAP$_{10}$ + 6 HES | 2.4 | 49 | 1.8 | 42 |
| DAP$_{10}$ + 6 Trehalose | — | — | — | ~43 |
| DAP$_{10}$ + 6 Sucrose | ~2.3 | ~47 | 1.9 | 42 |
| DA + 6 Sucrose | 2.5 | ~49 | 2.2 | 45 |
| DA + 6 HES | 2.5 | 50 | 2.0 | 44 |

[1] Determination made on bulk (8 ml) samples cooled at approximately 10° C./min to $T_g$.
[2] Concentration needed to vitrify at 1200 atm equals 30% w/v.
[3] % w/v of PGF (not including amount of NPGP in mixture).
[4] DMSO + acetamide (1 mole:1 mole) plus 10% w/v PG.

The profusion process unless specified otherwise entails the complete and rapid removal of all blood circulating through a given organism or organ system and its subsequent immediate replacement with either a base profusiate or its equivalent. Prior to vitrification and upon the return of a biological system from cryogenic suspension to ambient conditions the organ or organism is purged entirely of blood, while the base profusiate is administered. The organ or entire biological system undergoes profusion by a dilute base profusiate solution which was previously mentioned in the foregoings as the temperature is decreased from 2° C. to 4° C.±0.5° C., until the system is equilibrated at a standard pressure and the electrolytic balance is normalized by hemodialysis. The biological system is sustained in a bloodless state for a determinant time interval (four hours to several days), until the necessary provisions are made for the said system to re-enter ambient conditions (STP) of standard temperature and pressure alluded to earlier in this disclosure. Further the blood obtained from the said biological system is carefully dehydrated and crystallized in a manner conductive to rehydration at a later date, such that the aforementioned biological system can successfully undergo reprofusion with its very same reconstituted blood. The process of administering base profusion, blood profusion crystallization and reprofusion is a unique and novel implementation of this invention not present or expounded in other processess of cryogenic preservation. Further, when entire organ system or multiple systems are retrieved from cryogenic suspension, a novel regimem of anti-shock agents are administered which consist of but not limited to adrenocorticotropic hormone, (ACTH), Somatotropic hormone (STH), Epinephrine, $\beta$- Endorphin, Enkephlen and globulins (specifically gamma globulin). The said anti-shock preventatives apparently serve to fortify the entire organism against the trauma and to expedite recovery of said organism during the transitory period of re-entry wherein normalization occurs.

Thus far only a cursory explanation of how oscillatory fields prevent the formation of crystal nucleation, exact the uniformed dispersal of chemical species profused throughout a given biological system and the rapid uniformed equilibration of temperature and or pressure parameters needed to achieve vitrification; or to reintroduce the same said biological system to ambient conditions upon its subsequent retrieval from cryogenic suspension. Energy excitation field operates on biologicals and the like by altering their intrinsic energetics, which effects kinetic parameters that govern the aforementioned systems. Biological solutions often initially exhibit a water ice interface phenomenon in the presence of a dilute alkali-halide profusiate.

FIG. 1 is illustrative of a schematic representation of a typically aqueous ice water interface, which is in close proximity to a dilute saline profusiate. The phase transition levels are subdivided into seven critical temperature ranges. The kinetic motions and the relative dispersal rates of some weak solutes are presented pictorially as a function of temperature ranges. The biological solution exhibits liquidity and appreciable molecular motion at a temperature range of 15° C. to 0° C. Molecular mobility becomes significantly arrested at the temperature range of 0° C. to −20° C. Widespread nucleation and crystalline alignment will take place within the temperature range −20° C. to −40° C. unless (PGF) base profusiates alter the colligative properties of said solution. At a temperature range of −40° C. to −100° C. widespread solidification occurs with a tendancy for some dissolved gaseous components to undergo liquedifaction. Liquedifaction of gases begins to predominate, as the biological solution approaches vitrification between −100° C. to −135° C. The said biologicals typically achieve uniformed vitrification at temperatures ranging between −135° C. and −196° C. As the temperature range is brought to under −196° C. the biological structure tends to undergo a bizarre collapse and the dipole medium exhibit a behavior similar to a super-conducter and absolute molecular motion appears to be virtually arrested.

The thermal properties of biological solutions or substrate as those incorporated into the cellular matrix are not decisive factors in the nucleation or the procurement of crystallization; but rather it is the nature and structure of the biological substrate (i.e. bonding polar/-nonpolar interactions), which predisposes crystalline formation, growth rate and alignment. The rate of supercooling the forementioned biological is significant in the growth rate of the crystallization process, as briefly illustrated in the greatly simplified equation contained herein below.

$$V = a (\Delta t)^n \text{ cm/sec}$$

n is another constant and t denotes the growth time. Further, the thermodynamical parameters associated with the normal growth or nucleation of crystal, as opposed to the inhibition of the said process is constantly different when intrinsic vapor pressures are considered.

The thermdynamic parameters are best illustrated by a series of simplified equations well known by those skilled in the art and exemplified herein below:

The vapor pressure of a macroscopic amount of liquid water is given (Clausius - Clapeyron) expression $$p_1 = p_o\left(1 + \frac{\Lambda}{RT_o^2} \delta T\right)$$

where $p_1$ and $p_0$ are the vapor pressures of the liquid at $T_0+\delta T$ and $T_0$, and $\lambda$ is the molar heat of vaporization. A crystal that grows normally (e.g., an ice crystal of infinite dimensions) has a vapor pressure as equivalent to:

$$P_{cr,a} = p_o\left(1 + \frac{\Sigma}{RT_o^2} \delta T\right)$$

where $\epsilon$ is the molar heat of sublimation. For a crystal of microscopic dimensions (edge of cube=a) it can be shown that its vapor pressure is larger than that of an infinitely large crystal $$P_{cr,a} = p_o\left(1 + \frac{\Sigma}{RT_o^2} \delta T + \frac{4\gamma_{cr,1}}{aRT} \frac{M}{\rho_{cr}}\right)$$

where $\gamma_{cr,1}$ is the free energy of the crystal-liquid interface, M the molecular weight of the substance ($H_2O$), and $\rho_{cr}$ the crystal density. If $P_1 = P_{cr,a}$ *then the freezing point lowering* $\delta T_a$(°C.) as follows:

$$\delta T_a = -\frac{4\gamma_{cr,1}}{a} \frac{T_o}{\Sigma - \Lambda} \frac{M}{\rho_{cr}}$$

This freezing point lowering increases directly proportional with the interfacial tension and is inversely proportional to the size of the crystal. The value $\delta T_a$ is expressed as:

$$\delta T_a = -\frac{4\gamma_{cr,1}}{a\rho_{cr}} \frac{10^3}{RT_o} K_f$$

$$K_f = \frac{10^{-3}RT_o^2}{(\Sigma - \Lambda)} M$$

is the molar freezing point lowering.
The freezing point lowering of a crystal (cube) because of inhibition of its growth by one chain molecule, which surrounds the crystal, can be expressed by:

$$\delta T_{a,hindered} = -\frac{20}{3} \frac{\gamma_{cr,1}}{a} \frac{T_o}{\Sigma - \Lambda} \frac{M}{\rho_{cr}}$$

$\delta T_a$ (hindered) is proportional to the interfacial tension and is inversely proportional to the edge length $1$, wherein crystals are hindered. Crystals are hindered in their growth by a determinant number of chain molecules which are cooled to about $T_0 - 2\delta T_a$ before equilibrium is achieved with their surroundings. During the growth rate of the crystals each crystal is capable of exerting a tensile stress equal in force to $5 \times 10^{10}$ dynes/$cm^2$ in aqueous polymer solutions. This force generated amounts to $a \cdot \gamma_{cr,1}$ which is equivalent to the aforementioned value $5 \times 10^{10}$ dynes/$cm^2$, a value equivalent to approximately 10 times the tensile strength of the highest quality, fine grain steel.

Recent electron micrograms indicate that intracellular organels are suspended in the cytoplasmic medium by an intracellular matrix of ultrafine tendrils composed of protien polymers. The said collectively form a network of channels or cisternae, which interconnects throughout the cytoplasm fusing to the cell wall, providing minute outlets to the extracellular environment. The enormous tensile stresses exerted by the formation of ice crystals on the protein polymer tendrils or protein filaments is more than ample to break molecular bonds and rupture or fragment the aforesaid filaments. Further the internal stresses exerted on the interior surface of the cell wall is sufficient to rupture the membranes structure.

Figure 2:
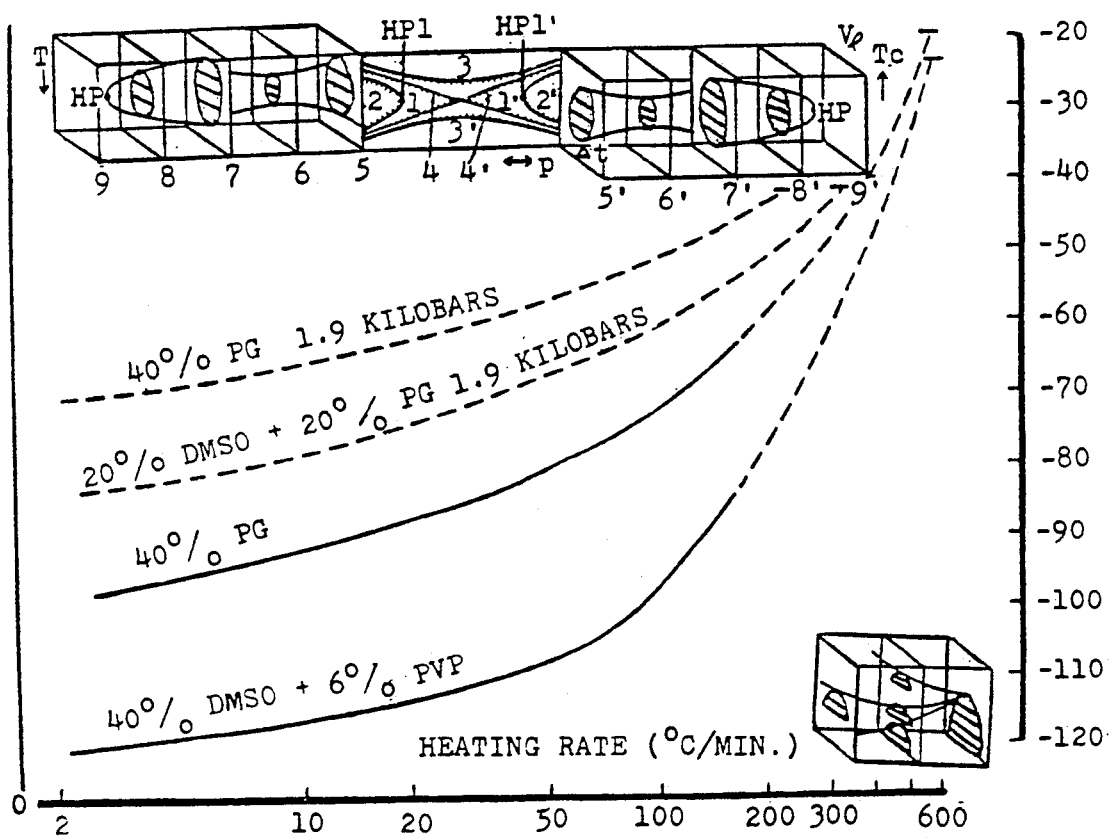
FIG. 2 denotes a graphical representation illustrating the basic effects elicited from biologicals with the introduction of variances in temperature, pressure and concentration of PGF, PGF/NPGF solutes.

FIG. 2 denotes a simplified graphical representation illustrating the basic effects elicited on biologicals by the introduction of temperature pressure and concentration parameters of PGF/PGF+NPGF on the said biological systems. The graph clearly illustrates that devitrification is impeded with a rapid elevation in the temperature, pressure and or increasing the concentration of penetrating solutes either in conjunction with non penetrating low molecular weight solutes such as PVP or singular increments, as shown in the aforementioned figure and evident by the process of extrapolation. The said figure indicates that a concentration of 40% PG plus 40% of DMSO in conjunction with 6% PVP at normal atmospheric pressure requires a temperature elivation of 600° C./min in order to avoid devitrification. FIG. 2 further indicates that the subsequent application of 1900 atmospheres elevates the devitrification temperature ($T_c$) by 30° C. at lower cooling rates and alternately depresses the liquidus temperature ($T_m$) by approximately 20° C., which significantly reduces the absolute energy necessary to prevent devitrification to warming rates on the order of between 200° C./min to 300° C./min rather than 600° C./min.

The upper portion of FIG. 2 further illustrates a simplified four dimensional schematic representation of the effects of temperature, pressure, concentration of PGF/NPGF solutes as a function of time within the context of the vitrification/devitrification cycle. The four dimensional representation defines the pressure dependence of a critical solution as being $P_1$ the critical concentration of solutes for said solution as Xc, the critical temperature being equivalent to Tc and temporal increments of $\Delta t$. The hypercritical solution point defined as Hp a super-critical point wherein sublimation, molecular collapse or vaporization occurs. The region wherein vitrification occurs is demarcated by numeric values 1, 1' to 3, 3' and has an upper and lower limit set by Hp and Hp' respectively. Regions 2 and 2' are indicative of transition levels associated with a considerable slowing of molecular motion, whereas 2' denotes a region of increased molecular mobility. A increase in pressure and a lowering of temperature to a point approaching absolute zero is indicated at the extreme left of the four dimensional representation; whereas extreme elevations of temperature and pressure are indicated to the right of the same said schematic representation. Hp at the extreme left, wherein the temperature approaches absolute zero is indicative of molecular collapses, alterations of dielectric properties and the subsequent arresting of motion of biologicals, solutes and the like. The upper limit is depicted at the right of the schematic representation wherein the $T_c$ and $T_m$ are encountered. Numeric values 5' through 9' denotes pressure increments from one atmosphere to an excess of 2000 atmospheres. Numeric value 5 through 9 to the left of the four dimensional representation denotes gradual decreases in pressure from 2000 atmospheres to under 100 atmospheres with accompanying decreases in pressure. Located on either side of the vitrification region or four separate sectioned modus each of which is indicative of a separate phase transition locus, indicative of complete molecular collapse at the left to vaporization at the extreme right of the said four dimensional chart. To the lower right hand position of FIG. 2 is a simplified schematic version of separate PGF/PGF+NPGF attaining a critical concentration with a decrease in temperature that is accompanied by a simultaneous increase in pressure.

Figure 3:
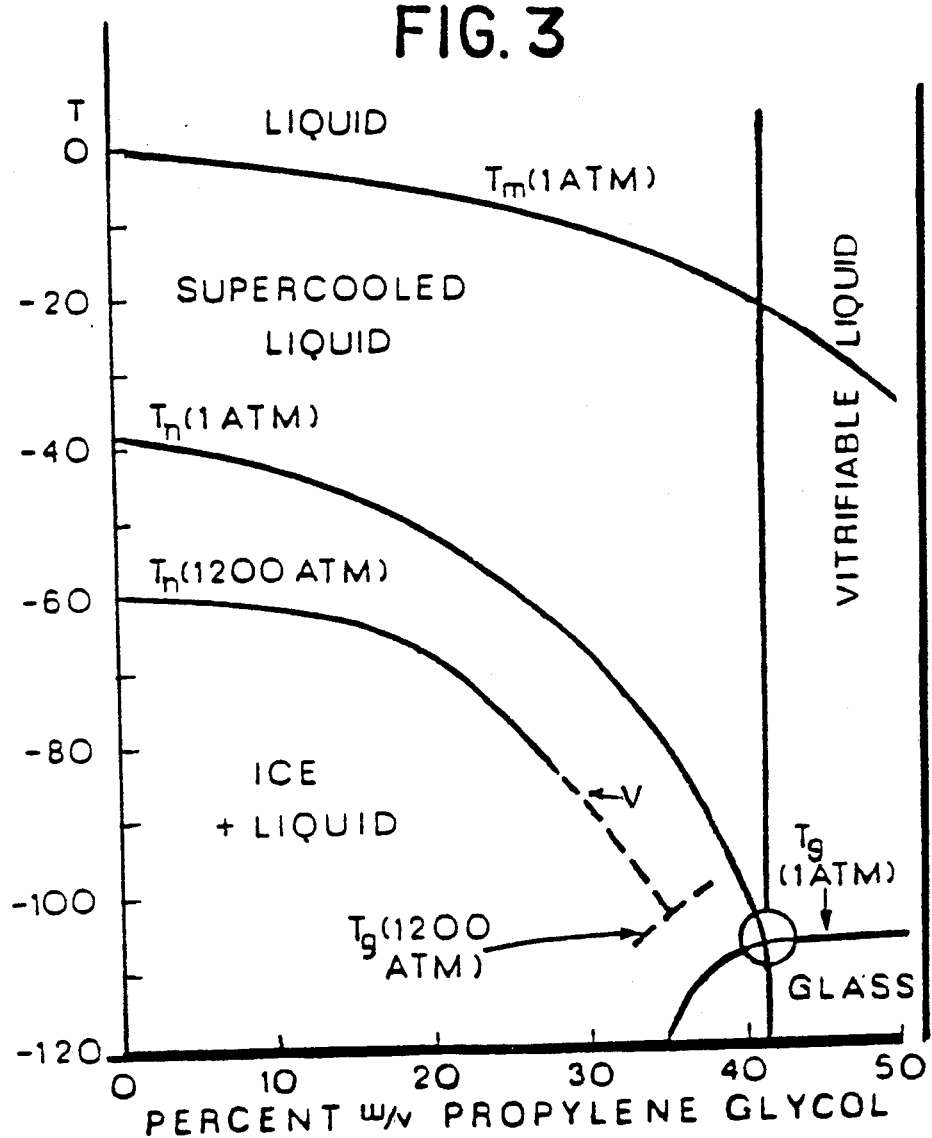
FIG. 3 is a concise simplified graphical representation of the operative effect increments of a single PGF taken in relation to temperature and pressure on the $T_g$, $T_m$ and $T_n$ values or states.

FIG. 3 is a concise simplified graphical representation of the effects of uniformed increments of a PGF solute which when varied with parameters in pressure and temperature operate on values of $T_g$, $T_m$ and $T_n$ respectively, to alter their state. The PGF component exhibited in the said figure is propylene glycol(PG) is raised by increment of 10% W/V until a optimum saturation point of 50% is attained. The aforementioned PGF component PG is choosen specifically because its behavior is typical to all PGF component solutes implied or specifically mentioned. Demonstrated in an illustrative manner one can clearly see that the vitrification pressure (VP) is directly related to the vitrification concentration (VC) and that by manipulation of the cooling rate VC and VP will directly vary accordingly. Further, it is demonstrated that the cooling rate is inversely related to the amount of pressure needed to vitrify a given solution. Further indicated in FIG. 3 is the exemplary cryogenic behavior of biological solutions subjected to increases in PGF solute concentrations in relation to two separate and distinct extremes in pressure in the present of decreasing temperatures.

Figure 4:
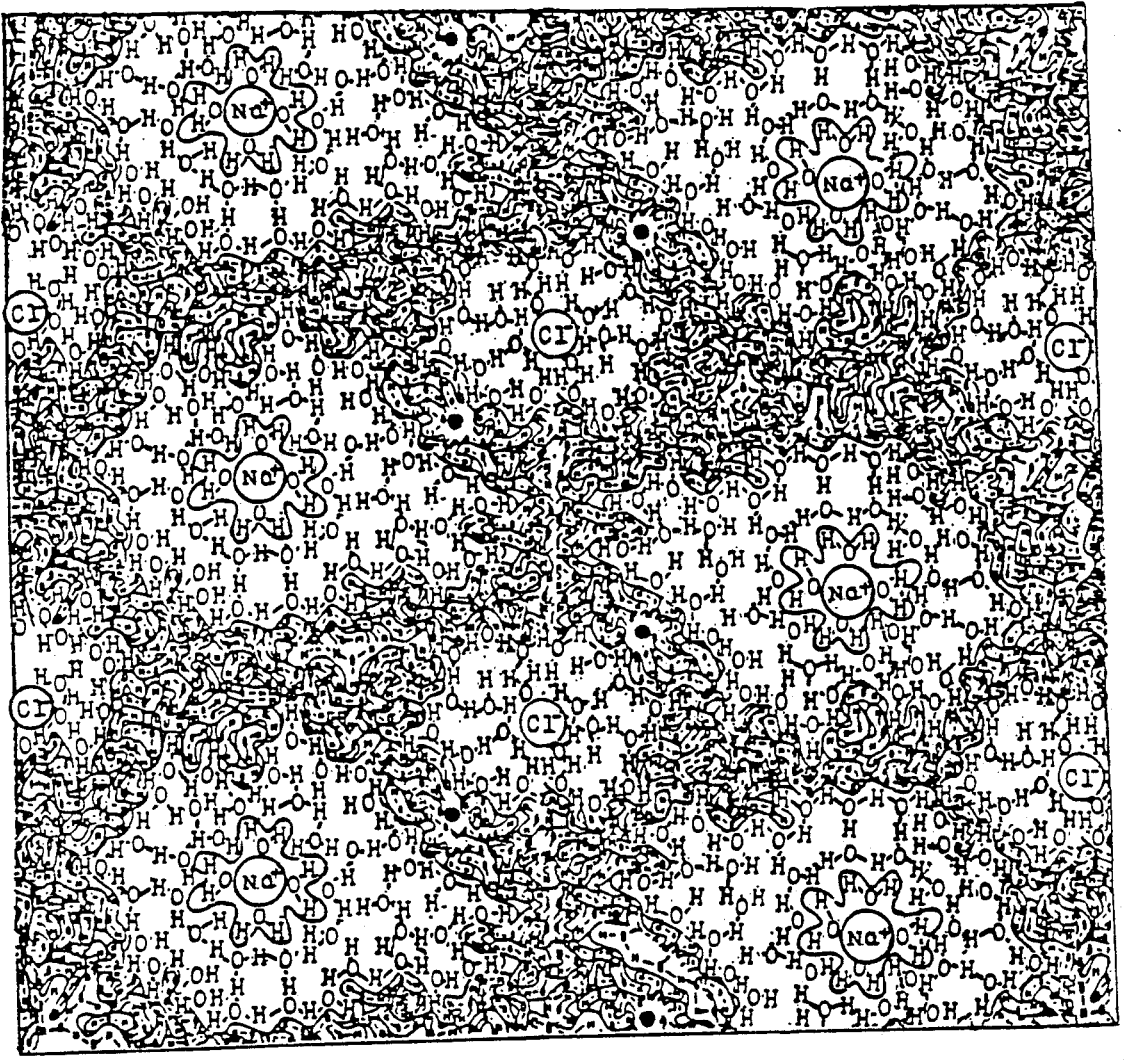
FIG. 4 is a pictorial representation illustrating in part the intermolecular distortion that an aqueous medium undergoes as an ionic medium becomes dissociated in the said aqueous environment as a discrete function of temperature.

FIG. 4 is a pictorial representation illustrating in part the intermolecular distortion an aqueous medium undergoes as an ionic medium becomes dissociated in the said aqueous environment. The simple ionic solute which undergoes dissociation depicted here is sodium chloride and its effects are typical of electrolytes composed of an anion and a cation. The effects of electrolytes on the colligative properties of biological solution in relation to other solutes are negligible within the scope of this invention.

The invention incorporates within its embodiment the unique and novel application of operative quasi-electronic resonant energy fields in order to exact, sustain and propagate cryogenic suspension. Biological solutions are composed optimally of between 85% to 97% water. Said operative quasi-electronic resonant energy fields correspond to the predetermined electromagnetic fields necessary to prevent crystal alignment which corresponds to the vibrational spectroscopy of liquid water, as tabulated in table 4.10 of Eisenberg and Kauzmann (The Structure AND PROPERTIES OF WATER 1969), the vibrational frequency of water molecules as ascertained by Shimanauchi (National Bureau of Standards NTIS, Series:NSRDS-NBS-6, NSRDS-NBS-11, 1967), Everdlov's Vibrational Spectra of Polyatomic Molecules Table 207, 1974 and other equivalent sources well known by those skilled in the art. Examples of the vibrational spectroscopy, vibrational frequency and vibrational spectra are enclosed in tabular form in the table herein below:

| | | | $H_2O$ | | |
|---|---|---|---|---|---|
| | | | Raman | IR | |
| Mode | | | | gas | |
| number | Symmetry | Coordinate | $\nu(I)$ | $\nu$ | $\Lambda$ |
| 3 | $B_1$ | $q^-$ (O—X) | 3654.5 (s.) | 3755.79 | 21.5 |
| 1 | $A_1$ | $q^+$ (O—X) | | 3656.65 | (s.) |
| 2 | $A_1$ | $\alpha$ (XOX) | | 1594.78 | 25.2 |
| The general valence force field (GVFF) Harmonic frequencies in cm$^{-1}$ of $H_2O$. | | | | | |
| Symmetry | | $\omega_1$ | $\omega_2$ | | $\omega_3$ |
| $H_2O$ | $C_{2v}$ | 3832.2 | 1648.5 | | 3942.5 |

The above mentioned values listed in the table herein above are consistant with values obtained by other sources with only slight deviations in said values. The term vibrational in regards to spectra, frequency and spectroscopy refers to the electronic state of molecular water. Said predetermined frequencies are readily exacted and maintained by radiofrequency, electric induction, infra-red laser sources and other well known means at temperatures and pressures where ice nucleation is prevalent, as previously indicated in FIG. 3 of the specifications. The aforementioned emitting apparatus producing said predetermined frequencies is coupled to a standard wave generator with said predetermined resonant frequencies for the aforesaid electromagnetic fields encoded into the memory of a computer source coupled to said generator means, coupled to an array of sensors which monitor the output of said apparatus and the effects of the said electromagnetic fields and further coupled to controller elements which regulate the output of said apparatus in a manner well known by those skilled in the art. The aforesaid predetermined frequencies are administered to only correspond to the vibrational frequencies, spectra and spectroscopy; or can take into account the vibrational frequencies, spectra and spectroscopy of molecular water and said frequencies, spectra and spectroscopy of solvents, solutes or other substance dissolved or otherwise combined to said water molecules. Either procedure indicated in the abovementioned sentence will produce equivalent results; however the former is preferred because of simplicity (time diminished by a factor of four orders of magnitude), rate of identification and execution (time diminished by a factor of between six and eight orders of magnitude).

Experimental findings indicates that the complexity, time and cost differential for preventing the nucleation and subsequent alignment of ice crystals in an aqueous medium ranges on the average between ten thousand to in excess of one million times less for systems emitting said predetermined electromagnetic fields for water molecules rather than emitting said predetermined frequencies for water molecules and all other substances dissolved or otherwise combined to said water molecules.

The rate at which tissues or organs can be placed in a state of cryogenic suspension and recovered from said state of suspension varys directly with the size, mass, type and density of the structure forming said tissue and organs. The apparatus and method which prevents nucleation and subsequent alignment by emitting predetermined electromagnetic fields for one substance rather than ten or more said substances is significantly more reliable and efficient than said apparatus and methods emitting said fields for ten or more said substances.

Since water is a major constituent of biological solutions it becomes necessarily incumbent to discuss the thermodynamic parameters governing aqueous mixtures. Recited and contained herein below are a series of well known equations describing in part the energetics of aqueous mixtures closely approximating those of biological solutions. A non-equilibrium thermodynamical approach is utilized in accordance with Davis, Jarzynski and others and described in part by the following expression, $$Y = \sum_{N_1=0}^{N_o} \frac{N_o!}{N_1! N_2!} \left[\exp\left(-\frac{F_1}{RT}\right)\right]^{N_1} \left[\exp\left(-\frac{F_2}{RT}\right)\right]^{N_2} \times \exp\left[\frac{-p(N_1 V_1 + N_2 V_2)}{RT}\right].$$

where the subscripts 1 and 2 refer to open and close packed structures, $N_o$ is the total number of molecules present, F is the molar Helmholtz free energy and V is the molar volume. The chemical species solution, solute and the like are considered to be mixtures not of separate and distinct clusters by mobile species such that, values of $N_1$ and $N_2$ now correspond to the maximum series for Y which can be obtained by the expression, $$\ln \frac{N_1}{N_2} = \left(\frac{F_2 + pV_2}{RT}\right) - \left(\frac{F_1 + pV_1}{RT}\right) \frac{N_1}{N_2} =$$

$$\exp\left(\frac{-\Delta G}{RT}\right).$$

where
$\Delta G = (F_1 + pV_1) - (F_2 + pV_2) = \Delta F + p\Delta V = \Delta H - T\Delta S$ is the change in Gibbs free energy between open and close packed structures; H denotes the enthalpy and $\Delta F$, $\Delta H$ and $\Delta S$ are variances in the respective parameters of the two said structures. The number of molecules and the like between open and close packed structure when equilibrium values are considered or described by $N_1$ and $N_2$, respectively at some arbitrary temperature T and pressure p (actually the system is in dynamic flux such that a series or distribution of equilibrium states are exacted). The equilibrium distribution can be expressed in terms of the mole fractions $X_1$ and $X_2$ rather than $N_1$ and $N_2$ for the open and close packed structures, as indicated by the expression, $$\frac{x_1}{x_2} = \frac{x_1}{1-x_1} = \exp\left(-\frac{\Delta G}{RT}\right) = \exp\left(\frac{-\Delta H + T\Delta S}{RT}\right),$$

where $N_1 = N_0 x_1$, and $N_2 = N_0 x_2$.

The molar volumes $V_1$ and $V_2$ are related by the following expression, $$V = x_1 V_1 + x_2 V_2 = V_2 + x_1 \Delta V.$$

The effects of lower temperature ranges ($°C_{Tn} \rightarrow -X°C_{Tg}$) were suggested by Wada, Litovitz and others and indicated in the following expression, $$V = x_1 V_1°(1 + \beta_1 T) + (1-x_1) V_2°(1 + \beta_2 T).$$

where $V_1°$ and $V_2°$ are volumes of open and close packed structures at 0° C., values of $V_1°$ and $\beta_1$ are chosen to agree with those of ice. Values $V_2$ and $\beta_2$ are consistent with the heat of sublimation and the heats of fusion and vaporization of water.

Earlier in the disclosure it was explicitly mentioned that the introduction of GPF/NPGF solutes and the like effect the colligative properties of biological solutions. The thermodynamics of a dilute aqueous solution which are composed of N water molecules, $N_s$ solute molecules at a given arbitrary, fixed temperature, T and pressure P are the first supposition. The second supposition is that extensive thermodynamic quantity E can be viewed as a function of a series of variables (P,T, $N_s$, N, $N_o$ . . . N!). The thermodynamic characteristics are reducible and can be computed on the basis of partial molar quantities of the solute S designated by the following simplified expression, $$E_S = \left(\frac{\partial E}{\partial N_S}\right)_N.$$

for the sake of simplicity let's assume that the aqueous mixture consists of five separate and distinct chemical species as described by the expression below $$dE = \left(\frac{\partial E}{\partial N_S}\right)_{N_0...N_4} dN_S + \sum_{k=0}^{4} \left(\frac{\partial E}{\partial N_k}\right)_{N_j, j \neq k} dN_k$$

dividing by the value $dN_s$ and requiring the total number of water molecules to be constant the following expression is obtained $$E_S = \left(\frac{\partial E}{\partial N_S}\right)_N = \left(\frac{\partial E}{\partial N_S}\right)_{N_0...N_4} + \sum_{k=0}^{4} \left(\frac{\partial E}{\partial N_k}\right)_{N_j, j \neq k} \left(\frac{\partial N_k}{\partial N_S}\right)_N$$

assuming that the value N equals the total number of water molecules and that there are K hydrogen bonds then $$E_S = E_S^* + \sum_{k=1}^{4} (E_k - E_o)\left(\frac{\partial N_k}{\partial N_S}\right)_N$$

and introducing this condition and symbols the expression becomes, $$E_S^* = \left(\frac{\partial E}{\partial N_S}\right)_{N_0...N_4}$$

$$E_k = \left(\frac{\partial E}{\partial N_k}\right)_{N_j, j \neq k}$$

$$\Delta E_S^r = \sum_{k=1}^{4} (E_k - E_o)\left(\frac{\partial N_k}{\partial N_S}\right)_N$$

which obtains $$\bar{E}_s = E_s^* + \Delta E_S.$$

There exists a cofactor whose presence drives the system species of water molecules to equilibrium or otherwise the system $N_{Ks}$ exhibits independent behavior. The initial system influenced by a cofactor attains equilibrium with a composition of $N_s$ $N_o$ . . . $N_4$, when the cofactor is removed $dN_s$ moles of s have been transferred to the said system. In the aforementioned system $N_k$ values are kept constant with the measurable partial molar quantity being defined by $E_s^*$, which like $\Delta E_s^r$ depends on the intrinsic structure of the solvent. The two extreme states range from where a molecule is fully bonded to molecules which have no bonded elements. The intermediate group of solutes species have occupied intermediate states of bonding. The relative partial molar quantities can be expressed in terms of enthalpy and entropy interactions as expressed herein below $$H_S = H_x^* + (H_4 - H_o)\left(\frac{\partial N_4}{\partial N_s}\right)_N \quad \mu_4 = \mu_o^*$$

$$S_S = S_S^* + (S_4 - S_o)\left(\frac{\partial N_4}{\partial N_s}\right)_N \quad \mu_s = \mu_s^*$$

$$\mu_S = \mu_S^* + (\mu_4 - \mu_o)\left(\frac{\partial N_4}{\partial N_s}\right)_N \quad T\Delta S_S^r = \Delta H_S^r$$

In the absence of a detailed explaination of the standard deviations between the fully bonded species and the unbounded species that $\bar{H}_4$ (bonded)-$\bar{H}_o$(unbounded) and $\bar{S}_4$bonded)-$\bar{S}_0$(unbonded) are both negative (enthalpy and entropy of reaction respectively). Occasionally, anomalous behavior is exhibited in $T_g/T_n$ ratios when the combination of PGF and NPGF solutes are utilized; there is additionally a corresponding large negative value of $\overline{H}_s$ in water which is thought to be attributed to the contribution of $\Delta H_s^r$ (a relaxation term). The relaxation term $\Delta S_s^r$ contributes additionally to the negative value of $\overline{S}_s$ and $\overline{H}_s$ having contributions from both the static and relaxation states. The chemical potential for solute species is defined by the quality $\mu_s$. Further the relaxation portion of $\overline{H}_s$ exactly compensates for the relaxation portion of $T\overline{S}_s$. The above mentioned formula has implications involving solubility of gases in relation to effects of structural change in the dilute aqueous solution.

The intrinsic atomic and molecular vibrational frequency of the species existing in clusters, forming dilute aqueous mixtures are of particular interest in establishing a resonant frequency which would have an inhibitory effect on the formation of crystals and their subsequent alignment. The number of species existing in clusters are described by values $n_o$, $y_1$ and a third parameter $x_\mu$ representing the unbounded mole fraction of molecules from the entire aqueous system. Values $n_o$, $y_1$ and $x_\mu$ must satisfy the minimum free energy requirements for the said system. The actual mole fraction in liquid for the unbonded species becomes $X_u$ and for the bonded (hydrogen bonded) species $x_i = y_i(1-x_u)$ with $i=1, 2, 3, 4 \ldots$ for a limited number of solute species ($n \approx 5$). $y_i$ represents the number of fraction of molecules having i hydrogen bonds and the cluster are all considered to be of a uniformed size denoted by $n_o$. At any given interval of time a single $n_o$ and a single set of $x_i$'s will give a good first order approximation of the mean averages over an entire range of structures occurring in the aforementioned aqueous liquid. The partition function corresponding to modified conditions proposed by Nimethy, Scheraga and others is exemplified in the expression contained herein below, $$Z = \sum_{(n_o, y_1, x_u)} g(n_o, y_1, x_u) \prod_{f=1}^{4}\left[f_1 \exp\left(-\frac{E_l}{RT}\right)\right]^{N_o x_i}$$

$$g(n_o y_1, x_u) = \frac{N_o!}{N_4! N_3! N_2! N_1! N_U!},$$

where g is a combinatorial factor, $N_i = N_o x_i$ is the number of molecules of each species (1=4, 3, 2, 1, u) and u refers to the unbonded species. The value $N_o x_i$ represents the avogadro's number and is equated to the mole fractions of various species in the said liquid and $E_i$ represents the minimum potential energies of the various species. The factor $f_i$ are partition functions of the individual molecules in various states of bonding. The states of bonding for molecules involved in hydrogen bonding are indicated by three translational and three rotational degrees of freedom, which are represented by six vibrations. Each molecules is set in motion with every other, with each of the same said molecules moving in the effective field of molecules adjacent to it. The unbonded molecules are assigned two vibrational modes, corresponding to vibrations changing the orientation of the dipole axis with respect to the dipole field of the neighboring molecules, and one rotational mode, corresponding to free one-dimensional rotation around the dipole axis. The unbonded species is also assumed to have translational freedom within a cage defined by its nearest neighbors as in the free-volume theories of normal liquids. The molecular partition functions for the various species are $$f_i = f_{vib} \text{ for } i = 1,2,3,4$$
$$f_u = f_{tr} f_{rot} f_{vib}$$
where $$f_{vib} = \prod_{f=1}^{s}\left[1 - \exp\left(-\frac{h\nu_{ij}}{kT}\right)\right]^{-1}$$

with $s = 6$ for $i = 1,2,3,4$, and $s = 2$ for $i = u$.

$$f_{tr} = \left(\frac{2\pi mkT}{h^2}\right)^{3/2} V_f$$

$$f_{rot} = \prod \left(\frac{2\pi mkT}{h^2}\right)^{1/2}$$

The subscripts tr, rot and vib refer to translation, rotation, and vibration respectively, m is the mass of the molecule, and I is its moment of inertia around the dipole axis. The frequencies $\nu_{ij}$ used in the partition functions were assigned on the basis of infrared and Raman frequencies reported for water. For the $\nu_{ij}$'s chosen, the corresponding Debye temperatures are well below room temperature. The value of $f_{vib}$ obtained by NS in water corresponds very nealy to the classical value, and the particular assignment of $\nu_{ij}$'s is unimportant. The quantity $V_f$ represents a "free volume" for the translation of the unbonded molecule. According to the cell theory of liquids which is given by, $$V_t = \int \exp\left(-\frac{W'}{kT}\right) dr.$$

where dr represents a volume element and W is the interaction potential in dr due to the neighbors molecules. The energy, $E_n$, and the free volume, $V_f$, depend on the interactions between the molecules in the unbonded liquid. There is no precise data about the magnitude of these interactions, it is not possible to derive values of these parameters from theory, thus $E_H$ and $V_f$ were treated as adjustable parameters that could be varied within the limits of physically reasonable values, to give the best fit to experimental to temperatures approaches $T_g$, $T_n$.

Figure 5:
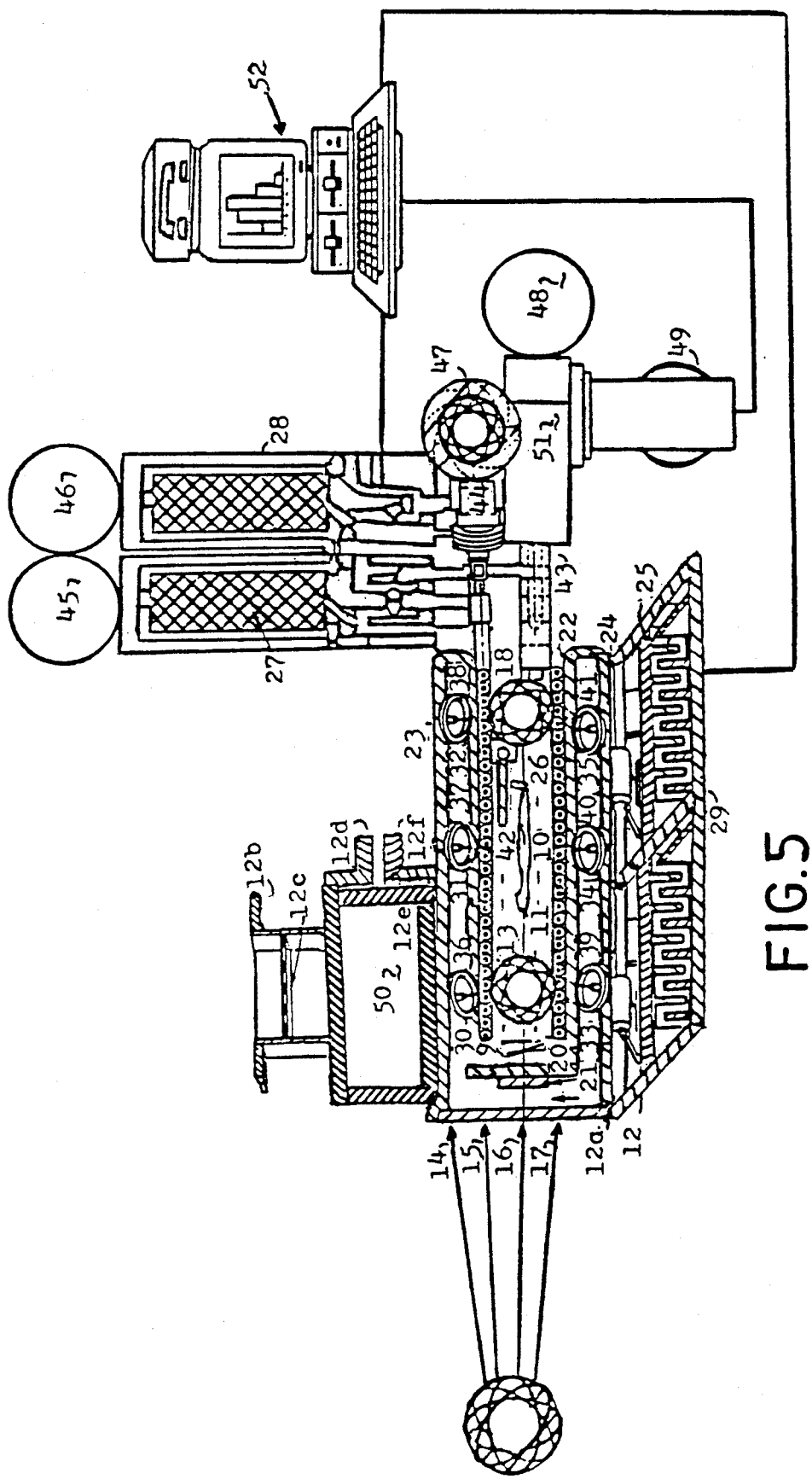
FIG. 5 is indicative of a concise simplified pictorial representation which succinctly illustrates a biological system contained within the operative perimeter of a cryogenic suspension unit.

FIG. 5 is indicative of a concise simplified pictorial representation succinctly illustrating the presence of a viable biological system contained within the operative perimeter of a cryogenic suspension unit. The biological system described by numeral 10 is both submerged and suspended in a non-adhering non-toxic protective liquid solution (composed of PGF, NPGF, heavy molecular weight colloids and the like) designated by numeral 11. Both the biological system, numeral 10 and the protective liquid suspension are contained within the confines of a variable elastic hermetically sealed solid state cryogenic suspension capsule, which is indicated by numeral 12. Incorporated within the structural contexts of the liquid capsule numeral 12 is a double hull system, an insulatory lining composed of a series of elastic glassified boron and nitrile silicate and a number of layered structures consisting of commercially available epoxylated metallic composites described herein by numeral 12a, 12b and 12c respectively. A double flow channel for cryogens, a passive heat exchanger and a a network or array of feedback sensory means are incorporated throughout the framework of the solid state capsule structure as indicated by numerals 12d, 12e and 12f respectively. Within the interior hull structure are six equivalent piezoelectric sonic resonator means, which are defined by elements 13 through 18 each equipted with its own parabolic focusing means defined by numbers 19 through 24 and all interfacing means of the interior hull 25 is coated with a non-adhering cryogenic protective surface numeral 26 (composed of a commercially available and modifiable coating of teflon or its equivalent) which is in direct contact with the said protective suspension numeral 11. Two pump compressor complexes are designated by the numerals 27 and 28 which provides pressurization and circulates cryogens (liquid nitrogen, helium and the like). A complex of heat exchanges defined by element 29 which absorbs, conducts and exhaust heat through the process of thermal dissipation. Elements 30 through 35 and 36 through 41 denote six equivalent radiofrequency modulators and six equivalent laser microwave field generators. The operations of profusion, the infusion and subsequent withdrawl of PGF, NPGF, metabolic stablants and the like are initially conducted by a complement of hydraulic injection servos mounted in their own separate and distinct robotic arms specified by elements 42 through 44. The hydraulic injection servos operate in transitory periods to profuse or withdraw fluid mediums from the said biological system (i.e. organs, circulatory tract and the like). Reservoirs of cryogenic, base profusiates, metabolic stablants and other ancillary exogenous substances are described by elements 45 through 50. Indogenous components of the aforementioned biological system are indicated by numeral 10 and are subsequently withdrawn by one of the said servo means (element 42 through 44) and are subsequently held and processed by plant means 51 to be reintroduced upon the biological systems reintroduction to ambient conditions of temperature and pressure.* All operative processes concerned with cryogenic suspension are under the control of a automated feedback network containing within its framework a computer complex both of which are designated by a single numeric value, number 52.

The indogenous components of the biological system referred to here consist of the organisms whole blood and related byproducts contained therein.

Figure 6:
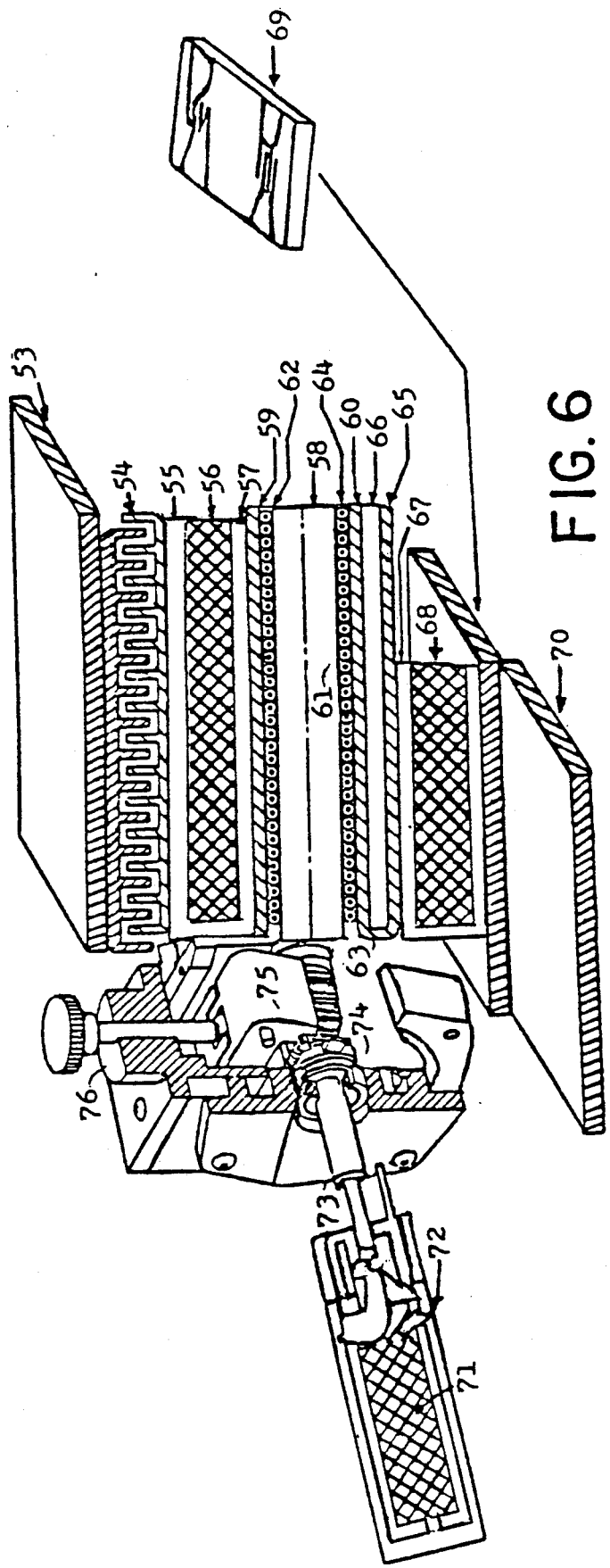
FIG. 6 entails a detailed sectioned view denoting a critical portion of the structural encasement which forms the solid state capsule.

FIG. 6 entails a detailed sectioned view denoting a critical portion of the structural encasement which forms the solid state capsule. The outermost portion of the encasement structure is composed of a layer of nonconducting epoxylated metallic, ceramic material designated by numeral 53. The outermost layer numeral 53 is preceded by a self healing elastic layer described by numeral 54. The above mentioned layer numeral 54 is formed from a network of heat exchangers containing a sensor array and incorporating a mesh of flexible or elastic long chained polymers, which are defined by elements 55 through 57. A high density elastic layer composed of nitrogen silicate is embedded in a polymer mesh, with numeral 58 insulating against thermal losses. The outer portions of layer 58 are coated with a highly reflective, commercially available material such as silver or aluminium, as described by numerals 59 and 60. A pyrex variation of a glass Dewar element is indicated by numerals 61, 65 and 67 respectively with ancillary cryogens circulated through tubular layer 63. Elements 62 and 64 are representative of heat exchanger means. A vacuum is sustained through tubular structure 66. A primary elastic boron silicate glass impregnated with flexible polymers is indicated by number 68. Layer 69 consists of a network solid state piezoelectric modulators when under low power sustains sonic transmissions which are provided by layers of solid state means that inhibit the nucleation and subsequent formation of ice crystals at the nucleation temperature. Numeral 70 is indicative of a non-adhering temperature resistant teflonated layer which is in immediate contact with the fluid suspension in which the biological system is submerged and suspended in. Elements 71, 72 and 73 represent a miniature expander for a modified Gifford McMahon cryorefrigerator, displacer-regenerator and high and low pressure gas lines. A miniature variable pump number 74 both circulates cryogens and provide a vacuum seal for the solid state capsule means.

The pump is powered by a passive Stirling type heat engine means numeral 75 in the absence of a reliable power source. The outer casing housing the pump, Stirling heat engine and the ancillary elements which are indicated collectively by element 76.

Figure 7:
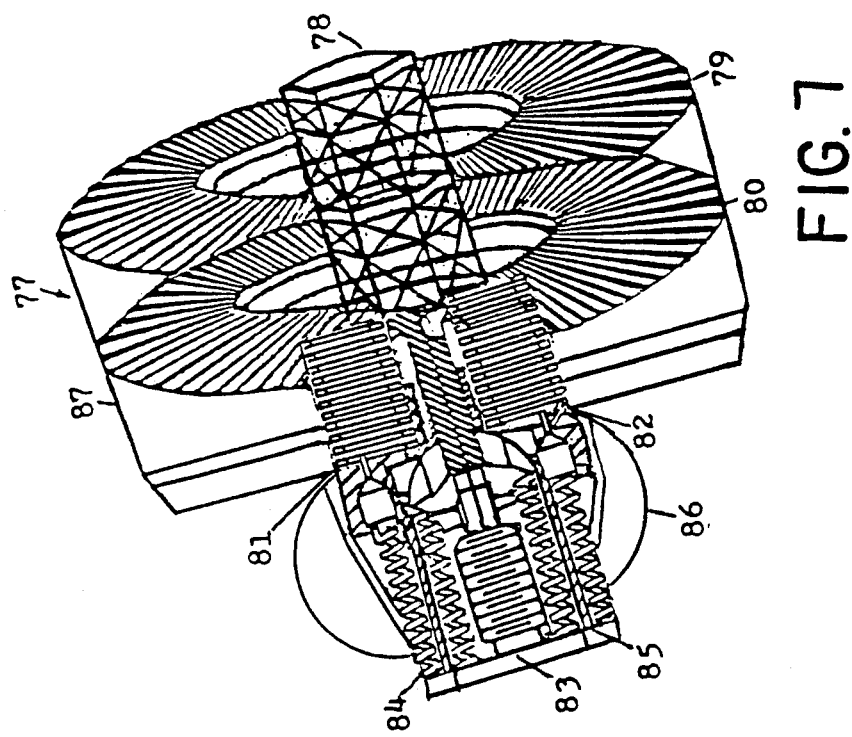

FIG. 7 is a concise detailed sectioned perspective which describes one of six equivalent solid state sonic resonators that are utilized to prevent nucleation and promote the active dispersal of profusiates and the like. Acoustic emissions generated by said sonic resonators correspond to the vibrational frequency of water necessary to prevent the successful formation and alignment of ice, as tabulated by Dorsey in a work titled Properties of Ordinary Water, N.B.S.1940, Califano and other equivalent sources. Vibrational frequency of water in regards to acoustic emissions corresponds to a mechanical value which varies with temperature, pressure, density and composition*. The operative parameters of the sonic generating means is designated by numeral 77. Operation of unit 77 can be effectively illustrated by several simplified field equations. It has now become necessary to recite some basic field equations which are related to the conduction or transmission of sound. They are discussed only in part in the mathematical expressions contained herein below.

*The propagation of high frequency vibrations as determined by Laser densometry, to the exclusion of ice; the practice of which is well understood by those skilled in the art.

Far field sound pressure generated by a source is described in terms of radiated acoustic power Pa such that, $$P^2(r, \phi, \theta) \int_{0-\infty}^{0-n} \frac{pcPaDiR(\phi, \theta)}{4\pi r^2}$$

$P^2(r,\phi,0)$ is the mean square acoustic pressure in pascals; and $r$, $\phi$, $\theta$ are equivalent to spherical coordinates. $r$ is meters, whereas $pc$ is equivalent to the product of density and the speed of sound of a given medium. In other words the acoustic impedance of the medium in $(N)5/m^3$; $R(\phi,0)$ a normalized pattern function. $Di$ is equivalent to the directivity factor of a source which is defined as, $$\frac{1}{Di} = \frac{1}{4\pi r_o^2} \int\int \frac{P^2(r, \phi, \theta)}{P_o^2} dS.$$

Po is defined as distance $r_o$ in the direction of maximum response, and the value dS is equivalent to the element of surface area on a spheriod having a radius $r_o$.

Normalized beam patterns may be deduced graphically by the plotting of 10 log $P^2$ ($\phi$, $\theta k$) versus 0 for a particular value of $\phi$, $\theta k$ by dividing or factoring the equation $P^2$ (r, $\phi$, 0) by the square of the input impedance $I^2$ such that, $$\frac{P^2(r, \phi, \theta)}{I^2} = \left(\frac{PcDiR(\phi\theta)}{4\pi r^2}\right)\left(Re \frac{Pa}{Pe}\right).$$

Pe is equivalent to the electrical input power administered to the transducer means in Watts, Re is equivalent to the electrical input resistance of the transducers and both are related to the intrinsic vibrational frequency of the said transducer means.

The current transmitting response which is denoted by 20 log So, is expressed in the mathematical expression which follows:

20 log $So$ = 10 log $Re$ + 10 log $Di$ + 10 log $Nea$ + 170.8
(dB re 1 $\mu$Pa/A at 1 m)

10 log Di described the directivity index ND, or the gain of the transducer, whereas Nea Pa/Pe.

If the reaction of a medium is on the moving surface of the transducer it is assumed that the vibrating surface has a velocity u, and that the surface exerts a force Fr on the transmit medium (i.e. water, air or a lattice configuration) on the moving surface of the source is $-Fr$, the radiation impedance Zr can be expressed such that, $$Zr = \frac{-Fr}{u} = Rr + jXr.$$

Rr describes the radiation resistance and Xr is equivalent to radiation reactance. Upon simplification in a linear system consisting of a continuous, the value of Zr is frequency dependent and is a constant at a constant frequency.

If the radiation impedance can be exacted the mathematical estimate of acoustic power can be expressed as, $Pa = \frac{1}{2} U^2$ peak $Rr = U^2$ rms $Rr$ The radiation impedance for a simple, rigid piston, for radius a. in a infinite baffle can express its radiation impedance as, $$Z = \pi a^2 pc \left[ 1 - \frac{J_1 2Ka}{Ka} + J \frac{S_1(2Ka)}{Ka} \right]$$

where J denotes a Bessel function and S is equivalent to Struve function.

If a spheriod of radius a, is the source radiator then the radiation impedance can be described bt the expression;

$$Z = \frac{4}{3} \pi a^2 pc \frac{(Ka)^2 + jKa}{1 + (Ka)^2}$$

$$Z = \frac{4}{3} \pi a^2 pc \frac{(Ka)^4 + jKa(1 + K^2 a^2)}{4 + (Ka)^4}$$

The nature of equations governing piezoelectric materials in regards to transduction has already been described earlier by the following equations.

$S = S^E T + dE$ $D = dT + \epsilon^T E$ $S = S^D T + gD$ $E = -g^T + \beta^T D$ $$d = \left(\frac{\partial S}{\partial E}\right)_T = \left(\frac{\partial D}{\partial T}\right)_E$$

$$g = \left(\frac{-\partial E}{\partial T}\right)_D = \left(\frac{\partial S}{\partial D}\right)_T$$

Numeral 78 designates a metallic quartz crystalline piezoelectric generating means. Numerals 79 and 80 represent two separate and distinct charging plates. The charging coils for the plates 79 and 80 are denoted by elements 81 and 82. Numeral 83 denotes a pulse generator means, many suitable commerically available units can be acquired. Numerals 84 and 85 describe cross-sections of electro-optical transducers and proportional coolant means. Element 86 designates an articulating joint socket means, which is capable of rotating the entire unit 360 degrees of arc in any one of three directions. Numeral 87 designates an outer peripheral parabolic dish structure for concentrating the amplified sound means towards a target loci.

The nucleation, formation and subsequent alignment in tissues and organs of ice crystals is monitored by Laser Densometry* coupling the measuring of optical refractive indexing to acoustical propagation of high-frequency emission through tissues or organs. Experimental evidence conducted on tissues at a cellular level indicates that fragmentation or rupturing of cell membranes or walls occurs within the later stages of of alignment of said crystals rather than during nucleation or formation of said ice crystals. High-frequency acoustic emissions are conveyed to tissues or organs by sonic resonator elements at predetermined frequencies in order to mechanically disrupt the nucleation, formation and subsequent alignment of said crystals. The nucleation, formation and subsequent alignment of said crystals has the highest probability of occurring during the stages of cryogenic suspension and during the later stages of recovery; where the temperatures, pressures and cellular constituents undergo normalization to establishing ambient conditions in said tissues and organs. The physical parameters of matter alters or varies from one physical state to another unlike the quasi-electronic state of matter (excluding a plasma states generated by temperature extremes, ionizing radiation or pressures reducing matter to a singularity). Dorsey and others provide the results of dynamic methods wherein the velocity or propagation of high-frequency acoustic waves are transmitted through water vapor, aqueous solutions (including liquified water) and ice (granulized ice etc. with or without impurities) and said values are well known by those skilled in the art. Said predetermined acoustic vibrational frequencies correspond either to the frequencies characteristic for the propagation of high-frequency acoustic waves through liquified water or to the exclusion of waves propagated through granularized ice to impede the formation of said ice crystals and their subsequent alignment.

* also known as Denimetry

Figure 8:
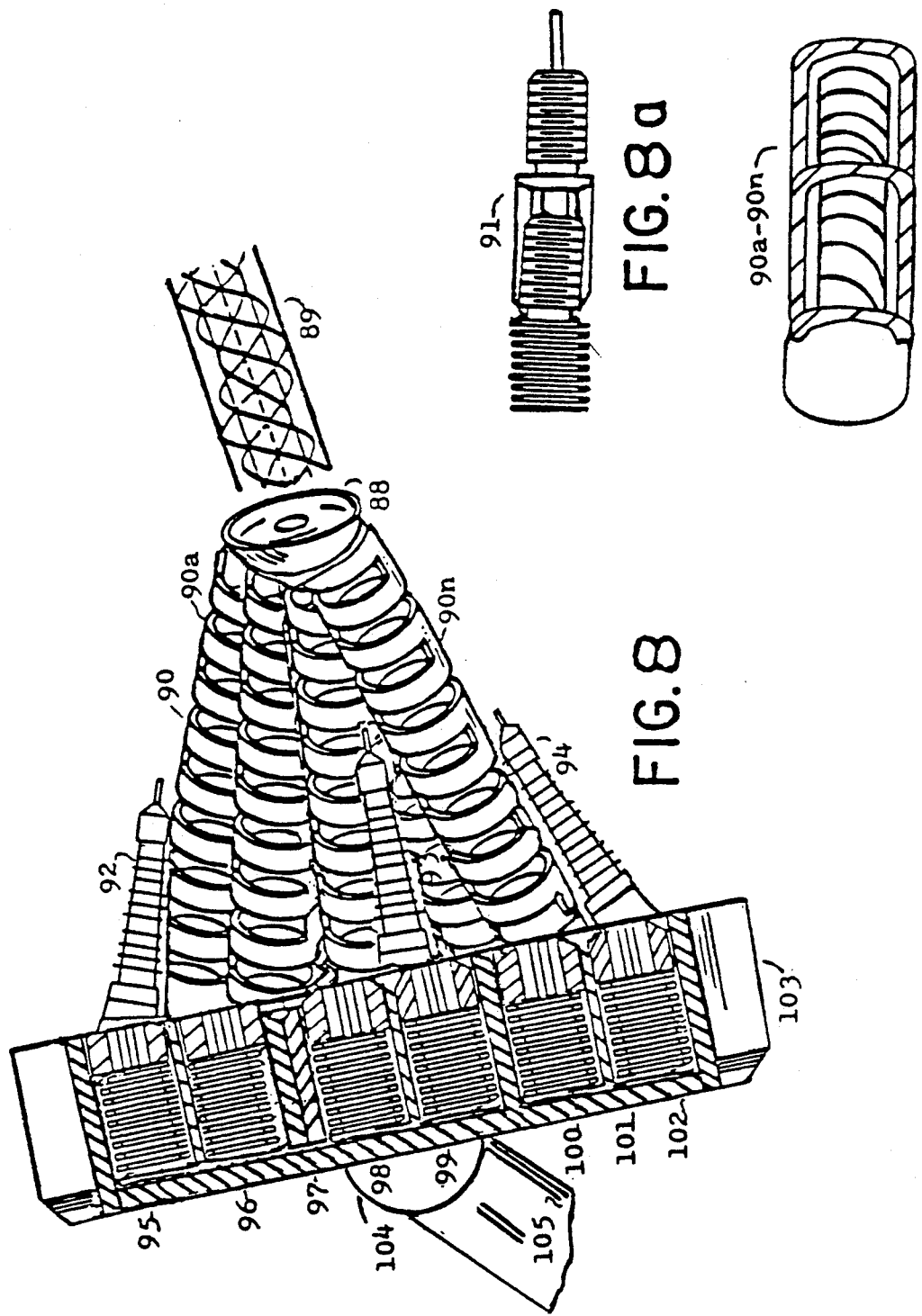

FIGS. 8 to 8b are sectioned perspectives detailing one of six equivalent radiofrequency devices utilized to provide uniformed heating throughout the biological system, upon its recovery from cryogenic suspension and subsequent reintroduction to ambient conditions. Emission 89 is emitted from targeting centriod dish element 88 which aids the collimate source generations traveling in a series of wave guides as described collectively by numeral 90. Numerals 90a through 90n are equivalent wave guide means arranged in a specific geometric manner as to project a tight beam emission. Elements 92, 93 and 94 are representative of separate individual radiofrequency coils, each with a distinct terminus located along the central axis of each separate wave guide. Numeral 91 designates a single radiofrequency coil with an extended terminus. Numerals 97 and 100 denote internally structural support means for parabolic dish structure 103. Elements 95, 96, 98, 99, 101 and 102 denote separate charging coils for the radiofrequency coil means. Numeral 104 describes a single articulating socket joint, located in between support column 105 and dish 103, which provides the necessary 360 degree rotation in three directions needed by means 103 to further orientate emission 89. Some commerically available oscillators provide for Sine wave oscillations in either one of two ways which can be described by the concise simplified circuit equations contained herein below;

$$\left(\sqrt{\frac{L}{C}} \frac{1}{Riv} + 2\right) > \sqrt{\frac{C}{L}} > R > \left(\sqrt{\frac{L}{C}} \frac{1}{Riv} - 2\right)$$

$$\alpha = -\frac{1}{2}\left(\frac{1}{Riv\,C} + \frac{R}{L}\right)$$

and $$w = +\sqrt{\frac{R + Riv}{Riv\,L\,C} - \alpha^2}$$

for oscillator build up $\alpha > 0$ for stable oscillator amplitude $$a = 0$$

for delaying oscillation or for $$\left(\sqrt{\frac{L}{C}} \frac{1}{R} + 2\right) > \sqrt{\frac{C}{L}} \, Ric > \left(\sqrt{\frac{L}{C}} \frac{1}{R} - 2\right)$$

$$\alpha = -\frac{1}{2}\left(\frac{1}{RC} + \frac{Ric}{L}\right)$$

$$w = -\sqrt{\frac{R + Ric}{R\,L\,C} - \alpha^2}$$

From the Aperture Admittance Theory the normal input admittance of the general aperture antenna can be expressed as, $$y = g + jb = c \int_0^\infty [F_{TE}(\beta)\,GTE(\beta) + F_{TM}(\beta)\,G_{TM}(\beta)]\beta d\beta$$

TE and TM refers to part of the solution which is derived from a single transverse electric or transverse magnetic field vector potential in an external medium.

$F_{TE}(\beta)$ and $F_{TM}(\beta)$ are Fourier transformations of the aperture field. Functions $G_{TE}(\beta)$ and $GTE(\beta)$ are normalized solutions to the wave equations in an outside media.

Surface Waves concerning dielectric along real axis B, wherein dielectric covered antennas for variable wave guides are available and may be symbolically denoted as;

$$y = (gr + gs) + ibr$$
$$= C\int_{\beta=0}^{\beta=1} F_1(\beta)\,d\beta + C\int_{\beta=1}^{\beta=N} F_2(\beta)\,d\beta +$$
$$C\int_{\beta=N}^{\beta=\infty} F_3(\beta)\,d\beta$$

The region inside B is evaluated by using the theorem of complex variable theory and the poles are given by the values, $$TE \text{ modes}: j\sqrt{N_2^2 - \beta n} = \sqrt{N_1^2 - \beta^2 n}\,\cot\left(Kod\sqrt{\frac{2}{N_1} - \beta^2 n}\right)$$

$$TM \text{ modes}: -jN_1^2\sqrt{N_2^2 - \beta n} = \sqrt{N_1^2 - \beta^2 n}\,\tan(Kod\sqrt{N_1^2 - \beta^2 n})$$

and as a result of losses incurred by the dielectric so that the radiation aperture conductance gr, the aperture conductance br, and aperture surface wave conductance gs can be described by the following mathematical equation;

$$gr = C\int_{\beta=0}^{\beta=1} F_1(\beta)\,d\beta$$

$$gs = C\pi i\Sigma \quad \text{residues}$$

$$br = C\int_1^N F_2(\beta)\,d\beta + C\int_N^\infty F_3(\beta)\,d\beta$$

Figure 9:
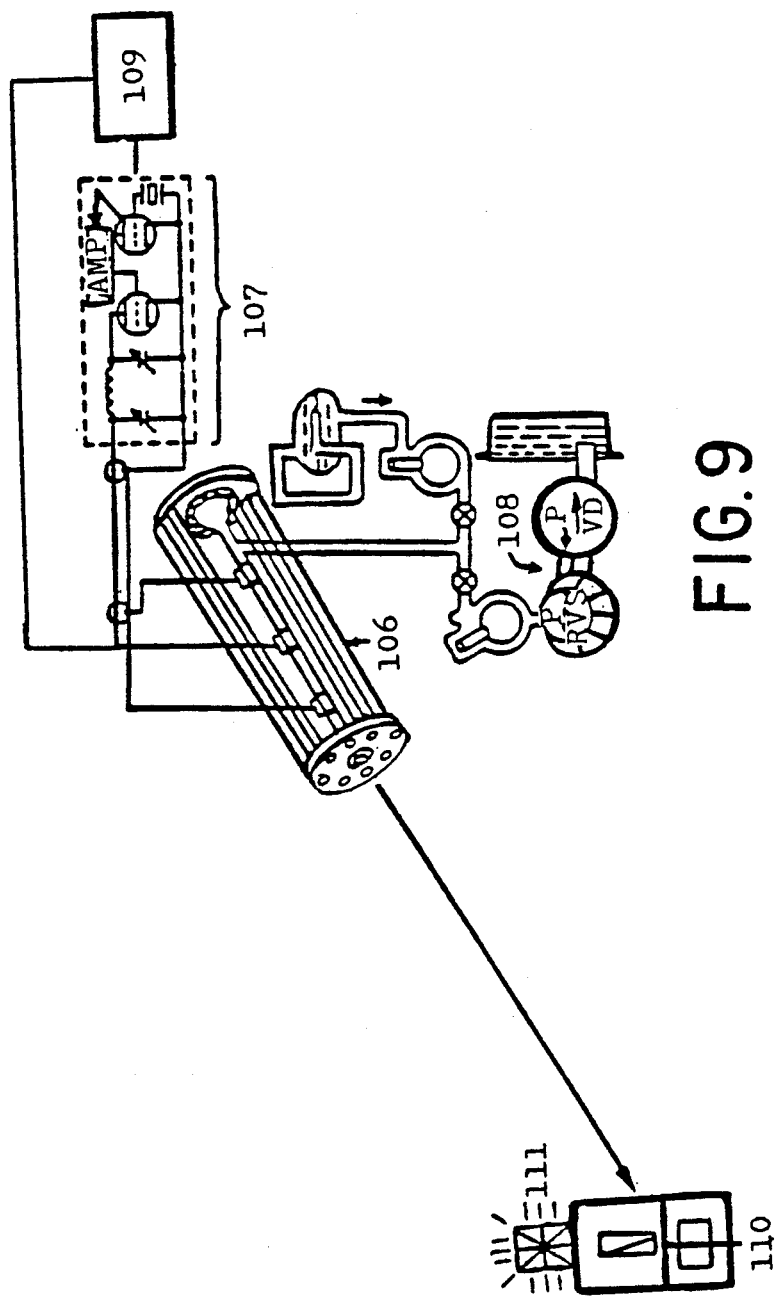
FIG. 9 is a pictorial representation of one of six equivalent microwave lasers utilized to uniformly raise the temperature of the entire biological system upon its emergence from cryosuspension.

FIG. 9 is a concise pictorial representation of one of six equivalent microwave laser means utilized to uniformly raise the temperature of the entire biological system upon its emergence from cryogenic suspension. A modified gas ion laser ($CO_2.N_2$~He or an equivalent combination of gases) is indicated by numeral 106. The said laser means, along with five other equivalent systems, pulse the said biological system and the surrounding media with microwave radiation of a precise wavelength and frequency. Numerals 106, 107 and 108 are indicative of the laser ion source, a radiofrequency excitation circuit and gasifier regenerative pump complex. Element 109, 110 and 111 denote a pulse generating circuit, a rotatable roastal scanner and a variable central focus means with a diffuser means. The said pulse generating circuit provides an oscillation rate of laser pulses which supplies optimum uniformed heating and thermal dissipation to the aforementioned biological system. The above complex of rotatable roastal scanners and the central focus/diffuser means provides multiple positionability of incident beams, varying the effective size of the same said incident beam area. The rate at which biological tissues optimally absorbs and dissipates microwave radiation has been described by Green, Shapiro, Schwan and Kritikos. The primary importance of any and all equations discussed is to provide the necessary criteria needed for operative systems to distribute energy in a even and uniformed manner in order to prevent uneven differential cellular heating, devitrification and or nucleation. The heat transport of tissues is briefly illustrated by the following concise differential equation with regards to blood flow and superfical effects at the skin layer of the organism.

$$\frac{\partial T}{\partial R} = -\alpha T - \alpha(T_{bl} - T_a)$$

$T_{bl}$ = Blood Temperature, $T_a$ = Air Temperature, where $\alpha$ is a radiation coefficient. This result indicates that the heat flow S $$S = k \frac{\partial T}{\partial R}$$

is proportional to the temperature differential of the skin temperature minus the air temperature, i.e.

$$\frac{S}{k} = -\alpha(T - T_a)$$

Additionally from the works of Foster, Kritikos and Schwan explicit descriptions of the outer layer including the skin approaching a deapth of 1 cm the parameter of skin conductance is defined by the following expression:

$$K_s = \frac{S}{T_c - T_s}$$

where
S is the heat flow through the skin,
$T_c$ is the core temperature, and
$T_s$ is the skin temperature.

Further the skin conductance is highly variable quantity, which ranges from the low value of 6-7 kcal/hr m$^2$ to the extreme case of 50 kcal/hr m$^2$. Taking these considerations into account, the boundary condition is taken to be, $$\frac{\partial T}{\partial R} = -\alpha(T)T - \alpha(T)(T_{bl} - T_s),$$

where $\alpha$ has the range 0.25 cm$^{-1}$ < $\alpha$ < 2.5 cm$^{-1}$.

The core blood flow rather than loss of heat from the surface of the tissue, limits the microwave-induced temperature increase at tissue depths greater than 1 cm or more upon reintroducing the biological system to ambient conditions.

A steady state temperature distribution derived by Kritikos, Schwan and other appears to describe the heat disposition pattern, as indicated in the equation herein below:

$$T = T_o + q_1(1 - e_o i_o(\sqrt{\lambda R})) - c_o i_o(\sqrt{\lambda R})$$

where $$T_o = \frac{q_o}{\lambda} [1 - \rho_1 + 1)e^{-\rho_1}i_o(\sqrt{\lambda R})]$$
$$0 > R > 1 \text{ cm}$$

$$T_o = \frac{q_o}{2\lambda} [(\rho_1 - 1)e^{\rho_1} + (\rho_1 + 1)e^{-\rho_1}]k_o(\sqrt{\pi R})$$
$$1 > R > 5 \text{ cm}.$$

The common solution to the heat transport equation is readily obtainable by the subsequent application of Green's function contained herein below:

$$T = \frac{1}{4\pi} \int_{0 \to \lim} G(R,R')q(r')dv'$$

The calculations utilize an analytic approximation for the heating potential rather than an exact numerical matrix. The analytic approximation are derived from their proper asymptotic forms which are more readily applicable in providing a means for efficiently handling numerous parameters of thermal conductivity and transport. With insertion of any heat potential distribution of q(r) into the integral a temperature profile is readily obtainable.

The Green's Function of the Heat Transport Equation $$(\nabla^2 - \lambda)G(R,R') = -4\pi\delta(R - R')$$

subject to the boundary conditions $$\frac{\partial T}{\partial R} = -\alpha T - \alpha(T_{bl} - T_{sk})$$

is given by $$G(R,R') = \sqrt{\lambda} \, \Sigma_{m,n}(-1)^n [Y^e_{m,n}(\theta',\phi')Y^e_{m,n}(\theta,\phi) +$$

$$Y^o_{m,n}(\theta',\phi') \, Y^o_{m,n}(\theta,\phi)] \, [i_n(\sqrt{\lambda} \, R)k_n(\sqrt{\lambda} \, R) -$$
$$< \quad >$$

$$A_n i_n(\sqrt{\lambda} \, R')i_n(\sqrt{\lambda} \, R)]$$

where $A_n = \dfrac{gk_n(\rho) + k_n'(\rho)}{gi_n(\rho) + i_n'(\rho)}$

Further indicated herein are a series of values of $i_n$ and $k_n$ which are indicative of Modified Spherical Bessel Functions having the following properties:

$$i_n(r) = i^n j_n(ir)$$
$$i_n'(r) = i^{n+1} j_n'(ir)$$
$$k_n(r) = -i^n h_n(ir)$$
$$k_n'(r) = -i^{n-1} h_n'(ir)$$
$$i_o(r) = \sin h(r)/r$$

$$k_o(r) = \frac{e^{-r}}{r}$$

-continued $$i_1(r) = \frac{\sin h(r)}{r^2} - \frac{\cos h(r)}{r}$$

$$k_1(r) = \left(\frac{1}{r} + 1\right)\frac{e^{-r}}{r}$$

$$-i_{n-1}(r) + i_{n+1}(r) = \frac{2n+1}{r} i_n(r)$$

$$-k_{n-1}(r) + k_{n+1}(r) = \frac{2n+1}{r} k_n(r)$$

$$i_n'(r) = -i_{n-1}(r) - \frac{n+1}{r} i_n(r)$$

$$k_n'(r) = -k_{n-1}(r) - \frac{n+1}{r} k_n(r)$$

$$i_n(r)k_{n-1}(r) - k_n(r)i_{n-1}(r) = \frac{(-1)^n}{\rho^2}$$

$$i_{n+1}(r)k_{n-1}(r) - k_{n+1}(r)i_{n-1}(r) = (2n+1)\frac{(-1)^n}{r^3}$$

$$Y_{m,n}^c(\theta,\phi) = \sqrt{\frac{\epsilon m(2n+1)(n-m)!}{4\pi(n+m)!}} P_n^m(\cos\theta)_{\sin m\phi}^{\cos m\phi}$$

$$\epsilon_m = 1, m = 0; \epsilon_m = 2, m \neq 0$$

The Rayleigh Region $kA << 1$ is a region wherein heating is performed by electrical and dipole mechanisms. The magnetic dipole heating is crucial in larger spherical areas corresponding to regions in excess of 2.25 cm, whereas electric dipole heating is accomplished almost exclusively in smaller regions ($k = 2\pi/\lambda$, where $\lambda$ is equivalent to a foe space wavelength and A is equivalent to the radius of the sphere). The effects of heating for the Rayleigh Region according to Schwan. Kritikos is presented in brief in the equations contained herein below:

The solution is readily obtainable from low frequency approximations to the heating potential which is indicated by the value $\Delta S$, $$\Delta S = \sigma \left|\frac{E}{E_o}\right|^2 1.20 \pi \text{ in cm}^{-1}.$$

indicating the heat generated per unit volume (cm$^3$) per incident power density $|E_o|^2$ (watts/cm$^2$). This quantity is essentially equivalent to the specific absorption rate SAR electric field is given by $$E = \frac{i\omega R}{2c}[x\cos\theta - z\sin\theta\cos\phi] - i\frac{3\epsilon_o\omega}{\sigma} x.$$

where the first term is due to the magnetic dipole, and the second due to the electric dipole.

Substitution of the preceding equations yield $$\Delta S =$$

$$\frac{\omega^2 R^2}{12 c^2}\left(2\sqrt{4\pi} Y_{0,0} + \sqrt{\frac{4\pi}{5}} Y_{2,0} + \frac{1}{2}\sqrt{\frac{48\pi}{5}} Y_{2,2}\right) +$$

$$9\frac{\epsilon_o\omega^2}{\sigma^2}\sqrt{4\pi} Y_{0,0} - 3\frac{\epsilon_o\omega^2}{\sigma c}\sqrt{\frac{4\pi}{3}} Y_{1,0}.$$

The SAR is the specific electromagnetically generated heat production in a region of tissue, expresses in W/kg of body weight. Since the SAR is not normalized by the incident field intensity, it is necessary to specify this parameter. The heating potential $\Delta S$ is the local heat generation per cm$^3$ of tissue (in watts/cm$^3$) divided by the incident field intensity.

Figure 10:
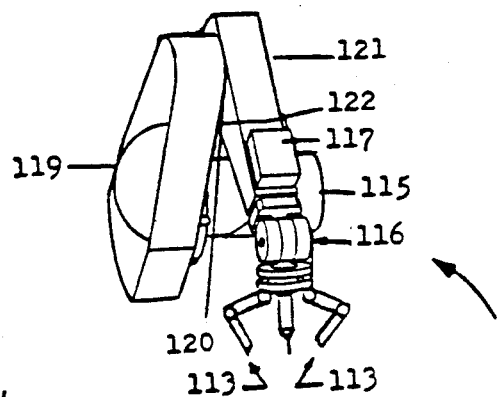
FIG. 10 through 10b are detailed perspective views of three equivalent injection servos utilized to administer profusiates, metabolic stablants and the like to organs or whole biological systems.
Figure 10A:
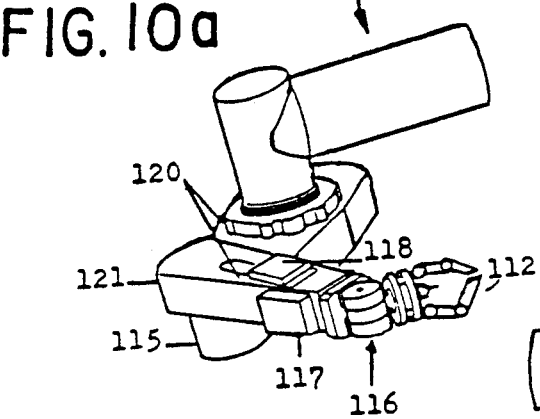
Figure 10B:
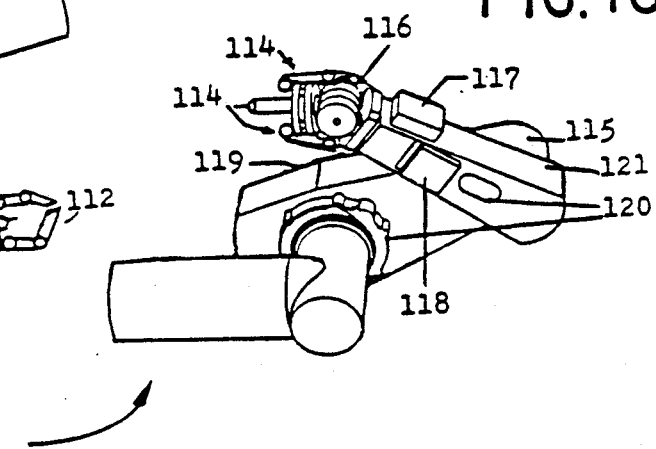

FIGS. 10 through 10b are detailed perspective views of three equivalent automated injection servo means utilized to administer profusiates, metabolic stablants and the like to organs of a biological system or the equivalent to the circulatory tract profusing organs of said organic system. Numerals 112, 113 and 114 are indicative of articulating manipulators, a retractable hypodermic syringe delivery means and an extender/retractor unit for the delivery means. The manipulators numeral 112 are powered by a piezoelectric engine means, which are described by number 115, which also provides 360° angular rotation for artifical wrist means 116, inclusive. Ancillary component part of the hypodermic means are contained within compartments 117. A complement of reserve hypodermic syringe means for replacement of damaged or expended units rendered inoperative are contained within unit 118. A supply magazine containing secondary reservoirs of profusiates, metabolic stablants, anti-shock recursives and/or additional means is collectively described by element 119. A secondary rotating junction means is indicated by numeral 120, which provides horizontal 360° rotation for the robotic arm means 121; whereas vertical rotation for the said robotic arm means is additionally provided by unit 122. The automated means becomes actuated only when the biologicals are entering cryogenic suspension and/or leaving cryogenic suspension, just prior to being reintroduced to ambient conditions of temperature and pressure (STP).

FIGS. 11 through 11b are detailed sectioned views of the hypodermic means utilized to inject profusiate, metabolic stablants and the like. Located at the most anterior portion of hypodermic syringe means 126 is a graduated hypodermic needle 123 composed of a plastic composite material with a low expansion coefficient. A rotatable articulating joint means number 124 provides a 360° rotation in the horizontal plane and 180° translation in the vertical mode. The aforementioned articulating joint means is positioned by a series of eight miniature solenoid means which are collectively indicated by numeral 125. The solenoids depending on which of the complements are activated provides a given angle to hypodermic needle means 123, and then locks it into position. The syringe numeral 126 is composed of a commerically available elastic, crack or fracture resistant to extremes in temperature and pressure. A pneumatic sleeve described by numeral 127 circumferentially encapsulates syringe means 126, providing uniformed pressure to said syringe means. The syringe is compartmentalized such that compartment 128 contains a specified profusiate and compartment 129 contains a specified metabolic stablant or the like. Each fluid media contained in both compartment 128 and 129 remains separate and distinct until united in mixing chamber 130. Two circumferential variable orifices 131 and 132 control the flow from the compartments 128 and 129 into the mixing chamber 130. An additional compartment, 133, is provided for aspiration or suction of blood, or the subsequent withdrawal of profusiates from the biological system, 141, when required. Compartment 133 is also provided with a variable orifice means 134, which remains closed until signaled electronically. The content of each compartment is additionally placed under positive or negative pressure (i.e. aspiration of blood or profusiate back to a storage vessel or reprocessing unit). Lines 135 through 137 provide the conduits to convey contents going or retrieved from compartments 128, 129 and 133 respectively. Pressure gaskets are indicated in part by elements 138, 139 and 140.

The primary application of specific energy fields of an exact electronic nature, oscillatory rate and intrinsic resonance pattern in conjunction with the introduction of dynamic fluid parameters altering the colligative properties of biological systems is a unique and novel implication of the cryogenic suspension means described in the invention. During the first mode of operation the biological system is profused with a dilute solution of profusiates consisting of combinations of a GPF and NPGF in the presence of increments in pressure and declination of thermal kinetic parameters. Additionally, the isotonic volumes of cellular components are successively reduced by a factor of $\frac{1}{8}$ to $\frac{2}{3}$ of their original ambient state. The intrinsic vibrational frequency rotational state and dipole moment for a specified aqueous medium is electronically discern with regards to the specific circumstances, wherein nucleation of ice crystals have a high probability of forming, aligning as well as propagating in any given biological solution. A sonic field oscillation at a specific frequency inhibiting the nucleation process by effecting crystallization or alignment on a molecular level is implemented in a precise manner. Further the sonic beam transmission expedites the uniformed dispersal or distribution of chemical species (PGF/NPGF profusiates, metabolic stablants, electrolytes and the like) throughout a given biological solution by the simple process of molecular agitation. Ideally the application of sonics initially occurs at a temperature range which closely approaches the nucleation temperature and appropriately is continued through the vitrification temperature; however the practical application of sonics occurs over a much larger temperature range ($<T_c \rightarrow T_g>$). The sonic energy spectrum is emitted cojointly with the administration of various chemical species which in and by themselves alter the colligative properties of the said biological system or solution.

The application of specific microwave laser and or radio-frequency emissions to a biological system upon its removal from cryogenic suspension is critical. The aforementioned biological system must acquire a uniformed increment in temperature of between a minimum of 200° C. to 300° C./min to a maximum of between 300° C. to 600° C./min depending on the size and complication of the system. Further pressure must be decreased at a given rate upon normalization of the biological system. The aforementioned administration of energy fields must be initiated and maintained with suitable electronic characteristics, oscillation rate and temporal mediation which inevitably accommodates the kinetic thermal absorption and relaxation time of the biological system on a cellular level. The said relaxation time being associated with a temporal interval wherein energy is affectively optimally dissipated and/or dispersed through the system, in order to avoid all lysing, the denaturing of proteins, enzymatic deactivation and the like due to excessive thermal retention. Additionally, reactive gaseous components such as molecular nitrogen and oxides of nitrogen and carbon, (carbon monoxide, nitrogen oxides), or their equivalents are removed or displaced by other gases. Metabolic stablants, electrolytes are replaced or added to compensate for those lost or decompensated for, in the cryogenic process. The rapid rise in temperature essentially prohibits the devitrification process. The time interval of thermal kinetic excitation is limited to a temporal interval of one minute with an optimal elevation occurring in a range not to exceed 40 seconds in most instances. The equations previously explicitly mentioned or indirectly alluded to in the foregoings provides the optimum parameters in which all energy system must operate.

The readministration of temperature and pressure labile enzymes, vitamins and in larger systems antishock precursor are crucial to the reactivation of metabolic and other organic processes which are necessary for sustaining viability of the said system. Additionally when whole blood for a single complexed organism was withdrawn it must be reprocessed and readministered to the vary same said organism. Previously inhibited oxidation phosphorlative processes, phospholipid metabolism and other support processes are of prime importance in order to evade cellular stravation, oxygen deprivation and the build up of indogenous toxic wastes such as, carboxysilatic acid, lactic acid, pyruvic acid, phenyl amines or other potentially lethal substances. The totality of all the aforementioned substances are optimally administered to complicated biological systems by infusion of said substance which is injected into the circulatory tract of a given system.

Preliminary experimental evidence indicates that in large intact biological systems (i.e. dogs or higher order mammals) sustained at temperatures below freezing ($<22°$ C.$\rightarrow 0°$ C.) for extended durations (24 to 48 hours+) often must undergo recursive normalization upon their recovery period wherein the complexed systems are reintroduced to ambient conditions. A number of complications arising from cryogenic suspension must be rectified in order to normalize the intact organism to conditions or parameters, which have existed in the organism prior to its introduction to the said suspension process. The aforementioned complications arising from cryogenic suspension consists of in part but not limited to prolonged constriction of vessels, partial collapse of respiratory tissues and decompensations in the acid/base metabolism, pH, levels of electrolytes and the like. Constricted vessels as in the distinct case of arterioles supplying the brain or arteries servicing the heart must be rectified within the first few minutes to hours of the recovery period in order to avoid damage to sensitive tissues such as, cardiac, nephritic or neurological tissues due to oxygen deprivation. A synthetic commercially available surfactant known as Fluosol-43, acts as a high density, non-toxic carrier of oxygen that is somewhat less viscous than whole blood.

Upon oxygenation the Fluosol infusion is immediately followed by whole blood. A Harvard type of respirator is employed if the organism is subjected to pheumothorax wherein a lung is either partial or totally collapsed. Whole blood which is placed in storage and subjected to variances in temperature, pressure, or chemical degradation undergoes decompensatory imbalances in pH, fluid and electrolytes. Fluid and electrolytic imbalances are readily restored by the application of dialysis and a regimen of commericially available diuretics. The administration of saline solutions, preparations of sodium bicarbonate, and positive ion complexes containing hydrogen can rapidly facilitate the removal of dangerous variances in pH alluding to decompensations due to acidity, the presents of excessive bases, or the like within the blood stream of a given organism.

Figure 12:
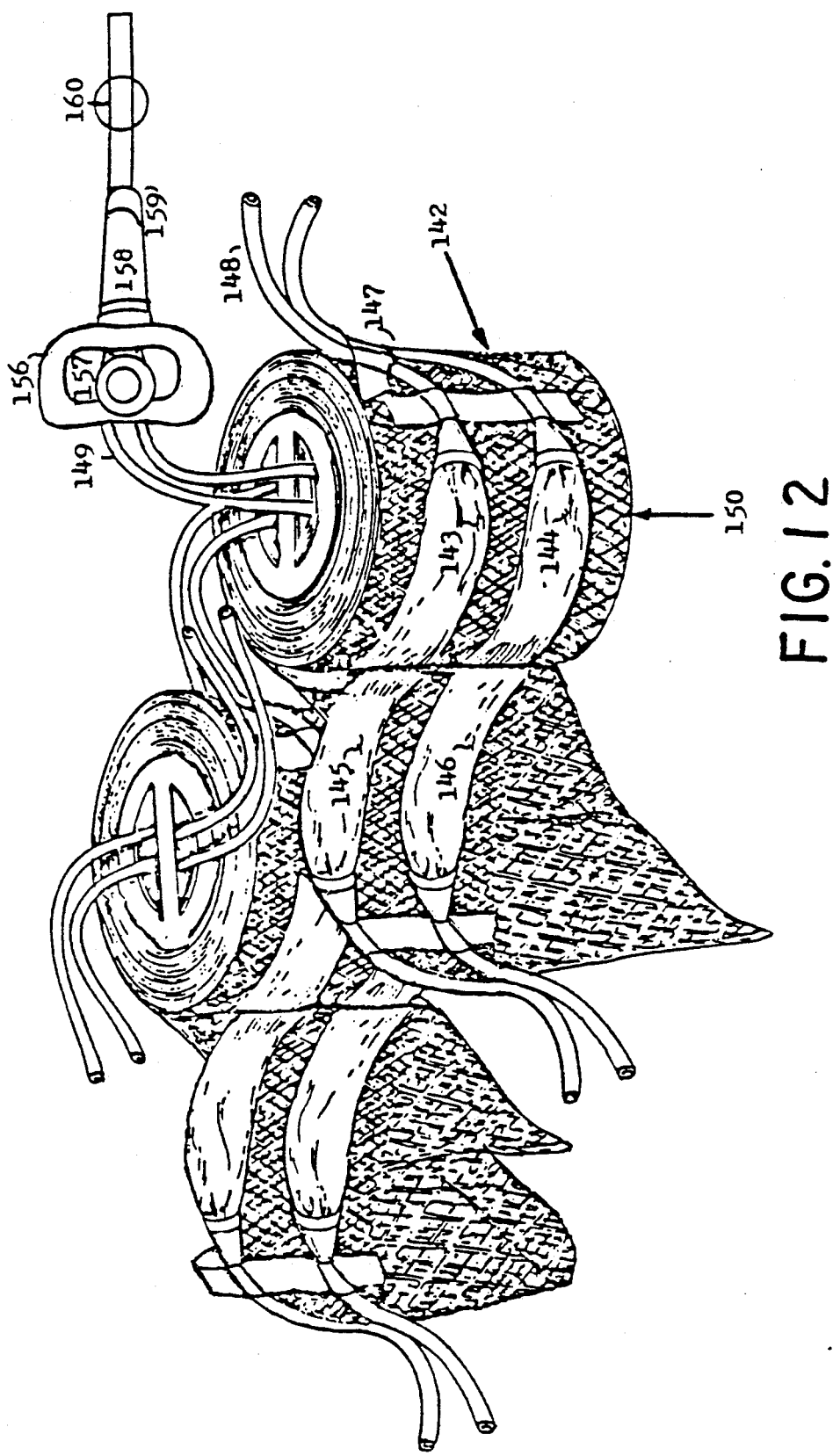

FIGS. 12, 12a entail a pictorial and schematic view of a dialyzer means utilized to maintain the balance of chemical species, stablized fluid levels as well as to remove excess residual waste in the blood of an intact organism during and immediately following the recovery period. Numeral 142 denotes a single element of a multiple equivalent pair coil dialyzer means each of which is formed by winding multiple cellulose tubes together elements 143 through 146. The cellulose tubes are bound together by a scrim numeral 147 thus forming two pairs of dual blood flow paths 148 and 149 which are taken in parallel. The thickness of the cellulose membrane providing structural interface is approximately 25 micrometers, with the diameter of the tubing ranging between 45 and 50 millimeters and the total surface area for each of the equivalent coil means ranging between 0.9 to 1.9 square meters. The membrane composed of cellulose or some similar such material is rendered semi-permable having multiple pores averaging 40 Å which allows waste by-products such as urea, creatinine, uremic and pyruvic acid to exit the system by a concentration gradient and the countercurrent phenomenum, while simultaneously retaining large molecules of proteins, cells and the like by processes well understood by those skilled in the art. Each of the coils are encapsulated in a separate canister as indicated in part by numeral 150, which are then collectively enclosed in a tank. The dialysate medium optimally consists of an aqueous fluid containing electrolytic concentrations corresponding to those found in the ambient levels located in the blood of a given intact biological system prior to its introduction of conditions of cryogenic suspension. The dialysate is actively pumped through the coil axially as is the blood for the arterial side with the coil complement having a high resistance to whole blood and providing optimal conditions for hemodialysis of electrolytes and the like. Access to the dialyzer from the blood supply is accomplished through microcannulations to given arteries a and adjacent veins. A variation of the Scribner-Quinton shunt, silastic shunt, which is implanted between the radial artery and the adjacent subcutaneous vein facilitates access to the hosts blood without the neccessity of surgical implants. The aforementioned shunt means is illustrated in part by a schematized pictorial depicting the dialyzer unit 151 penetrating radial artery 152 and subcutaneous vein element 153. The preparation of the dialysate and monitoring means are indicated by numeral 154 and 155. Flow from tubules are under the control of flow governors. A single flow governor is indicated by element 156, with a flow sensor being denoted by means 157 and a graduated operative solenoid being depicted by unit 158 which directly controls the diameter of the orifice leading to a given graduated tubule 159 and 160.

Figure 13A:
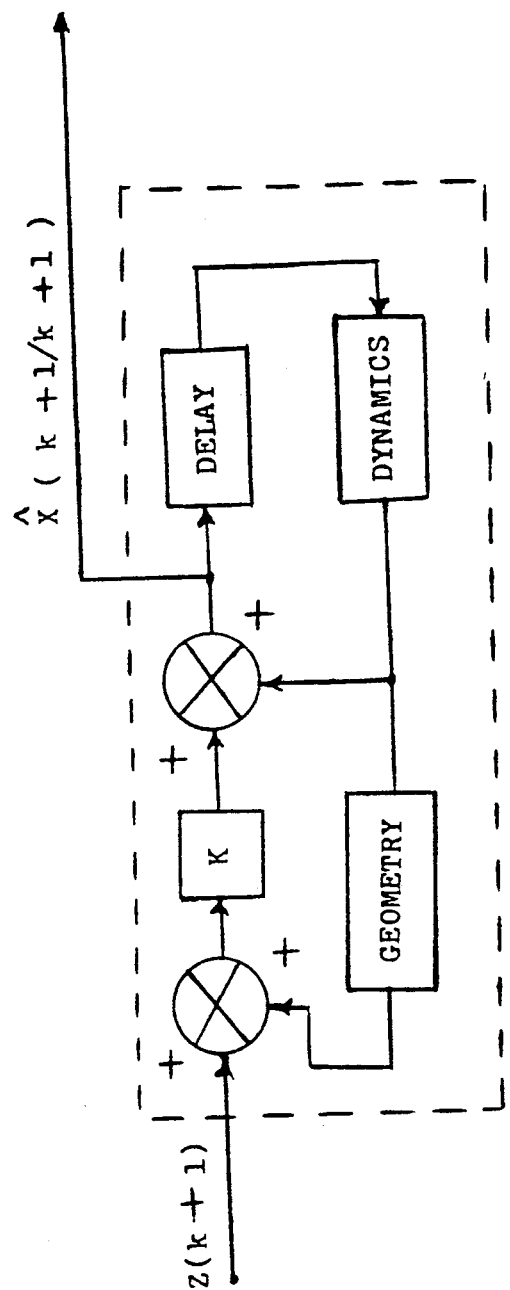
FIG. 13a is a concise schematic view of said dialyzer complement interfaced with a given specimen.

FIG. 13 is a concise simplified schematic representation of the dialyzer complement including partial ancillary support systems. Numerals 161, 162 and 163 represent the dialysate tank, circulating pump and drain pump means. Elements 164 through 168 denotes a combination blood transfuser pump complex, a regional heparinzation unit, a aspiration unit and a venous/arterial monitoring system. Extracorporal blood pressure, a blood leak detector, the temperature, pressure, flow and concentration of the dialysate are collectively designated by elements 169 through 174 and contained within a feedback loop element 175.

Figure 14:
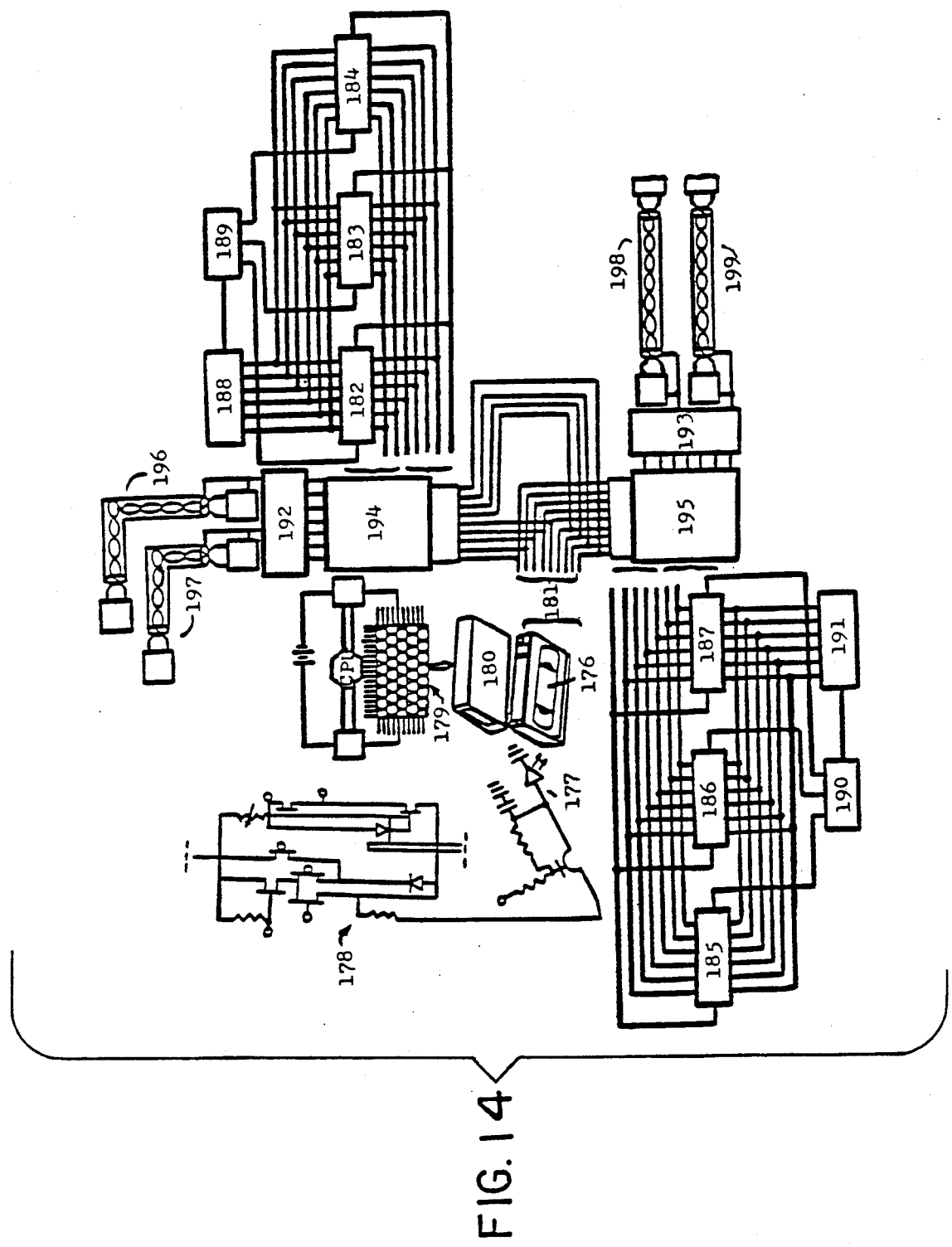

FIG. 14 illustrates in part a simplified version of an electrophoretic laser sensor means which is utilized to monitor the intrinsic levels of ions, solutes and the like. This figure in the form of a partial block diagram denotes a single continuous flow microcuvette analyzer complex. Each microcuvette analyzer complex of which there are several is associated with an equivalent reference complex with measurements from each taken nearly simultaneously and then cross-referenced in order to identify various substances on the basis of their intrinsic or characteristic absorbance, transmittance, re-emittance and their electric motility. An inert transparent cuvette described by element 176 is bombarded by a specific emissive wavelength from a complex of miniature laser diodes which are indicated by numeral 177. This in turn is associated with a number of single substrate optical electronic systems which are described by the single numeric value 178. Each cuvette element is fitted with a suitable electrophoretic gel composed of Sephadex G-70 or other suitable equivalent commercially available gels, which are capable of providing identification of substances via electro motility as indicated by 179. Each cuvette element is also provided with a series of reservoir structures equipted with electro-optical elements, which are assigned collectively the numeric value 180. Certain specific chemical species blood porphrins, metabolic stablants and the like when acidified and subjected to laser emissions occupy unique positions located on electrophoretic gels. Wavelengths are readily altered by such frequency doublers as sodium potassium niobate, $Ba_2NaNb_5O_{15}$, lithium iodate, keyed to a specific substance which induces florescence for certain specified compounds in the presence of acidified solution. Such said substances capable of undergoing florescences range from $\alpha$-adrenergic substances to a variety of porphyrins structures. The same said substances have characteristic absorptance and transmittance which are monitored by an array of miniature laser diodes, not shown, each of which is responsive to a given wavelength. The entire cuvette unit is encased by a protective capsule designated by element 180, which acts as an optical emissive port. Electro-optical signals are conveyed along bi-directional fiber optics unit 181 to and from the cuvette proper. Electro-optical signals received from the sensor diode array are compared against a repertoire of digital signals obtained from known substances of familiar concentrations. Data is matched on the basis of a well known statistical format defined by the Best Fit Least Means Square Technique and variations of Bayes Maximum Likelyhood Method of statistical inference of incoming digitized signals which are compared against known values. The known values and search procedures are encoded in an array or complex of microprocessor means or their equivalents which act on a series of comparators designated by elements 182 through 187. Elements 188 through 191 designate units which statistical formats and priority selector means. Optical electronic converter unit means are assigned the numeric values 192 and 193, while the electro-optical digitizer means are assigned the numeric values 194 and 195 respectively. Informational input from other equivalent systems and output signals from the aforementioned system are exchanged and feed into a microcomputer array or its equivalent via bi-directional means numbers 196 through 199.

Figure 15:
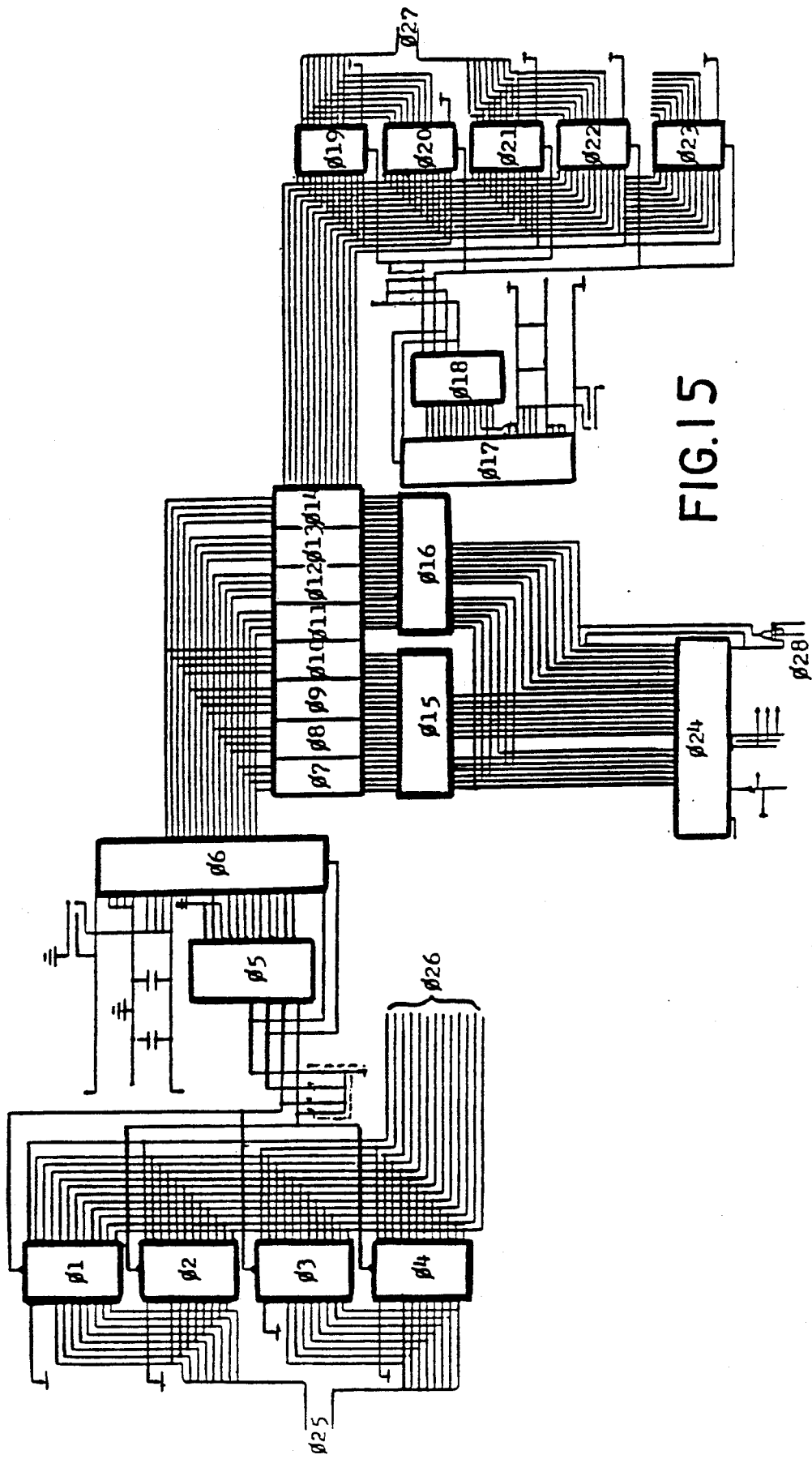
FIG. 15 is a concise simplified diagram schematic version of a pulse shaping/timer circuit typical of those deployed by the capsule device.
Figure 16:
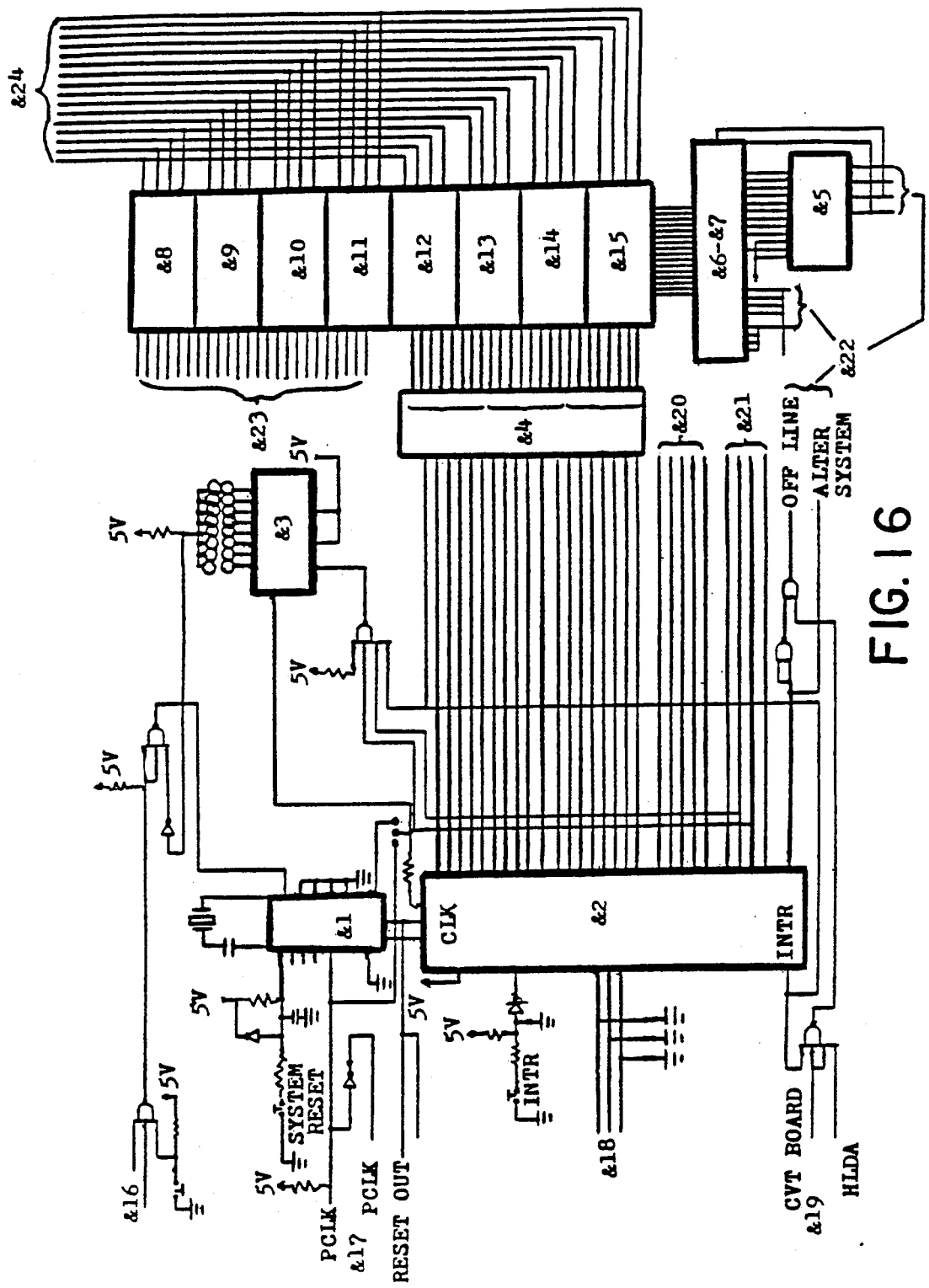
FIG. 16 is a partial circuit diagram which designates only one of several oscillator circuits or sequencer means that are deployed into the solid state capsule.
Figure 17:
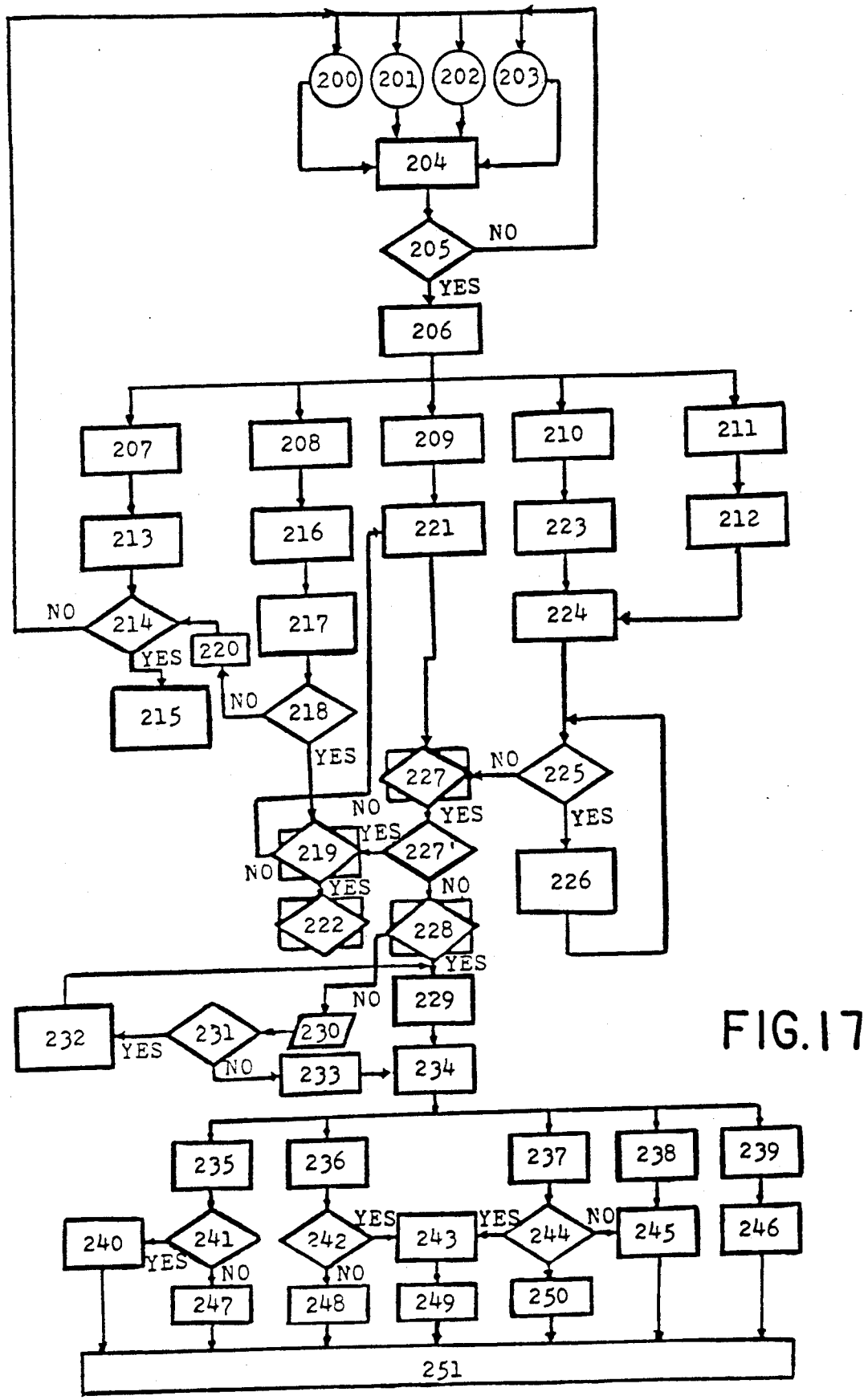
FIG. 17 a concise simplified flow diagram which illustrates in part only a fraction of an expert program or system illustrated in this invention.

FIG. 15 is a greatly simplified diagram schematic version of a pulse shaping/timer circuit typical of those deployed by the solid state capsule device. The mere act of placing a biological system in an unspecified ultrasonic oscillation field is self defeating since the improper use of sonics can be injurious to cellular and subcellular structures, agitating the said structures to the point of molecular disruption. In order to prevent cellular decompensation due to molecular disruption an exact frequency, oscillation rate and pulse width or shape must be chosen on the basis of impeding nucleation at the nucleation temperatures($T_n$) and devitrification interval ($T_c$); without effecting any of the molecular structures. Specifically only the vibrational, translational and axial rotation frequencies or periods are effected by the ideal application of sonic field resonance. The pulse electronic characteristics are decisively shaped on the basis of information retrieved from sensors monitoring the aforementioned biological systems. The subsequent uniformed dispersal of chemical species such as base profusiates, metabolic stablants and the like is facilitated by a non-deleterious agitation of the said species on a molecular level. The basis or criteria for intrinsic rotational, translational, vibrational frequencies and the like are indicated by return signals from the said biological systems and a series of expert programs or systems based on statistical inference and mathematical parameters which are well known by those skilled in the art. What is actually shown in part in FIG. 15 is a simplified schematic representation of a logic circuit which forms the basis embodiment of a single microcomputer means. The vital portion of the circuit as shown in the figure is equivalent to a multitude of other similar such circuitry utilizing VLSI/VHSIC technology. The separate I.C. elements are so constructed as to be repetitive providing a reliable microcomputer with an increased ability to calculate and implement parameters concerning electronic wave characteristics, oscillation frequencies, resonant patterns and the like. The I.C's are disposed on a single portion of the VLSI card which is replaceable in itself as are each of the integrated circuit (I.C.) means. Each integrated circuit is designated by its own alphanumeric value and there are twenty-four I.C.'s which are listed by elements ϕ1 through ϕ24. Elements ϕ15 and ϕ16 act as logic interragators for elements ϕ7 through ϕ14. Comparator means for data are indicated in part by elements ϕ1 through ϕ4 as well; as elements ϕ19 through ϕ23. Alphanumeric values ϕ25, ϕ26, ϕ27 and ϕ28 are indicative of origins of embarkation wherein data either enters from other circuits or leaves from the portion of circuits depicted in this figure bound for other circuits. Other portions of the partial circuit diagram depicting capacitors, grid, resistive elements and the like are straight forward to those skilled in the art and therefore not assigned any alphanumeric values.

FIG. 16 is a partial circuit diagram designating only one of several timing oscillator circuits or sequencer means which are deployed by the solid state capsule. This figure denotes a slight basic variation of a readily available circuit which can be provided by companies such as Intel, I.B.M. or equivalent circuits by others. The circuit predisposes the operation of logic the circuit described by FIG. 15. The key integrated circuits are assigned the alphanumeric values of & 1 through & 15. Elements & 16 through & 24 are indicative of I/O from other circuits. The capacitance, diodes and resistive elements are readily understandable to those skilled in the art and are not assigned alphanumeric values for the sake of simplicity.

FIG. 17 is a concise simplified flow diagram illustrating in part only a fraction of the expert program or system utilized to promote viability of a biological system placed in a state of cryogenic suspension or its subsequent recovery from the said state. Numerous fields today are attempting to procure expert systems, for example such programs are presently available for geological surveys, medical diagnosis, global war strategies and other disciplines. An expert system basically consists of a program format of a series or sequence of coded responses to events which are based on the response deduced from the rational of leading experts in the field. The flow diagram denoted in FIG. 17 represents only a single multiple feedback loop representative of several thousand similar such loops. The flow diagram is based on information compliled by such commercially available sources as Control Data Corporation, subsidaries of I.B.M. and other companies in the field. A typical program requiring a medical expert system can involve inexcess of 80,000 programming steps. Alterations of biological and environmental parameters such as temperature, pressure, pH, osmality and the like are considered to be events which can elicit a number of compensatory responses specified by a given format which consists of a number of activities such as the release of metabolic stablants which must be executed. So what is represented in FIG. 17 is a basic outline of a single element of a single expert system utilized to maintain the viability of a single biological system or entity. All events are monitored by a series of online sensors which are keyed to a specific event and each event has a secondary and ternary event consequences. Sensor elements 200 through 203 provides accurate measurments of event horizon number 204. If the event 204 can actuate an event domain, as described by numeral 205 an event vector can be ascertained, as indicative by element 206; if not the system is automatically programed to return to a scanning procedure of the event horizon, which is designated by numeral 204. Depending on the magnitude of the event vector obtained, a series of actions can be elicited and defined by elements 207 through 212. If the event action numeral 213 can be executed, then the program procedes to a determination process, as described in numeral 214. If the determination process can be ascertained, then an appropriate action can be elicited, wherein compensatory actions are performed in order to maintain a biological system viability, as indicated by numeral 215; if no then the program is returned to the scanning elements described by numbers 200 through 203 for repetitive analysis.

The data from the event vector 206 may establish criteria 208, which in turn elicits a computational matrix 216; which then issues a command to execute a bit by bit initialization sequence, as defined by numeral 217. If a constructive discussion can be rendered on the validation of data delivered from initialization then the data can be further processed by a verifier circuit, indicated by numeral 218, if not the data is sent to a recycling station 220 which feeds into element 214 and which eventually may be deleted as being a erroneous signal. A verified signal activates another processing center numeral 219 wherein further compensatory processes can be exacted with all non-correlatable data providing a null set, which is intrinsically set to a dump cycle as defined by element 221, which is committed to short term memory in order to be acted upon by higher order processes for further analysis as prescribed by numeral 222. If it is determined that the data obtained from the event vector 206 indicates the biological system is in a state of dynamic flux, as determined by element 210, then rapid scanning and timing parameters in all circuits must be set accordingly, as defined by element 223. Even a system in dynamic flux must almost continuously sample all parameters, as indicated by element 224. If what is being sampled from the sensors 202 and 203 is some chemical parameter with a complexed wave pattern or decay rate than decision means 225 determines that a secondary event is in progress, as described by element 226 which re-enters the system for re-determination by element 225. If however, no decision can be rendered other than a complexed electronic wave pattern which is present then the digitized signal enters a run cycle, as indicated by numeral 227. In the run cycle the timing parameters are reaccessed by element 228 which enters a additional decision process that determines whether or not a third event is in progress, as described by element 229, if not the data is sent for reprocessing, as described by numeral 230. From reprocessing a digitized signal as per ordered statistical analysis is provided by element 230 which elicits an appropriate compensatory response, which is denoted by element 231. The system automatically resets, as indicated by element 232 after the given compensatory response is completed. In the event a ternary event is present such as alterations in osmality in relation to variations in pH, temperature and/or pressure with an additional processing element that is indicated by numeral 233. The processing element 233 elicits a subprogram, which is described by unit 234. Numerals 235 through 239 predisposes five separate subroutines that are utilized to execute a number of compensatory actions based on the digitized signal sent by the subprogram element 234. Each of the subroutines is input specifically, that is to say each separate subroutine is actuated by only a five coded digitized signal and it remains deactivated by any other coded signals. Numeral 235 represents a single first order increment delivery system, numeral 236, which describes a delivery means varying by 10 orders of magnitude; whereas element 237 specifies logarithmic dispersal. Numeral 238 designates a subroutine indicative of other specialized functions such as squares and proportionately constants; whereas number 239 denotes a subroutine responsive to other processes. Numerals 240 through 246 designate re-iterative processes of comparison to known values or norms associated with interrogators and decision making processes. Finally elements 247, 248, 249 and 250 describe a series of procedures or activities which are to be executed in order to drive certain given systems. The results of each are recorded in the memory of the microcomputer to then by reaccessed by higher order functions as indicated by numeral 251, and all processes are reset unless specified otherwise. This can be readily seen by those skilled and unskilled in the art of expert systems with the complexity and extent of writting such a program quite a formidable task. The entire expert systems program consists of a format of if-then rules or heuristic reasoning which form the basis of decision making processes acquired from the knowledge obtained and compiled from one or more human experts.

Figure 18:
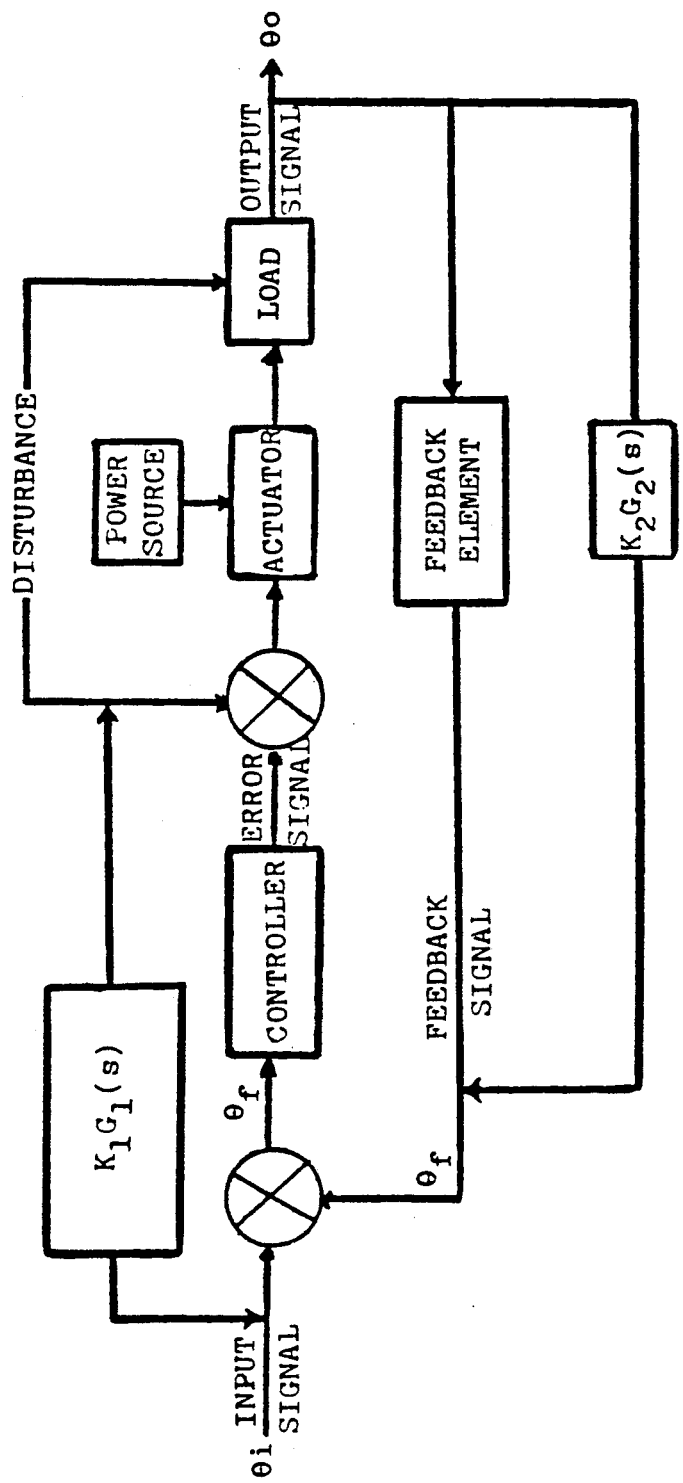
FIGS. 18, 18a are block diagrams denoting the basic design of automated servomechanisms contained within feedback loops embodied within said invention.
Figure 18A:
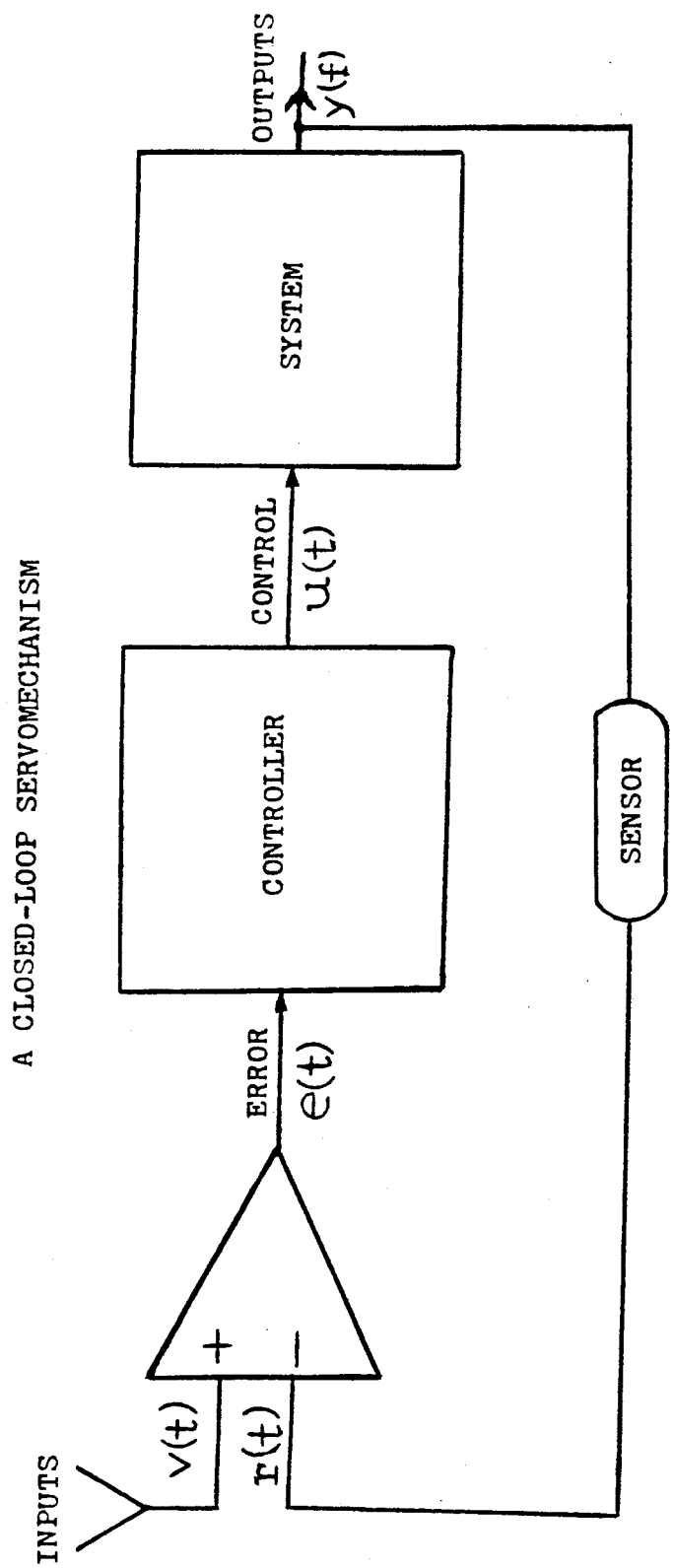

The basic design of the automated servomechanism system contained within the feedback loop can be best illustrated by the block diagrams disclosed in FIGS. 18, 18a.

A discrepancy of disturbance is generally detected by sensors, $\theta i$; which sends their digitized signals to a comparator means, which acts as an error detector. The error signal, $\theta E$, is sent to a controller means which elicits an actuator means (which is provided with a power source and) generates a load leading to an output signal, $\theta o$. Additional information is being supplied and the output signal, $\theta o$, generates additional data impulses, which enters a feedback element relaying in this case perhaps the position of the turret in relation to a target vector, which then exacts a feedback signal, $\theta f$. The feedback signal, $\theta f$, is reassessed against an error detector, which reenters and completes the loop. Further contained herein below are a series of a standard simplified equations describing in general the control system transfer functions ranging from open loop to closed loop transfer functions listed in part herein below:

The forward transfer function is defined by the equation:

$$\frac{\theta o(s)}{\theta \epsilon(s)} = K_1 G_1(s)$$

The forward transfer function $K_2G_2(s)$ is defined by the expression:

$$\frac{\theta_f(s)}{\theta o(s)} = K_2 G_2(s)$$

The open loop transfer function, the product of the forward and feedback transfer function is defined by the expression:

$$\frac{\theta_f(s)}{\theta_\epsilon(s)} = K_1 K_2 G_1(s) G_2(s)$$

The error transfer function is designated by the expression:

$$\frac{\theta_\epsilon(s)}{\theta i(s)} = \frac{1}{1 + K_1 K_2 G_1(s) G_2(s)}$$

Closed loop transfer function is illustrated by the equation:

$$\frac{\theta o(s)}{\theta i(s)} = \frac{K_1 G_1(s)}{1 + K_1 K_2 G_1(s) G_2(s)}$$

Figure 19:
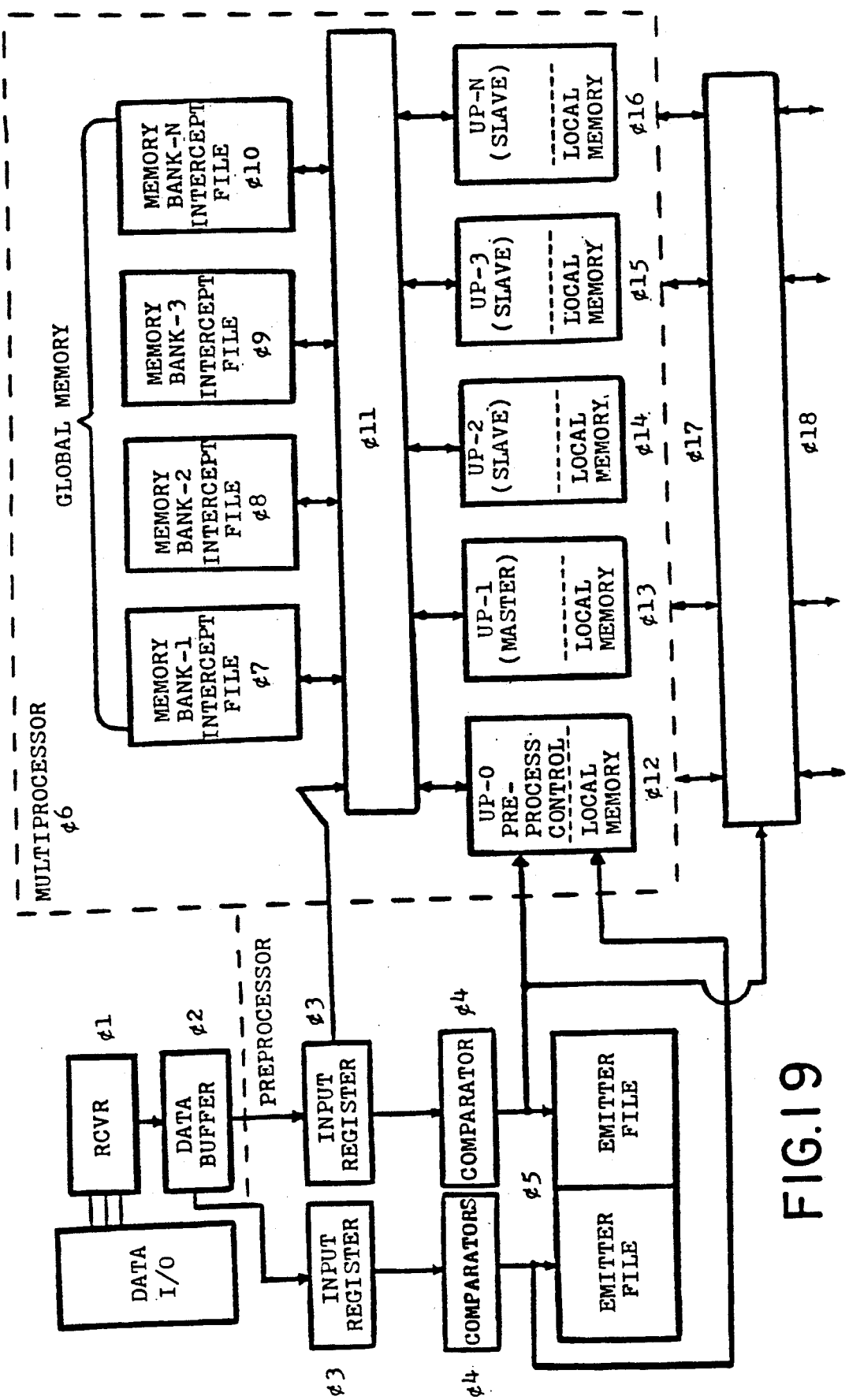
FIG. 19 is a structural diagram illustrating the structure of a global memory system encoded within microprocessors embodied within said invention.

It should be reitterated that the above mentioned equations are general and standard and only in part briefly outline the feedback loop employed in this patent disclosure. The simplified block diagram described in FIG. 19 illustrates in an exemplary fashion a microcomputer array processor element dispositied on a single VHSIC card. Information is received and encoded by element c1, which sends the data to be buffered by c2. The data obtained from c2 is then conveyed to a series of serial input registers, as denoted by element c3. The data from c3 is sent to a comparator bank, described by c4, which either processes the data by sending it to an emitter file c5 or to a series of interrogator circuits. The microcomputer array processor means is designated by value c6, which is contained within the embodiment of elements that are defined by a series of memory bank elements and intercept files, denoted by elements c7 through c10; wherein element c10 is a memory bank consisting of a number of subelements carried out to some desired element and all the elements c7 through c10 form what is losely known, as a global memory. Element c11 forms a typical memory request logic interrogator means and elements c12 through c16, which forms a preprocessor control local memory interrogator, a master control local memory and a series of slave memories with EEPROM capabilities. The processed data and preprocessed data are both entered directly into the systems computer controller means, as defined by embarkation point c17 and c18.

Embodied within the structure of the global memory system are integrated circuits or microprocessors which are responsible for manipulating the data fed into the microcomputer, in accordance with the operative set of instructions provided here by the user. The instructions are keyed by the user and are provided within the operative framework of a digitized list or sequence forming a program, which is encoded and stored into the memory elements of the microcomputer. Each instructional element of a sequence of instructions consists of a specified number of bits averaging 256 bits of information, which is stored in one or more registers collectively called a memory address. The number of addresses of instruction sequences to be employed by the system is stored in order for the proper sequence in a program counter. A controller means usually receives the address of the new set of instructions from the program counter, which obtains the digitized data stored in the aforementioned memory address and transfers the said data to the instruction register. The way by which data is conveyed is by three separate and distinct communication channels, as designated by the address bus, the control bus and the data bus, respectively. The instructional address placed in the program counter is entered in the address bus which readies the storage means to yield or transmit the instructional data. A digitized signal or electrical impulse on the control bus enables the data to be transferred to the data bus means. An additional control signal conveyed to the instruction register is held, while the controller means decodes it and issues further digitized control signals to perform the given set of instructions. The instructions pertain to data stored in the data buffer and may be initiated by either some input device or in and from the memory. If the instructions perform a given operation the results of the said operation may be stored temporarily in the accumulator means; wherein upon completion of the same said operation the results are sent back to the specified memory address. The ALO and accumulator means are associated with a set of condition codes also known as flags, which function as single bit registers with each unit indicating something about the results about a given operation held in the accumulator means. When subprograms and frequent subroutines are embodied within a given program which requires several instructions in the same sequence are conveyed to adjacent memory addresses collectively defined as a stack means, which enhances the speeds in a given operation. The memory addresses forming the stack are separately addressed, as if only a single memory location and the address accessed is stored, in a means defined as the stack pointer. The stack pointer functions in a specific fashion as to allow the controller use only a single address to call for the entire stack.

Figure 20:
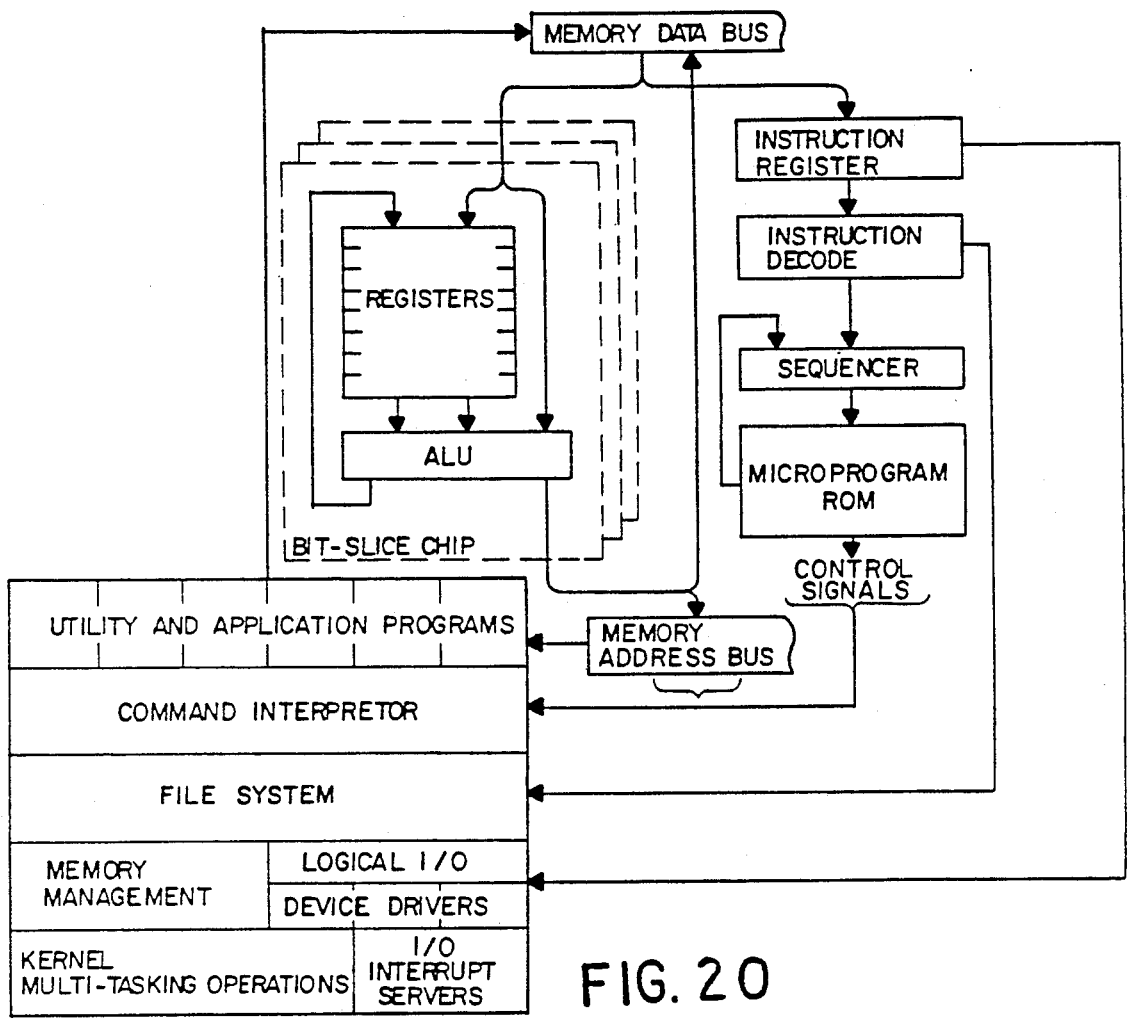
FIGS. 20, 21 are block diagrams illustrating the operations of the CPU and how said CPU transfers data.
Figure 21:
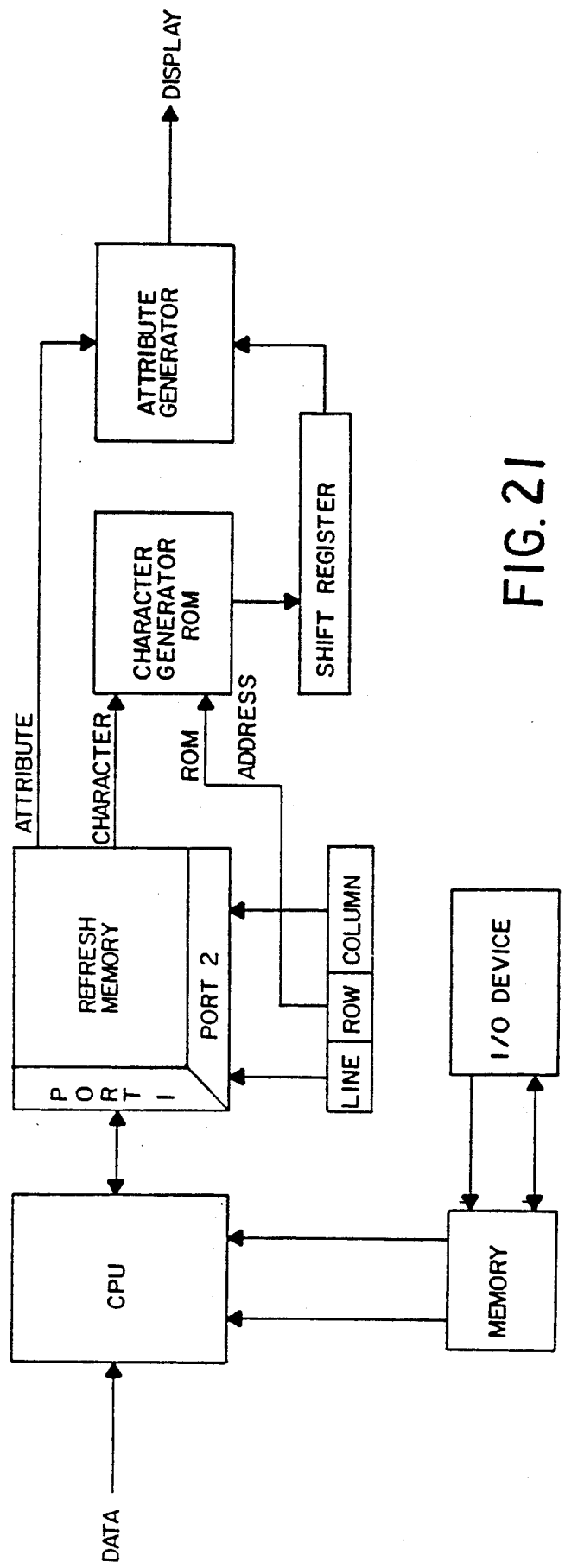

A series of other ancillary registers known as general purpose registers, which are used as required. The ancillary registers have or consist of a exact finite number of registor elements n, begining with an accumulator and ending with a high order byte register and a lower order byte register means. Other means are disposed in the form of external connections including a clock, power supply, data input/output means, analog/digital converters and other means. The CPU is implemented with secondary memory devices, which are defined by such means as read only memories (ROM's). Random access memories (RAM), charged coupled devices (CCD's), or other equivalent means, embodied within such means as I.C.'s are etched or imprinted on a card along with the microprocessor. The above aforementioned operations of the central processing unit CPU and how the CPU transfers data are illustrated schematically by FIGS. 20, 21. Numeric values are not assigned to the elements in the figures because each element is clearly defined and staight forward, consistant with the operation of conventional computer systems.

Figure 22:
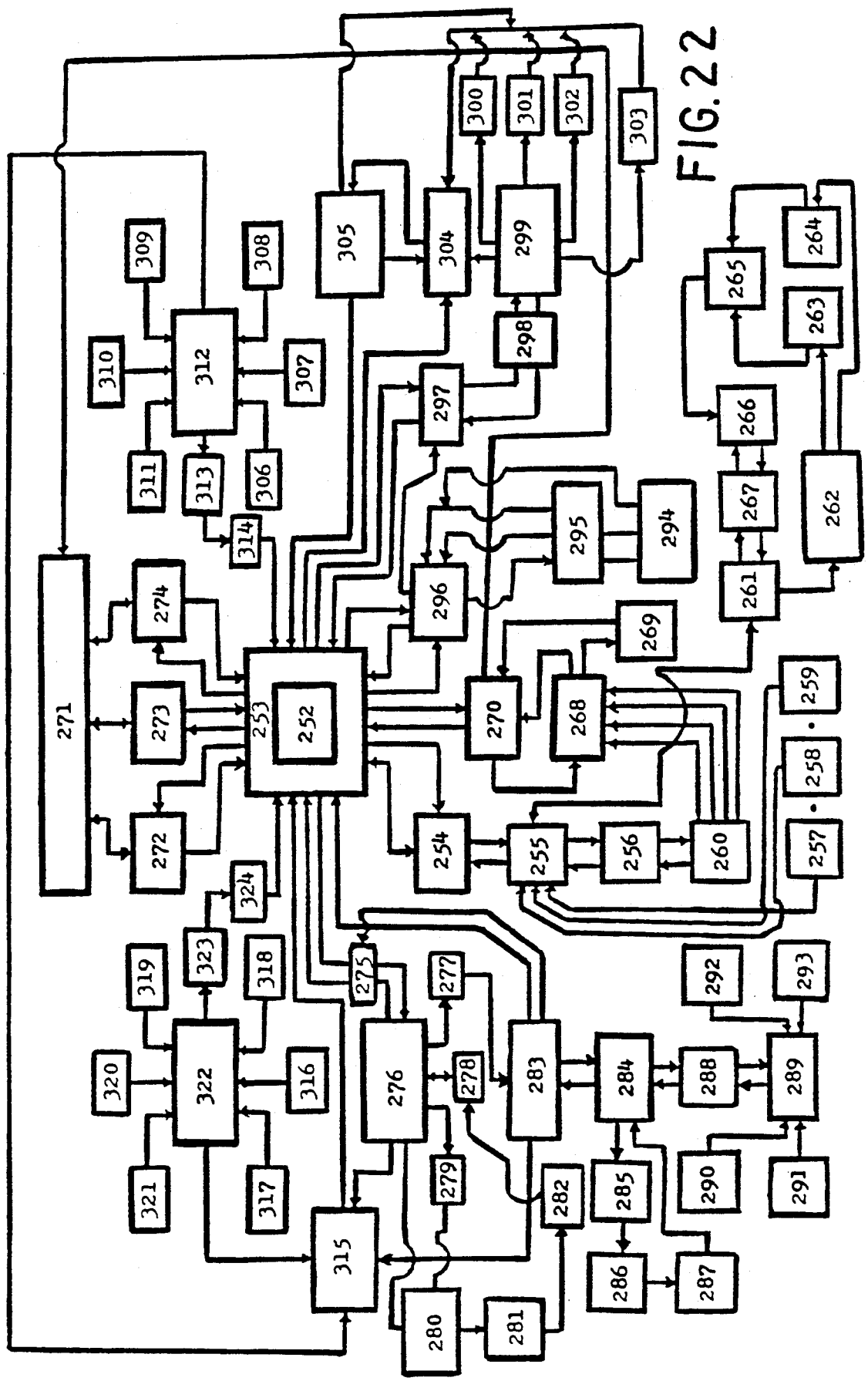
FIG. 22 is a concise block diagram illustrating how subsystems embodied within said invention operate and interact with one another.

FIG. 22 is a concise block diagram illustrating the operation of the cryogenic mean field generator device indicating the inter-relationship of subsystems embodied within said device. The CPU described by numeral 252 is centrally located and interfaced with an electro-optical I/O bridge defined by numeral 253, wherein command signals and power are conveyed from the CPU to other subordinate subsystems. Prior to subjecting a given specimen to temperatures below the nucleation temperature blood fluids are withdrawn and replaced by profusiates. Numerals 253 through 266 collectively describe the apparatuses whereby blood and other bodily fluids are removed and subsequently replaced by said profusiates, or visa versa during the recovery stage of cryogenic suspension. Element 254 describes a controller to activate subsystems through commands conveyed by the CPU and conveys the operational status or output of said subsystems to said CPU. Controller 254 engages sequencer means 255, which controls the output of profusiates and other substances from reservoirs 256 through 258 and blood circulating pump element 261. The contents obtained from reseriors 256, 257 and 258 represent a variety of chemical substances, which are amalgamated or chemically combined within mixing chamber 259; which is engaged by sequencer means 258. The contents from mixing chamber 259 are conveyed with an automated hypodermic injection element, described by numeral 260. Sequencer means 255 is further coupled to a channel leading to a automated reversible-variable speed circulating pump element, described by number 261, which withdraws and subsequently replaces blood and other bodily fluids from said tissues and organs. Said pump element 261 is coupled to centrifuge element 262, which separates said blood and bodily fluids into their subsequent components for storage. Said separated components are stored separately in reservoirs 263, 264; until needed in the aforementioned recovery stage, wherein said components are to assist in circulating coolants, providing low power when coupled to generators to ancillary systems and to operate hydraulic systems via pressure gradients where possible. Said Stirling engines are further coupled to a condenser element described by element 281, which conveys its contents to regenerator means 282; which reconveys said contents to circulator means 278. Circulator means 278 re-engages element 276, wherein said contents are recycled.

Data from element 277 is conveyed to atmospheric disseminator means 283, which interfaces with the CPU, number 252, through controller element 275. Element 283 engages an automated multivariant compressor pump, described by element 284, which provides forwards and reverse compression. Unit 284 conveys its contents to regenerator means 285, which recovers expended atmospheric gases and restores said gaseous constituents. The contents of regenerator 285 is upon processing conveyed to storage vessel 286 which holds said contents to recycling element 287. The regenerated contents contained within storage means 286 are released from recycling element 287 into unit 284 which upon command signals re-engages element 283. Unit 283 upon command signals engage amalgamation element 288, where various gaseous constituents obtained from gasifier means 289 are combined prior to their release. Gaseous substances enter gasifier means 289 from a series of storage vessels 290, 292, 293 and 294, respectively. Subsystems embodied within the cryogenic suspension device are powered by a reliable source of electrical power source described by unit 294, which is conveyed to regulator element 295, which in turn disperses said power to distributor means 296. Power is conveyed from distributor element 296 to means 297 which steps up the voltage, alters the polarity and adjusts the current of said voltage. Energy from said transformer recombined by regenerator means 265. The contents of regenerator means 265 are conveyed to chemical processing plants 266, 267 wherein expended volatile components vitamins, enzymes and other substances are replaced. The contents collectively obtained from units 266, 267 are conveyed through the same said channel back from pump means 261 to sequencer 255, which conveys its contents to elements 256, 260 respectively. The contents contained within said hypodermic injection means 260 are conveyed to dialyzer element 268, which is interfaced with the aforesaid specimen, described by number 269, through I.V. tubes, as described in FIGS. 13, 13a. The operational readiness and output of the aforementioned subsystems are conveyed through feedback unit 270 to CPU 252 and auxiliary CPU 271. Auxiliary CPU element 271 engages ancillary systems 272, 273 and volatile memory/display 274, which is interfaced with elements 252, 253 respectively. In order to avoid the formation of ice the temperature has to be dropped rapidly to below the nucleation temperature and the pressure must be substantially increased beyond several atmospheres; which is the function of the cryogenic compressor and reversible pump means, described collectively by element 276. Element 276 is coupled to atmospheric stablizer, numeral 277 circulator means 278 and a heat exchanger complex, described by numeral 279. The atmospheric stablizer means 277 alters the pressure and composition of gases within the cryogenic suspension unit (i.e. lowers the concentration of oxygen, the removal of $CO_2$ and the replacement of molecular nitrogen with helium or visa versa, as previously described in the specifications). Circulator means 278 uniformally distributes said atmospheric constituents and temperature through tissues and organs. Heat exchanger means 279 transfers the heat away from said cryogenic unit housing said tissues and organs and operates the Stirling engines, described by number 280. Said Stirling engines operate passively element 297 is dispersed to multiple wave generator means 298, wherein wave characteristics and other properties are generated for various emission means and multiplexed prior to being transmitted to sequencer means 299. Power and command signals are conveyed from element 299 to emitter source generators, described collectively by elements 300 through 303. Elements 300 through 303 collectively describe laser, radiofrequency, sonic beam generators and other source beam generator means. Data from elements 299 through 303 regarding output, internal operational status and other parameters are conveyed to feedback unit 304 prior to being conveyed to controller means 305, which engages all other said elements 297 through 304, including CPU 252.

Data obtained from infra-red, ultra-violet, radiofrequency laser and acoustic sensors described collectively by elements 306 through 311 is collected by collator 312. Data from sensory elements 306 to 311 is compilled, sorted, compared than catagorized by element 312 prior to being conveyed to integrator means 313, wherein said data is filtered. Data signals are transmitted from element 313 to amplifier means 314 prior to being conveyed to I/O bridge 253 and CPU, 252. Data from element 312 is simultaneously transmitted to data processor 315; wherein data undergoes statisticsl analysis. Sensory transducers monitoring temperature, pressure, electrical conductivity, laser spectroscopy, mechanical and fluid flow dynamics and other parameters are described collectively by elements 316 through 321. Data from sensory element 316 through 321 is conveyed to element 322, which engages elements 323, 324 and elements 322 through 324 correspond to elements 312, 313 and 314, respectively.

The preferred or best mode of cryogenic suspension and recovery can be summarized as a process containing eight steps. The first step consists of a gradual temperature drop from ambient conditions to within 10 degrees centigrade, the withdrawl of blood and other fluids from tissues or organs and the subsequent replacement of said blood and other fluids with a base profusiate. The second said step consists of purging potentially lethal or deleterious gaseous elements which are concentrated and may irreversibly bind; or react with tissues unless removed and replaced by inert gases, such as argon or helium. Said gases which are purged include but are not limited to carbon monoxide, oxides of nitrogen, sulfides and molecular nitrogen. The third step consists of introducing a vitrifiable solution which is optimally composed of 12.8% W/V DMSO, 12.8 W/V propylene glycol, 19.4% W/V acetamide (AA),PG 6% W/V, PVP 15% W/V and 44% W/V HES, sucrose, proteins and colioids to profuse said tissues, as the temperature is lowered to 0° C. to −10° C. The fourth said step consists of rapidly increasing the pressure 500 atmosphere per minute and lowering the temperature to within −130° C. ±15° C. within a period of several minutes. The fifth said step consists of subjecting said tissues to electromagnetic fields and sympathetic vibrations in order to uniformly dispersing chemical species and sustain and propagate the electronic vibrational frequencies for molecular water, preventing the formation and alignment of crystals. The sixth said step consists of the recovery period in which the pressure is uniformly drop, 500 atmospheres per minute and the temperature in said tissues is optimally raised from 200° C. to 300° C. per minute by bombarding said tissues with the energy, frequency and wavelengths corresponding to the vibrational frequency, infrared and Ramon vibrational spectrum for molecular water. An array of microwave lasers and radiofrequency generators provide excitation of said tissues; whereas acoustic emissions generated by an array of piezoelectric units emit frequencies corresponding to the transmissions of sound through liquified water. The seventh said step consists of withdrawing the base profusiate and other substances from said tissues and replacing said solutions with oxygenated Flurosal-43, followed by the reintroduction of enriched whole blood and other substances originally contained within said tissue, existing prior to the state of cryogenic suspension. The eighth step consists of the readministration of enzyme, vitamins, metabolic stablants, electrolytes and other substances damaged or destroyed during the process of cryogenic suspension and the recovery period. The build up of indogenous toxic wastes and other potentially lethal substances are removed from said tissues prior to obtaining conditions of ambient temperatures and pressure (STP 25° C. at 1 atmosphere). Toxins are removed from fluids circulating through or profusing said tissues by filtration, dialysis and other techniques well known by those skilled in the art. Any variations of the above mentioned steps 1 through 8 occuring because of variances in temperature, pressure, concentration or ratios of substances used in the suspension and/or recovery processes are well within the scope of the invention and understood by those skilled in the art.

Although various alterations or modifications may be suggested by those skilled in the art, it is the intention of the inventors to embody within the patent warranted hereon all changes and modifications as reasonably and properly come within the scope of contributions to the art, without departing from the spirt of the invention.

We claim:

1. The method of achieving cryogenic suspension in tissues or organs, including the steps of:
   replacing the blood in living tissues or organs with a sustaining solution comprising cryoprotectants, baroprotectants, antitoxinogens and metabollic stablants, said tissues or organs and said sustaining solution being maintained at a pressure exceeding atmospheric pressure;
   storing the blood from the tissues or organs;
   subjecting the tissues or organs to depressed temperatures in the range of the freezing temperature of said sustaining solution;
   maintaining said depressed temperature in a range to achieve in said sustaining solution a non-crystalline solid state;
   subjecting said tissues or organs to electromagnetic fields at predetermined frequencies corresponding to the vibrational frequency and vibrational spectroscopy of molecular water equivalent to the Raman and infra-red spectra for molecular water; and,
   simultaneously subjecting said tissues or organs to sonic waves of a predetermined frequency whereby crystallization of the sustaining solution is avoided while vitrification and subsequent recovery of tissues and organs is achieved wherein said sonic waves having predetermined frequencies which inhibit the nucleation and alignment of ice crystals and assist to uniformly disperse solutes dissolved in said sustaining solution coresponding to the harmonic frequencies exhibited by molecular water and depending on the colligative properties existing within said sustaining solution embodied within said tissues and 2. The method according to claim 1 which includes the additional step of raising the temperature of said tissue or organs to ambient condition while applying electromagnetic and sonic energy thereto.

3. The method according to claim 2 which includes the additional step of replacing the sustaining solution with the previously stored blood of said tissues or organs.

4. The method according to claim 1 in which the cryoprotectant includes penetrating, glass-forming compounds and non-penetrating glass-forming compounds.

5. The method according to claim 4 in which the penetrating glass-forming compounds include DMSO.

6. The method according to claim 4 in which the non-penetrating glass-forming compounds include compounds of polyvinylpyrrolidone.

7. The method of according to claim 1 in which one of the antitoxinogens is an amide.

8. The method according to claim 1 which includes the additional steps of leaching accumulated nitrogen from said tissues or organs and replacing the nitrogen with helium following said step of replacing the blood and before said step of subjecting said tissues or organs to depressed temperatures.

9. The method according to claim 1 in which said sustaining solution includes an osmotic antagonist.

10. The method according to claim 9 in which said osmotic antagonist is mannitol.

11. The method according to claim 1 which includes the additional step of subjecting said tissues or organs to infra-red laser emissions which uniformly elevates the temperature of said tissues or organs optimally from 200° C. to 300° C. per minute for the purpose of recovery of said tissues or organs.

* * * * *